(12) United States Patent
Sanders

(10) Patent No.: US 10,195,010 B2
(45) Date of Patent: Feb. 5, 2019

(54) METHODS AND DEVICES FOR TREATING SLEEP APNEA AND SNORING

(75) Inventor: Ira Sanders, North Bergen, NJ (US)

(73) Assignee: Linguaflex, Inc., Davie, FL (US)

( * ) Notice: Subject to any disclaimer, the term of this patent is extended or adjusted under 35 U.S.C. 154(b) by 208 days.

(21) Appl. No.: 13/299,632

(22) Filed: Nov. 18, 2011

(65) Prior Publication Data

US 2012/0227748 A1     Sep. 13, 2012

Related U.S. Application Data

(63) Continuation of application No. 12/011,782, filed on Jan. 29, 2008, now Pat. No. 8,074,655, which is a continuation-in-part of application No. 11/672,019, filed on Feb. 6, 2007, which is a continuation-in-part of application No. 10/597,590, filed as application No. PCT/US2005/006430 on Feb. 28, 2005, now Pat. No. 8,925,551.

(60) Provisional application No. 60/765,638, filed on Feb. 6, 2006, provisional application No. 60/547,897, filed on Feb. 26, 2004.

(51) Int. Cl.

| A61F 5/56 | (2006.01) |
|---|---|
| A61F 2/00 | (2006.01) |
| A61B 17/04 | (2006.01) |
| A61B 17/06 | (2006.01) |
| A61B 17/24 | (2006.01) |
| A61B 17/30 | (2006.01) |

(52) U.S. Cl.
CPC ............ *A61F 2/00* (2013.01); *A61B 17/0401* (2013.01); *A61F 5/566* (2013.01); *A61B 2017/0417* (2013.01); *A61B 2017/0419* (2013.01); *A61B 2017/0496* (2013.01); *A61B 2017/06052* (2013.01); *A61B 2017/248* (2013.01); *A61B 2017/306* (2013.01); *A61B 2017/308* (2013.01)

(58) Field of Classification Search
CPC ...... A61F 5/566; A61F 5/56; A61B 2017/248; A61B 17/24
USPC .................. 128/848, 846; 602/902; 433/140
See application file for complete search history.

(56) References Cited

U.S. PATENT DOCUMENTS

| 3,517,669 A | 6/1970 | Buono et al. |
|---|---|---|
| 3,659,612 A | 5/1972 | Shiley et al. |
| 4,254,774 A | 3/1981 | Boretos |
| 4,335,723 A | 6/1982 | Patel |
| 4,387,879 A | 6/1983 | Tauschinski |
| 4,704,111 A | 11/1987 | Moss |

(Continued)

FOREIGN PATENT DOCUMENTS

| DE | 197 56 956 | 7/1999 |
|---|---|---|
| JP | 2000-060862 | 2/2000 |

(Continued)

OTHER PUBLICATIONS

Doghramji, K., M.D. et al., *Predictors of Outcome for Uvulopalatopharnygoplasty*, Laryngoscope, vol. 105, pp. 311-314, 1995.

(Continued)

*Primary Examiner* — Victoria J Hicks
(74) *Attorney, Agent, or Firm* — The Webb Law Firm

(57) ABSTRACT

Methods and devices to prevent and/or treat breathing disorders (e.g., upper airway disorders) in mammals related to impaired airflow are described. Methods and devices apply force to soft tissue that avoids obstruction of airflow in the mammel's airway. Breathing disorders that are avoided by the methods and/or devices include apnea.

13 Claims, 24 Drawing Sheets

(56) References Cited

U.S. PATENT DOCUMENTS

| | | |
|---|---|---|
| 4,907,602 A | 3/1990 | Sanders |
| 4,981,477 A | 1/1991 | Schon et al. |
| 5,109,850 A | 5/1992 | Blanco et al. |
| 5,190,053 A | 3/1993 | Meer |
| 5,250,049 A | 10/1993 | Michael |
| 5,376,110 A | 12/1994 | Tu et al. |
| 5,464,395 A | 11/1995 | Faxon et al. |
| 5,480,420 A | 1/1996 | Hoegneld et al. |
| 5,498,247 A | 3/1996 | Brimhall |
| 5,591,216 A | 1/1997 | Testerman et al. |
| 5,694,922 A | 12/1997 | Palmer |
| 5,792,067 A | 8/1998 | Karell |
| 5,797,913 A | 8/1998 | Dambreville et al. |
| 5,843,021 A | 12/1998 | Edwards et al. |
| 5,954,050 A | 9/1999 | Christopher |
| 5,961,440 A | 10/1999 | Schweich et al. |
| 5,976,109 A | 11/1999 | Heruth |
| 5,980,557 A | 11/1999 | Iserin et al. |
| 5,988,171 A | 11/1999 | Sohn et al. |
| 5,989,244 A | 11/1999 | Gregory et al. |
| 5,997,567 A | 12/1999 | Cangelosi |
| 6,013,728 A | 1/2000 | Chen et al. |
| 6,132,384 A | 10/2000 | Christopherson et al. |
| 6,161,541 A | 12/2000 | Woodson |
| 6,251,059 B1 | 6/2001 | Apple et al. |
| 6,267,775 B1 | 7/2001 | Clerc et al. |
| 6,408,851 B1 | 6/2002 | Karell |
| 6,409,720 B1 | 6/2002 | Hissong et al. |
| 6,439,238 B1 | 8/2002 | Brenzel et al. |
| 6,546,936 B2 | 4/2003 | Knudson et al. |
| 6,547,787 B1 | 4/2003 | Altman et al. |
| 6,558,321 B1 | 5/2003 | Burd et al. |
| 6,601,584 B2 | 8/2003 | Knudson et al. |
| 6,610,065 B1 | 8/2003 | Branch et al. |
| 6,618,627 B2 | 9/2003 | Lattner et al. |
| 6,636,767 B1 | 10/2003 | Knudson et al. |
| 6,636,769 B2 | 10/2003 | Govari et al. |
| 6,742,524 B2 | 6/2004 | Knudson et al. |
| 6,764,446 B2 | 7/2004 | Wolinsky et al. |
| 6,921,401 B2 | 7/2005 | Lerch et al. |
| 6,955,172 B2 | 10/2005 | Nelson et al. |
| 7,146,981 B2 | 12/2006 | Knudson et al. |
| 7,188,627 B2 | 3/2007 | Nelson et al. |
| 7,237,554 B2 | 7/2007 | Conrad et al. |
| 7,337,781 B2 | 3/2008 | Vassallo |
| 2001/0050084 A1 | 12/2001 | Knudson et al. |
| 2001/0050085 A1 | 12/2001 | Knudson |
| 2001/0054428 A1 | 12/2001 | Knudson et al. |
| 2002/0189622 A1 | 12/2002 | Cauthen, III et al. |
| 2003/0069626 A1 | 4/2003 | Lattner et al. |
| 2003/0093128 A1 | 5/2003 | Freed et al. |
| 2003/0125743 A1 | 7/2003 | Roman et al. |
| 2004/0045556 A1 | 3/2004 | Nelson et al. |
| 2005/0004417 A1 | 1/2005 | Nelson et al. |
| 2005/0092332 A1 | 5/2005 | Conrad et al. |
| 2005/0092334 A1 | 5/2005 | Conrad et al. |
| 2006/0201519 A1 | 9/2006 | Frazier et al. |
| 2006/0207606 A1 | 9/2006 | Roue et al. |
| 2006/0235264 A1 | 10/2006 | Vassallo |
| 2007/0119463 A1 | 5/2007 | Nelson et al. |
| 2007/0144534 A1 | 6/2007 | Mery et al. |
| 2007/0288057 A1 | 12/2007 | Kuhnel |
| 2008/0021485 A1 | 1/2008 | Catanese, III et al. |
| 2008/0023012 A1 | 1/2008 | Dineen et al. |
| 2008/0027560 A1 | 1/2008 | Jackson et al. |
| 2008/0066766 A1 | 3/2008 | Paraschac et al. |
| 2008/0066767 A1 | 3/2008 | Paraschac et al. |
| 2008/0078412 A1 | 4/2008 | Buscemi et al. |
| 2009/0177027 A1 | 7/2009 | Gillis |

FOREIGN PATENT DOCUMENTS

| | | |
|---|---|---|
| JP | 2008-526286 | 7/2008 |
| WO | 99/32057 | 7/1990 |
| WO | 92/21291 | 12/1992 |
| WO | 97/21385 | 6/1997 |
| WO | 99/00058 | 1/1999 |
| WO | 2000/029063 | 5/2000 |
| WO | 2003/092765 | 11/2003 |
| WO | 2004/064729 A2 | 8/2004 |
| WO | 2005/044158 A1 | 5/2005 |
| WO | 2005/082452 | 9/2005 |
| WO | 2005/110280 | 11/2005 |
| WO | 2007/064908 A2 | 6/2007 |
| WO | 2007/092865 | 8/2007 |

OTHER PUBLICATIONS

Freidman M., et al., "Minimally Invasive Single-Stage Multilevel Treatment for Obstructive Sleep Apnea/Hypopnea Syndrome", The Laryngoscope (Oct. 2007)vol. 117, pp. 1859-1863.

Horner, R., *Motor control of the Pharyngeal Musculature and Implications for the Pathogenesis of Obstructive Sleep Apnea*, Sleep, vol. 19, pp. 827-853, 1996.

Krespi, Yosef, P., et al., "Hyoid Suspension for Obstructive Sleep Apnea", Operative Techniques in Otolaryngology-Head and Neck Surgery (Jun. 2002), vol. 13, No. 2, pp. 144-149.

Loube, D., M.D., *Technologic Advances in the Treatment of Obstructive Sleep Apnea Syndrome*, Chest, vol. 116, pp. 1426-1433, 1999.

Mickelson, S., M.D. et al., *Midline Glossectomy and Epiglottidectomy for Obstructive Sleep Apnea Syndrome*, Laryngoscope, vol. 107, pp. 614-619, 1997.

Mintz, S.M., et al., "A Modified Geniotomy Technique for Obstructive Sleep Apnea Syndrome", J. Oral Maxillofac Surgery (1995), vol. 53, pp. 1226-1228.

Nordgård, S., et al., "One-year Results: Palatal Implants for the Treatment of Obstructive Sleep Apnea", Otolaryngology—Head and Neck Surgery (2007), vol. 136, pp. 818-822.

Powell, N., M.D. et al, *Radiofrequency Volumetric Tissue Reduction of the Palate in Subjects with Sleep-Disordered Breathing*, Chest, vol. 113, pp. 1163-174, 1998.

Proffit, W., D.D.S., Ph.D., Muscle Pressures and Tooth Position: A Review of Current Research, Australian Orthodontic Journal, pp. 104-108, 1973.

Riley, R.W., et al., "Surgery and Obstructive Sleep Apnea:Long-Term Clinical Outcomes", Operative Techniques in Otolaryngology—Head and Neck Surgery (Mar. 2007), vol. 122, No. 3, pp. 415-421.

Rotunda, A., M.D. et al., *Detergent Effects of Sodium Deoxycholate Are a Major Feature of an Injectable Phosphatidylcholine Formulation Used for Localized Fat Dissolution*, Dermatologic Surgery, vol. 30(7), pp. 1001-1008, 2004.

Strollo, P. et al., Medical Therapy for Obstructive Sleep Apnea-Hypopnea Syndrome, *Principles and Practice of Sleep Medicine*, 4th ed. pp. 1053-1065, 2005.

Treiber, E., M.D. et al., *Breast Deformity Produced by Morphea in a Young Girl*, Cutis, vol. 54, pp. 267-268, 1994.

Vicente, E., MD., et al., "Tongue-Base Suspension in Conjunction with Uvulopalatopharyngoplaty for Treatment of Severe Obstructive Sleep Apnea; Long-Term Follow-Up Results," Laryngoscope (vol. 116); Jul. 2006, pp. 1223-1227.

Woodson, B.T., MD., et al., "Pharyngeal Suspension Suture with Repose bone Screw for Obstructive Sleep Apnea", Otolaryngology—Head and Neck Surgery (Mar. 2000), vol. 122, No. 3, pp. 395-401.

Woodson, B. T., "A Tongue Suspension Suture for Obstructive Sleep Apnea and Snorers", Operative Techniques in Otolaryngology—Head and Neck Surgery (Mar. 2001), vol. 124, No. 3, pp. 297-303.

Woodson, B.T., MD., et al., "A Randomized Trial of Temperature-Controlled Radiofrequency, continuous Positive Airway Pressure, and Placebo for Obstructive Sleep Apnea Syndrome", Otolaryngology—Head and Neck Surgery (Jun. 2003), vol. 128, No. 6, pp. 848-861.

International Search Report from PCT/2005/06430, 1 page.

International Search Report to PCT/US2009/60991, dated Jan. 7, 2010, 3 pages.

International Search Report to PCT/2007/61721, 2 pages.

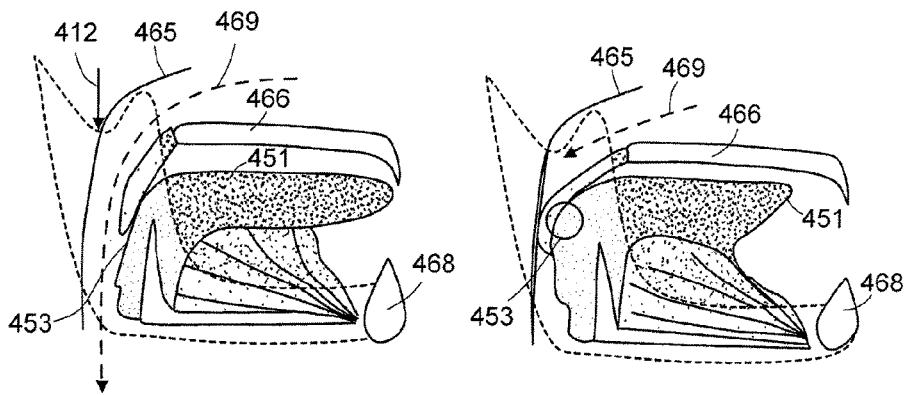
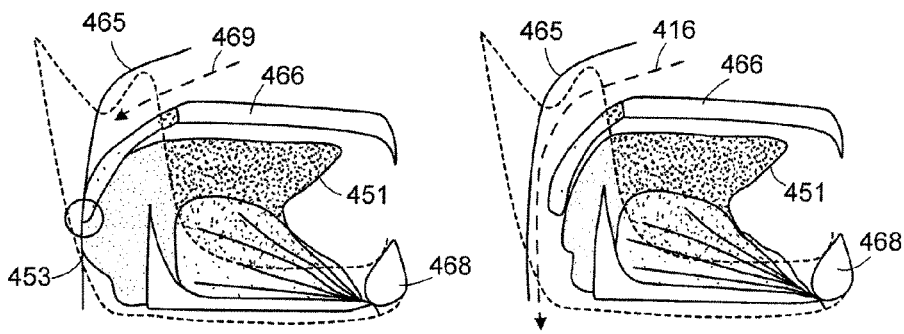
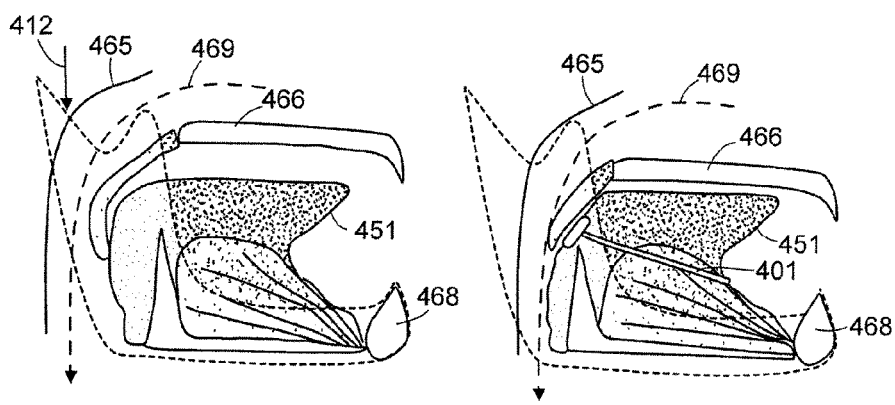
FIG. 4A   FIG. 4B   FIG. 4C   FIG. 4D   FIG. 4E   FIG. 4F

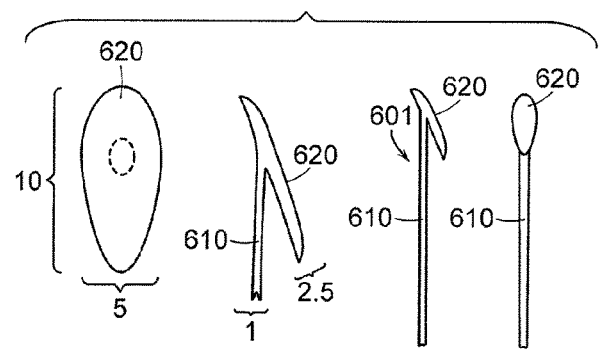 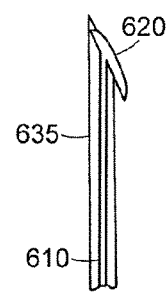
FIG. 6A         FIG. 6B
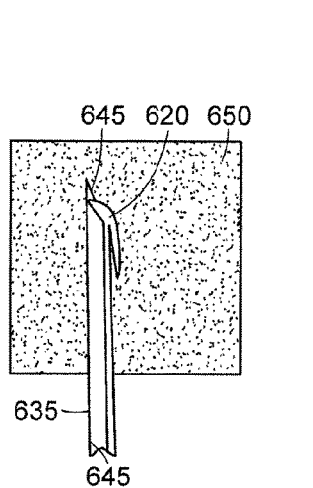 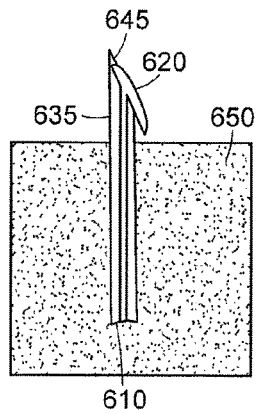 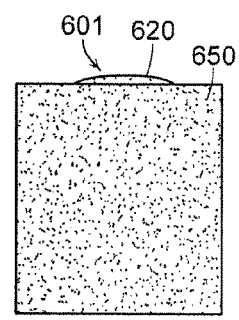
FIG. 6C         FIG. 6D         FIG. 6E

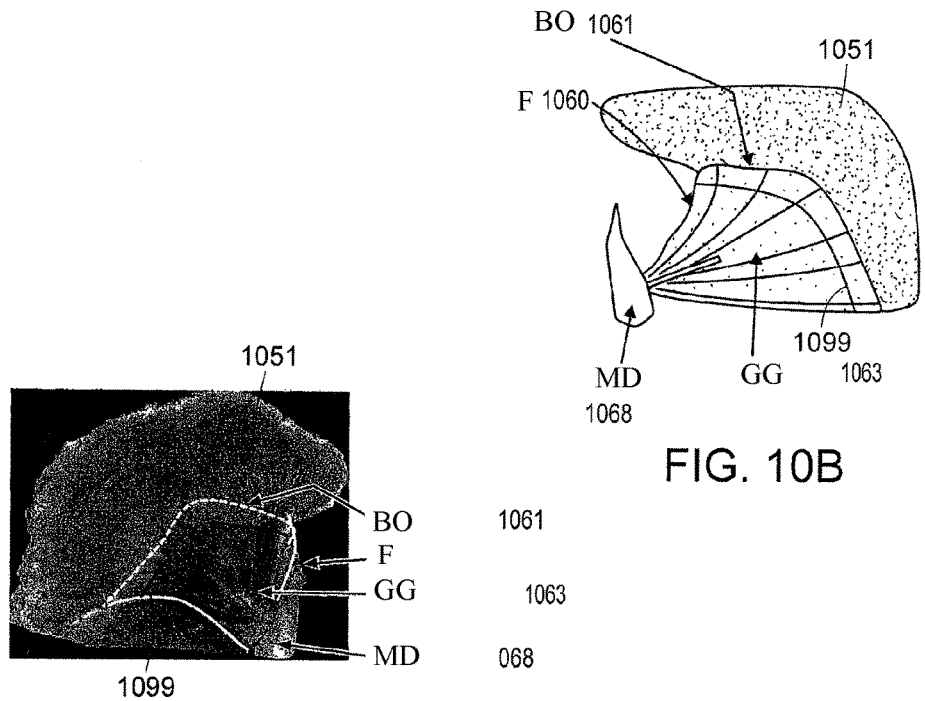
FIG. 10B
FIG. 10A
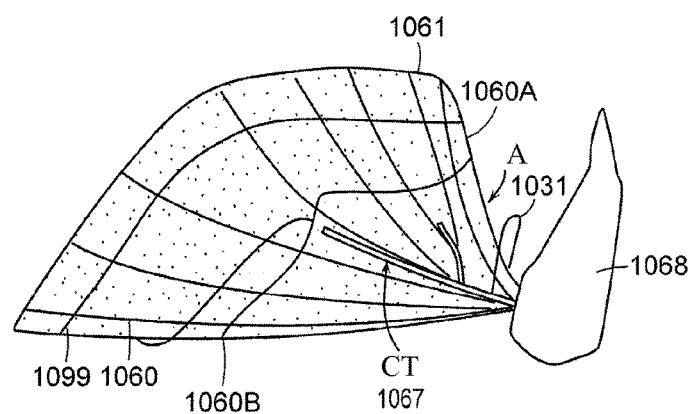
FIG. 10C

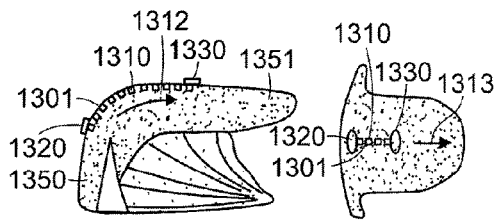 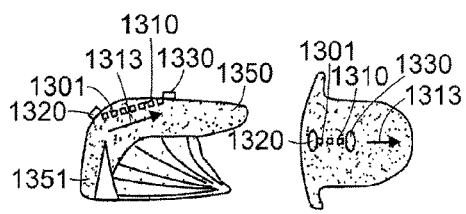
FIG. 13A  FIG. 13B
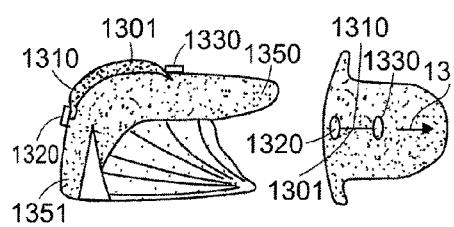 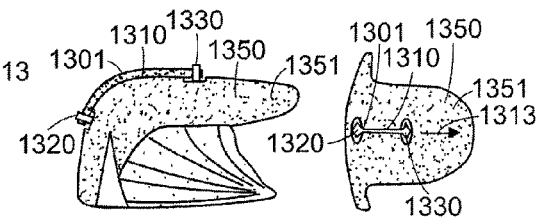
FIG. 13C  FIG. 13D
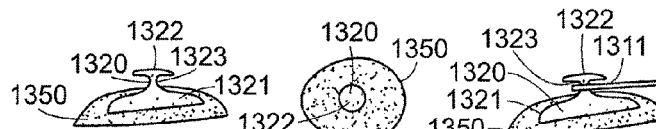 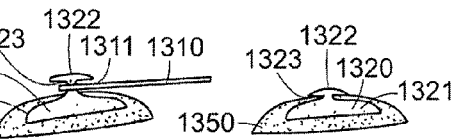
FIG. 13E  FIG. 13F  FIG. 13G  FIG. 13H
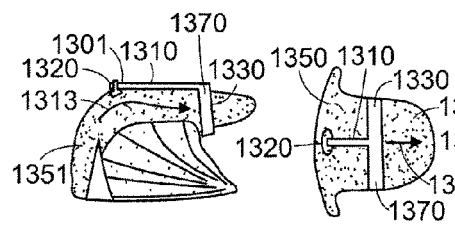 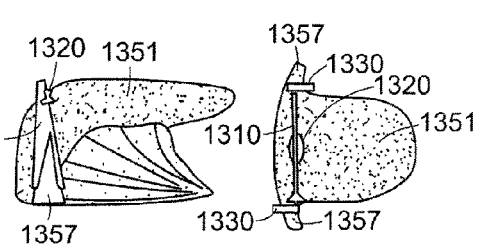
FIG. 13I  FIG. 13J
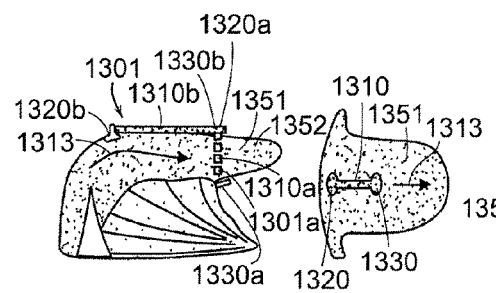 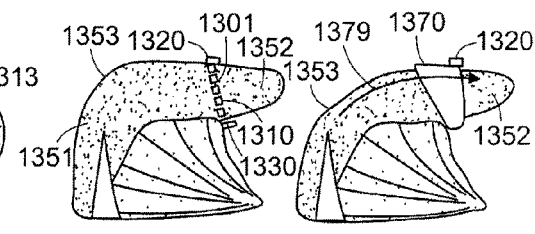
FIG. 13K  FIG. 13L

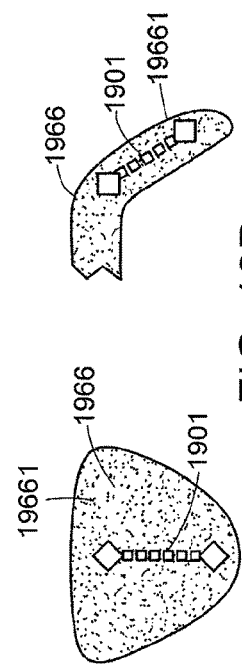 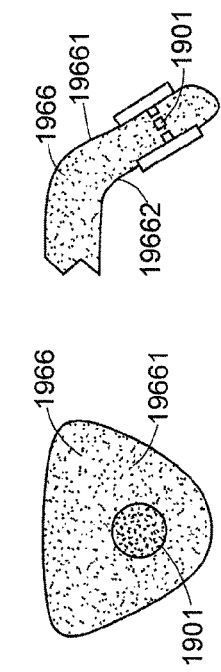 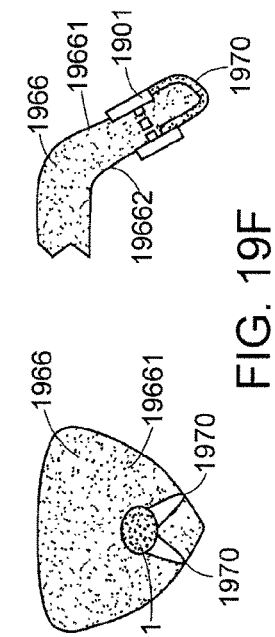
FIG. 19D  FIG. 19E  FIG. 19F
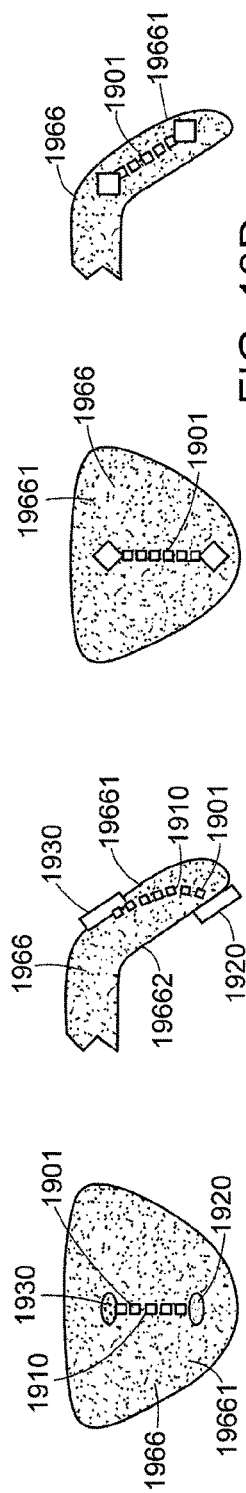 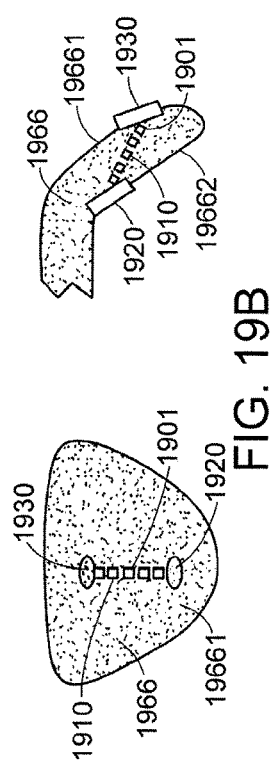 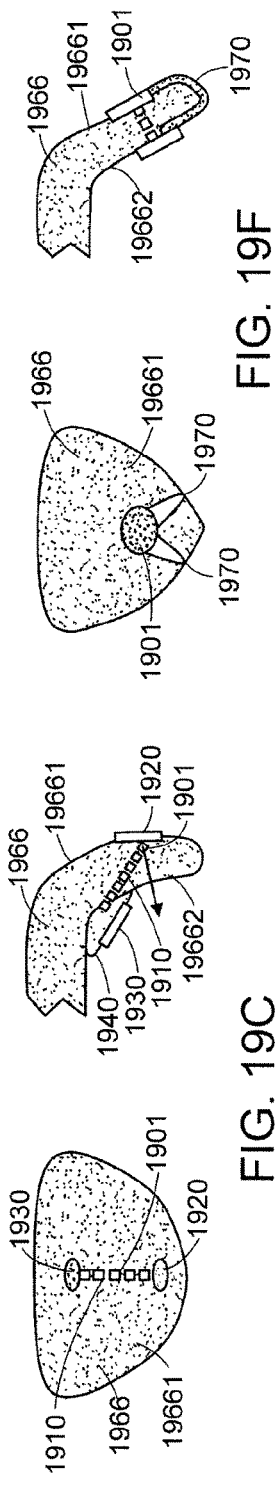
FIG. 19A  FIG. 19B  FIG. 19C

METHODS AND DEVICES FOR TREATING SLEEP APNEA AND SNORING

CROSS REFERENCE TO RELATED APPLICATIONS

This application is a continuation of U.S. patent application Ser. No. 12/011,782, filed Jan. 29, 2008, which is a continuation-in-part of U.S. patent application Ser. No. 11/672,019, filed Feb. 6, 2007, which claims the benefit of U.S. Provisional Patent Application No. 60/765,638, filed on Feb. 6, 2006 and is a continuation-in-part of U.S. patent application Ser. No. 10/597,590, filed Jul. 31, 2006, which is a national stage filing under 35 U.S.C. § 371 of International Patent Application No. PCT/US2005/006430, filed Feb. 28, 2005, which claims the benefit of U.S. Provisional Patent Application No. 60/547,897, filed Feb. 26, 2004, each of these applications are hereby incorporated by reference herein in their entirety.

FIELD OF THE INVENTION

This invention relates to methods and devices for maintaining upper airway patency.

BACKGROUND OF THE INVENTION

Snoring, upper airway resistance syndrome, and obstructive sleep apnea syndrome (OSAS) are all related to narrowing or obstruction of the upper airway during sleep (sleep disordered breathing). According to the National Institutes of Health (NIH), approximately 18 million Americans have sleep apnea (sleep disordered breathing), but fewer than 50% are presently being diagnosed. According to the National Highway Traffic and Safety Administration (NHTSA), 100,000 accidents and 1,500 traffic fatalities per year are related to drowsy driving. More than 50% of Americans over age 65 have sleep difficulties, and prevalence of sleep problems will therefore increase as the over-65 population increases. Each year, sleep disorders, sleep deprivation, and excessive daytime sleepiness add approximately $16 billion annually to the cost of health care in the U.S., and result in $50 billion annually in lost productivity.
Pathophysiology of Sleep Disorders Sleep disorders are largely caused by too much soft tissue in the throat. Humans are unique because their upper airway has a curved shape, an anatomical change that is related to the evolution of human speech. As a result the upper airway of humans is more flexible than that of other species and is more prone to collapse under negative pressure. In the awake state a certain amount of tone is present in upper airway muscles to prevent this collapse. However, during sleep muscle tone decreases in upper airway muscles and in certain susceptible individuals this relaxation allows the airway to collapse (Homer R L. Motor control of the pharyngeal musculature and implications for the pathogenesis of obstructive sleep apnea. *Sleep* 1996; 19: 827-853).

The upper airway refers to the air filled spaces between the nose and the larynx (FIG. 1). The most relevant part of the upper airway for sleep disorders is the air cavity at the back of the throat called the pharynx. The pharynx can be divided into three anatomical levels (FIG. 2):

1) The nasopharynx is the part of the pharynx in the back of the nasal cavity.

2) The part at the back of the mouth is called the oropharynx. The oropharynx is the space between the tongue and the pharynx from the edge of the soft palate to the tip of the epiglottis. To be more precise it is best called the velopharynx. This level corresponds to that part of the pharynx containing the velum (soft palate) and tongue curve.

3) The hypopharynx is behind the tongue base.

The velopharynx is more susceptible to collapse because there are more soft tissue structures, leaving less room for airflow. The major structures of the velopharynx are the soft palate and the tongue, both of which are very flexible. The soft palate acts as a barrier between the mouth and the nose. In many people it is longer than necessary and extends down between the tongue and pharyngeal wall. The tongue is the largest muscular organ of the upper airway and is anatomically divisible into a blade, body and base (FIG. 3). Most of the tongue's curve is at the junction of the tongue body and base.

In the awake condition the structures of the velopharynx maintain their shape because of continuous tone of their internal muscles. When this tone decreases, such as during sleep, these structures become quite flexible and distensible. Without the normal muscle tone that keeps them is place, they tend to collapse at relatively low negative pressures. Although muscles relax throughout the body during sleep many of the respiratory muscle remain active. Specifically, the major muscle that pulls the tongue forward, the genioglossus muscle, has been reported to show normal or increased activity during obstructive apneas. Normally the genioglossus is capable of moving the tongue forward and even projecting it out of the mouth. Why the genioglossus muscle sometimes fails to prevent obstructions has not been explained.

During inspiration the chest wall expands and causes negative pressure to draw air into the nose and mouth and past the pharynx into the lungs. This negative pressure causes upper airway soft tissue to deform, further narrowing the airway. If the airway narrows enough the air flow becomes turbulent causing the soft palate to vibrate. The vibration of the soft palate produces the sound known as snoring. Snoring is extremely common effecting up to 50% of men and 25% of women. By itself snoring is not a medical problem although it can be a tremendous problem for the patient's bed partner and a major cause of marital strain.

A small amount of decreased airflow or brief obstructions occur in all humans during sleep. These episodes are counted as medically significant if airflow is decreased more than 50% of normal for more then 10 seconds (hypopnea) or if airflow is obstructed for more then 10 seconds (apnea). The number of apneas and hypopneas that occur during each hour of sleep is measured to diagnose the severity of the sleep disorder. These episodes of hypopnea or apnea often cause some degree of arousal during sleep. Although the patient does not awaken to full consciousness, the sleep pattern is disturbed causing the patient to feel sleepy during the day. If the frequency of hypopnea or apnea is less than 5 episodes an hour it is called upper airway resistance syndrome. These patients often show symptoms related to the sleep disruption. Specifically, these patients are excessively sleepy during the day. In addition more subtle symptoms such as depression and difficulty in concentrating are also commonly reported. Snoring, hypopnea, and apnea can all be characterized as breathing disorders.

Technically the diagnosis of OSAS is defined as an average of more than 5 episodes of hypopnea or apnea during each hour of sleep. Although the airway is obstructed the patient makes repeated and progressively more forceful attempts at inspiration. These episodes are silent and characterized by movements of the abdomen and chest wall as the patient strains to bring air into the lungs. Episodes of apnea can last a minute or more, and during this time the oxygen levels in the blood decrease. Finally, either the obstruction is overcome, usually producing a loud snore, or the patient awakes with the feeling of choking.

Very common symptoms in OSAS patients are morning headaches and acid reflux. During airway obstructions the forceful attempts to inspire air can cause tremendous negative pressure in the chest. These high negative can draw acid up the esophagus from the stomach. The acid can travel all the way into the mouth and cause inflammation of the vocal cords and nasal mucosa. The presence of the acid in the upper airway causes reflex bronchoconstriction in the lung that is similar to an asthma attack. If even a small amount of acid enters the lung it can cause the vocal folds to close tightly and itself cause a prolonged apnea called laryngospasm. In many patients the repeated stretching of the espophageal sphincter causes chronic changes and these patients can have acid reflux during the day.

Most importantly, sleep disorders can cause serious medical disorders and death. Apneas cause a large strain on the heart and lungs. Over time the many repeated episodes of apnea cause chronic changes leading to hypertension. Long periods of apnea allow the oxygen levels in the blood to decrease. In turn the low oxygen can cause heart attacks or strokes.

Treatment of Sleep Disorders

Although OSAS occurs in both children and adults the cause and treatment is very different. OSAS in children almost always occurs when the child has large tonsils, and tonsillectomy cures the condition. Tonsils naturally decrease in size with age and are rarely a problem in adults. Instead susceptible adults usually have enlargement of their tongues, soft palate and/or pharyngeal walls. This enlargement is mostly due to fat deposits within these structures.

Adult sleep disorders are difficult to treat for a variety of reasons. The upper airway is a very mobile structure that performs the critical functions of swallowing and speech. These functions are easily compromised by surgical procedures or other interventions. In addition, the upper airway also has a large amount of sensory innervation that causes reflex gagging and coughing. Theoretically a physical stent that is placed in the oral cavity and pharynx would be completely effective in relieving sleep apnea. When a patient is totally unconscious, such as when they are anesthetized for surgery, the airway can be stented open by placing a curved oral tube into the mouth and pharynx. In addition, endotracheal tubes establish a secure airway for artificial ventilation. However, after anesthesia wears off, patients immediately sense and react to the foreign objects in their throats and expel them. Therefore devices such as oral and endotracheal tubes, or anything similar, cannot be used for the treatment of OSAS.

Although physical stents cannot be used for OSAS an indirect way of stenting the upper airway with positive air pressure is the most common prescribed treatment for OSAS. This method is called continuous positive airway pressure (CPAP). CPAP requires the use of a mask tightly attached around the nose and connected to a respirator. The exact amount of positive pressure is different for each patient and must be set by overnight testing using multiple pressures. The positive pressure acts like a stent to keep the airway open. CPAP is not a cure but a therapy that must be used every night. Although many OSAS patients are helped by CPAP it is not comfortable for the patient or their bed partner. Patients often cannot tolerate the claustrophobic feeling of a mask tightly attached to their face. In addition they are often many technical problems with maintaining a proper seal of the mask to the face. For these reasons up to half of all patients who are prescribed CPAP stop using it within 6 months (Sanders, "Medical Therapy for Sleep Apnea," Principles and Practice of Sleep Medicine, 2nd Edition, pp. 678-684).

Tracheotomy

The only completely effective surgical therapy for OSAS is to bypass the entire upper airway by performing a permanent tracheotomy, a surgical procedure that forms a direct connection to the trachea through the neck. This is a dangerous procedure reserved for the worst cases when there is a high risk of serious medical complications from OSAS. Notably, temporary tracheotomies are often performed on patients with severe OSAS to control the airway before performing before any other procedure is performed on their upper airway. The reason is that these patients are at high risk of acute airway obstruction and death if there is any swelling in their airways. Due to the tremendous excess of swollen tissue in their upper airways OSAS patients are very difficult to intubate under emergency conditions. Similarly there is tremendous amount of fat in the neck that makes emergency tracheotomies extremely hazardous.

Prior to current conservative measures, post operative deaths were not uncommon in severe OSAS patients. Moreover these patients often have acclimated to breathing against resistance, and when the resistance is suddenly removed their respiratory drive decreases. Even today the standard of care in treating most OSAS patients is to have them under close observation in an intensive care unit or recovery room after surgical procedures.

Soft Palate Procedures For Snoring

As the soft palate vibrates more than other tissues it plays a disproportional role in snoring. Various surgical therapies are available that shrink or stiffen the soft palate. The main procedure used is called uvulopalatopharyngoplasty (UPPP). UPPP excises excess soft tissue of the pharyngeal walls and soft palate with a surgical scalpel. Because so much mucosa of the pharyngeal area is traumatized during a UPPP there is a large amount of post operative swelling and severe pain. In selected patients who snore but have no obstructions more limited versions of the UPPP can be done with lasers or electrical cautery.

Newer procedures minimize trauma to the mucosa and use needles to reach the underlying soft tissue to shrink its volume or stiffen it so that it resists vibration. Electrodes can be inserted into the soft palate to deliver radiofrequency energy that shrinks or stiffens the palate (Powell, N B, et al (1998) Radiofrequency volumetric tissue reduction of the palate in subjects with sleep-disordered breathing. Chest 113, 1163-1174.) (Somnoplasty; Somnus; Mountainview, Calif.). Mild caustic agents can be injected that decrease the volume of the soft palate. U.S. Pat. No. 6,439,238 to Benzel teaches the application of a stiffening agent to the surface of the soft palate. Most recently, office based implantation of plastic inserts to stiffen the soft palate has been approved by the FDA (Pillar® Procedure, U.S. Pat. No. 6,546,936: Method and apparatus to treat conditions of the nasopharyngeal area).

The fundamental shortcoming of all procedures that target the soft palate, including the newer techniques, is that they only partially improve OSAS (Loube D I (1999) Technologic Advances in the Treatment of Obstructive Sleep Apnea Syndrome. Chest. 1999; 116:1426-1433, Doghramji, K, et al (1995) Predictors of outcome for uvulopalatopharyngoplasty. Laryngoscope 105, 311-314). Although studies report a decrease in the number of apneas, these patients are rarely cured. Evidently the critical structure causing OSAS is not the soft palate but the tongue.

Tongue Base Procedures for OSAS

The methods used to treat the tongue base in OSAS are either to permanently decrease its volume, to decrease its flexibility or to move the entire tongue forward. Surgical excision of the tongue base has been poorly effective. The results for scalpel or laser resection of the tongue base in OSAS treatment have not been good enough to recommend continued application of these procedures (Mickelson, S A, Rosenthal, L (1997). Midline glossectomy and epiglottidectomy for obstructive sleep apnea syndrome. Laryngoscope 107, 614-619).

More recently radiofrequency (U.S. Pat. No. 5,843,021 to Edwards) and ultrasonic (U.S. Pat. No. 6,409,720) energy have been proposed to shrink and stiffen the tongue base with radiofrequency energy. The radiofrequency energy is delivered via needle electrodes that are inserted into the tongue base to cause a lesion that scars and shrinks over time. To avoid postoperative swelling and pain a limited amount of lesioning is done in a single session and patients require an average of 5 treatments. About a third of patients have greater than 50% improvement in their OSAS. However, approximately a fourth of patients have significant post operative complications, including, tongue base ulceration and abscesses, and temporary tracheotomy.

A recent introduced device for tongue base advancement is the Repose® system (Influent Corp; San Francisco, Calif.). The procedure is performed under general anesthesia, and the Repose® system includes insertion of a screw at the base of the mandible. The screw contains attachments for a permanent suture that is tunneled under the mucosa of the floor of the mouth to the back of the tongue, then passed across the width of the tongue base, and brought back to attach to a metal hook screwed into the bone of the mandible. The suture is tightened to displace the tongue base forward, and caution must be observed to prevent excess tension leading to necrosis of tissue. Unfortunately studies of the Repose® procedure show that it is ineffective at eliminating OSAS. Only 1 of 15 patients was cured of OSAS while 2 patients had to have the suture removed due to pain and swelling.

More aggressive surgical procedures require reconstruction of the mandible, facial, skeleton or the hyoid bone. An example of the art is U.S. Pat. No. 6,161,541 to Woodson that teaches a method of surgically expanding the pharyngeal airway. These procedures require extensive surgery with higher risks and much longer recovery periods.

Other proposed methods for treating the tongue base include stiffening the soft tissue by injection of sclerosing particles U.S. Pat. No. 6,742,524 or other implanted material US Patent Application Publication No. 20050004417A1.

Neuroprosthetic Devices

Various neuroprosthetic devices have been invented that stimulate upper airway muscles. U.S. Pat. No. 4,907,602 to Sanders describes transmucosal stimulation to dilate the airway; U.S. Pat. No. 5,792,067 to Karell teaches an intraoral device that applies electrical stimulation to the hard palate, soft palate or pharyngeal area to induce contraction of the upper airway muscles; U.S. Pat. No. 5,190,053 to Meer teaches an intraoral device that applies electrical stimulation to the genioglossus muscle via electrodes located on the mucosa on the floor of the mouth on either side of the frenulum. In addition U.S. Pat. No. 5,591,216 to Testerman describes a totally implantable device to stimulate the nerves to the genioglossus muscles. In addition, WIPO Patent Application No. 04064729 to Gordon describes a neuroprosthetic device that can be injected into the soft palate to treat snoring. At present these devices have not been clinically proven. In summary, sleep disorders are a significant health problem without an acceptable solution and there is a need in the art for new and more effective therapies.

SUMMARY OF THE INVENTION

While not wishing to be bound by any single theory my studies of human tongue anatomy suggest that episodes of obstruction evolve by a sequence of events (FIGS. 4A-4F). The initial inciting event is the deformation of a relatively small part of the tongue 451. Under certain conditions deformation begins in soft tissue on the top of the tongue 451, particularly in the area of the tongue curve, and specifically near the center line of the tongue curve. As this tissue deforms it narrows the airway and causes more negative pressure thereby causing greater deformation. This feedback cycle in turn deforms enough tissue in the area to cause a complete obstruction in the velopharyngeal area.

If an initial obstruction occurs near the end of inspiration, the obstruction is relieved by an expiration, or by action of the genioglossus muscle. However, if the obstruction occurs at the beginning of inspiration reflexes trigger stronger inspiratory effort that further lowers airway pressure. This increased negative pressure causes deformation and collapse of most of the tongue base 453. At this point the airway is firmly plugged by soft issue and activity of the genioglossus only stretches the tongue tissue that is plugged and cannot dislodge it.

Therefore the tongue curve is the critical area that initiates the cascade leading to obstruction. This relaxed muscle is very flexible and easy to deform, however, the converse is also true, very little force is needed to prevent this deformation. Therefore if sufficient counterforce is exerted at the proper localized area of the tongue 451 it can prevent obstruction without noticeable effects on speech and swallowing movements.

How a device could prevent the deformation and collapse of the tongue curve is not a trivial problem:

This area of the tongue is very mobile during speech and swallowing, therefore the amount of force exerted must be low and highly localized. It is unacceptable to render the area immobile, as would be done if were stiffened by a large implant or scar tissue.

The whole area of the velopharynx has extensive sensory innervation, and relatively minor stimulation there causes either a gag or a swallow.

The tongue base and body have a larger blood supply than comparable muscles elsewhere in the body. Any implant placed in the area has a high probability of causing internal bleeding with potentially catastrophic tongue swelling.

Soft tissue and tongue in particular remodel easily. Specifically sutures or implants that exert force cause the tissue to remodel to relieve that force. This is known as the "cheese cutter" effect. Therefore, the forces applied to the soft tissue and/or tongue must be relatively low and applied for limited periods.

Humans upper airway anatomy is highly variable, and the pathological anatomy of sleep apnea patients is even more variable. Moreover the upper airway anatomy of sleep apnea patients changes over time as the disease progresses or improves.

Finally, OSAS patients have borderline airways that can obstruct after even minor amounts of swelling such as that following surgical manipulation. Therefore it not obvious how a device could both exert force in the area yet avoid swelling.

Moreover to be maximally effective and to get patient and physician acceptance the device would ideally require additional qualities:

It should be capable of being inserted as an outpatient procedure.

Preferably the device could be removed during the day and reinserted by the patient at night.

It would be adjustable to conform to the specific needs of the patient.

It would be comfortable for the patient.

When the device was in place it would not be noticeable to anyone else.

There is a tremendous variability in human upper airway anatomy, and even further variation in the pathological changes contributing to sleep apnea and related disorders. Moreover, the pathological anatomy changes over time in each patient as their condition improves or deteriorates. No single method and device is able to treat all contingencies. Therefore there is a critical need for methods and devices that are optimized for different sites in the upper airway.

Embodiments of the invention include methods and devices to prevent or treat upper airway breathing disorders related to impaired airflow in mammals. These breathing disorders are, without limitation, snoring, upper airway resistance syndrome, and obstructive sleep apnea. In addition, this invention is applicable to airway disorders in animals including but not limited to dorsal displacement of the soft palate in horses and brachycephlic obstructive airway syndrome in certain breeds of dog. Those skilled in the art will readily appreciate that application of this invention can be applied to other conditions of the upper airway.

One aspect of the invention prevents airway obstruction by dilating the airway or preventing the tissue from deforming. It enlarges the airway when excess tissue is present and also counteracts the deforming influence of negative airway pressure on the relaxed soft tissue of upper airway structures. These structures include, without limitation, the tongue, soft palate, pharyngeal walls and supraglottic larynx.

FIGS. 5A-5D, depict one embodiment of a device referred to as a tissue retractor or as a Linguaflex tongue retractor (LTR) (notwithstanding that the use of the device as disclosed herein the tissue retractor or LTR device is not limited to use in the tongue or to use for tissue or tongue retraction). The LTR includes a retractor member (R), a shaft (S), and an anchor member (A). In some embodiments a retractor member (R) is physically coupled to the soft tissue of the tongue base. The shaft (S) passes through the midline of the tongue to connect with an anchor member (A). The anchor member (A) imparts counterforce through the shaft (S) to the retractor member (R), thereby preventing deformation of the soft tissue.

One aspect of this invention describes improvements to the retractor member, shaft and anchor member that increase the efficacy of the device while decreasing patient discomfort. Improvements of the tissue retraction (e.g., the LTR) components include but are not limited to a retractor member with a retractor head that collapses to fit within a narrow delivery device and expands after insertion; a shaft that passively adjusts its length and tension in response to surrounding tongue activity; and a modified anchor that is adjustable by the patient and attaches to a bolster (e.g., a soft bolster), a partially implanted receptacle in the mouth, and/or a dental appliance.

One aspect of the invention is a method of making the implant more comfortable by allowing the device to be under little or no tension during the day, in the "unloaded" state, and to increase the tension to therapeutic levels at night, in the "loaded" state. This loading and unloading method increases the comfort for the patient and allows the patient a large degree of control. The method and the devices that implement the method are of great importance, because the lack of patient compliance is perhaps the largest problem with current sleep apnea therapies. A method and/or device that is comfortable to the patient has an increased likelihood of patient compliance.

Another aspect of this invention is that additional sites in and around the tongue can unexpectedly be treated to prevent airway disorders. Non-limiting examples of these sites are the base of tongue, the mucosa covering the tongue, the tongue frenulum, the pharyngoglossal fold, the palatoglossal fold, the aryepiglottic fold, the lateral pharyngeal wall, and the soft palate. An improved tissue retractor (e.g., an LTR) applied to one or more of these sites directly or indirectly stiffens and displaces tissue and/or mucosa in, for example, the tongue base, the soft palate, and the lateral pharyngeal wall, and enlarges the velopharynx thereby avoiding obstruction of the patient's airway. Each site has specific anatomy and suitable tissue retractors are disclosed for use in various anatomical areas to perform efficiently and with minimal risk and discomfort to the patient.

One aspect of this invention is a tissue retractor (e.g., an LTR) that indirectly retracts tongue base via its implant site in the frenulum area. Placement in the frenulum area simplifies the insertion, adjustment, and maintenance of the device. Another aspect of this invention describes a highly localized and fully implantable tissue retractor (e.g., LTR) that is inserted into the base of tongue to stiffen lax surface mucosa or mechanically couple it to internal tongue structures.

Another aspect of this invention is a tissue retractor (e.g., an LTR) inserted in or around the pharyngoglossal fold. This site allows retraction and stiffening of tongue base tissue as well as the soft palate and lateral pharyngeal wall. The advantage of the pharyngoglossal fold site is its minimal invasiveness, safety and its beneficial effect on multiple different structures.

Another aspect of this invention is a method and device to remodel upper airway tissue in order to enlarge the pharyngeal airspace. Tissues remodeled include but are not limited to tongue base, palatine tonsil, pharyngeal wall, and soft palate. Preferably these tissues are either compressed to decrease their volume, displaced to provide space in other areas, or reshaped. In some embodiments, the tissue remodel effect lasts from months to years after the device(s) have been removed. To achieve this persistent beneficial effect, devices would preferably exert force on the tissue for a time that ranges from about 1 week to about 1 year or from about 1 month to about 6 months.

Another aspect of this invention includes non-invasive methods and devices that reversibly couple to mucosa to grasp, move and/or reposition soft tissue. Suitable non-invasive methods use magnets, adhesives, vacuum, and/or mechanical leverage. In one embodiment a curved retractor member is reversibly inserted into one or more selected sites. In another embodiment indwelling clamps are placed on one or more of the PGF, tonsillar folds, the soft palate and other soft tissue folds. A suitable retractor member can be loaded as needed by coupling the retractor member to a modified anchor inside or outside of the patient's mouth. In still another embodiment, the floor of mouth is protracted to displace the tongue base. In a still further embodiment a vacuum reshapes the tongue to decrease the volume of the tongue in the tongue base. Another aspect of this invention describes tissue retractors (e.g., LTR's) specifically adapted to prevent dorsal displacement of the soft palate in horses.

The tissue retractor (e.g., the LTR) can pass through tissue and have its retractor member and anchor member ends outside of tissue, have only one end outside of tissue and exposed, or the entire device can be implanted. The shaft of the device can pass deeply into tissue, or pass superficially just beneath the mucosa. The retractor member and the anchor member are preferably shaped to fit in a site so as to distribute force evenly. For example, all or a portion of the tissue retractor has a flat shape for placement in flat or mildy curved surfaces such as the mid tongue base, pharyngeal wall, and soft palate. All or a portion of the tissue retractor is wedge shaped for placement at or near the depths of the pharyngoglossal fold and lateral margin of the soft palate. All or a portion of the tissue retractor (e.g., the anchor member) is V shaped for placement at or near the frenulum. All or a portion of the anchor member is T shaped for placement at, near, or through the teeth. The materials used to form the tissue retractor, the implant, the retractor member and/or the anchor member can include any non-reactive biocompatible materials. Suitable non-reactive biocompatible materials are known in the art. Non-limiting examples of suitable rigid materials include stainless steel, titanium, ceramics, and plastics. Non-limiting examples of suitable elastomeric materials include silicon and rubber.

In some embodiments, the force needed to displace the tongue anteriorly or the soft palate superiorly varies from about 0.001 gram to about 10,000 grams, about 0.1 gram to about 1000 grams, or about 10 to about 100 grams. This force could be applied over a time that ranges from about 0.01 seconds to permanently, about one minute to about 1 month, for the duration of sleep, or during episodes of restricted upper airway flow.

BRIEF DESCRIPTION OF THE DRAWINGS

The present invention will be more readily understood from the detailed description of exemplary embodiments presented below considered in conjunction with the attached drawings, of which:

FIGS. 4A-4F illustrate a Mechanism of airway obstruction and the effect of certain therapies;

FIGS. 6A-6E illustrate a Retractor member;

FIGS. 10A-10C illustrate an Anchor member, frenulum area;

FIGS. 13A-13L illustrate Tongue base embodiments;

FIGS. 19A-19F illustrate Soft palate embodiments;

It is to be understood that the attached drawings are for purposes of illustrating the concepts of the invention.

DETAILED DESCRIPTION OF THE PREFERRED EMBODIMENTS

Figure 1:
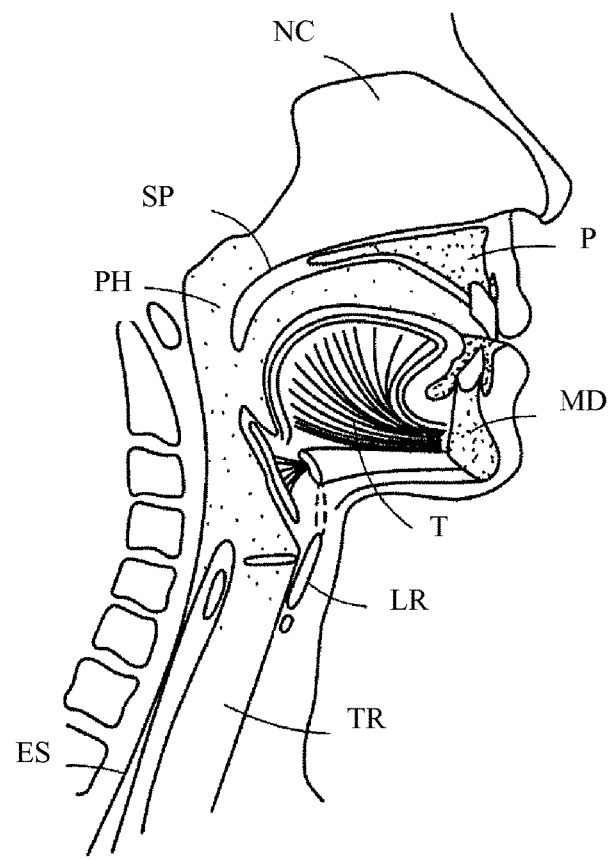
FIG. 1 is a drawing of the human upper airway in the mid sagittal plane.
Figure 2:
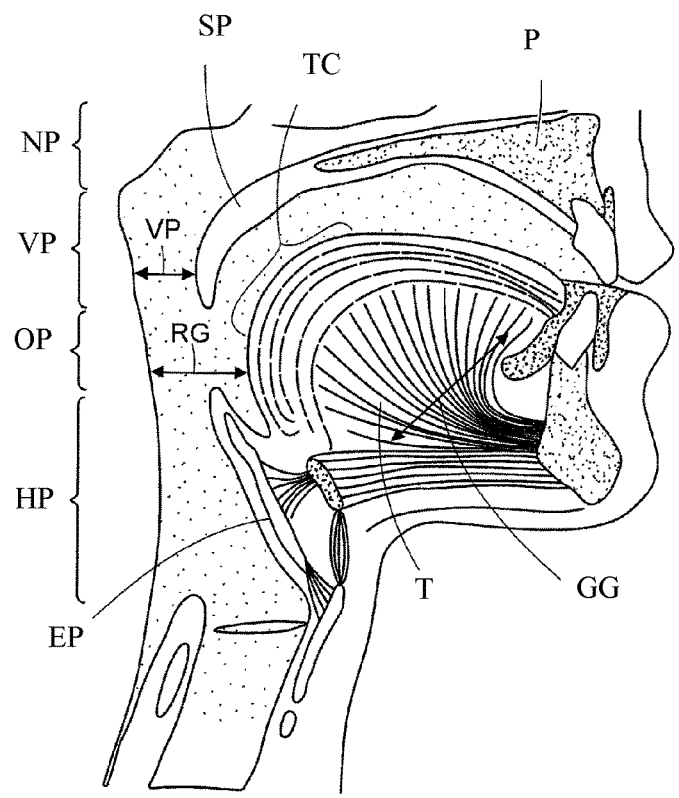
FIG. 2 is a simplified schematic drawing of the areas of the pharynx, the tongue, and surrounding structures.

FIG. 1. Drawing of the human upper airway in the mid sagittal plane.
PH, Pharynx
ES, Esophagus
MD, Mandible
LR, Larynx
TR, Trachea
NC, Nasal Cavity
SP, Soft Palate
P, Hard Palate
T, Tongue FIG. 2. Simplified schematic drawing of the areas of the pharynx, the tongue and surrounding structures
NP, Nasopharynx
VP, Velopharynx
HP, Hypopharynx
SP, Soft palate
P, Hard palate
T, Tongue
GG, Genioglossus muscle
EP, Epiglottis
OP, Oropharynx The areas of the pharynx include the nasopharynx, which spans from the level of the hard palate up, the velopharynx, which spans from the beginning to end of the soft palate, the oropharynx, which spans from the edge of the soft palate to the epiglottis, and the hypo pharynx, which spans form the epiglottis to the esophagus. The velopharyngeal space (VP) is the area between the soft palate and the back wall of the pharynx. The retroglossal space (RG) is the area between the tongue base and the back wall of the pharynx.

Figure 3:
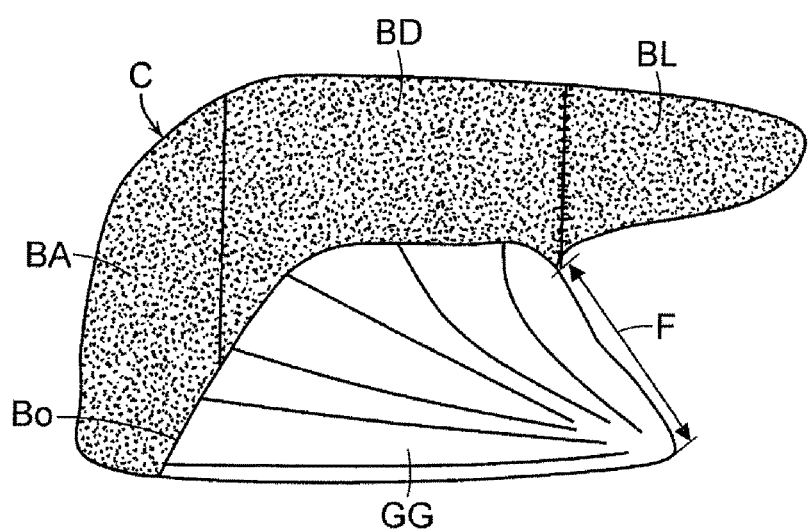
FIG. 3 illustrates Anatomical landmarks of the tongue.
Figure 5A:
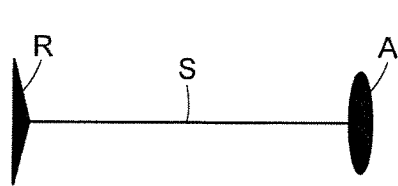
FIGS. 5A-5D illustrate an Embodiment of an LTR device.
Figure 5B:
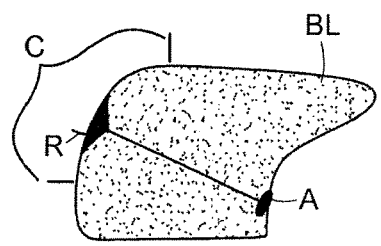
Figure 5C:
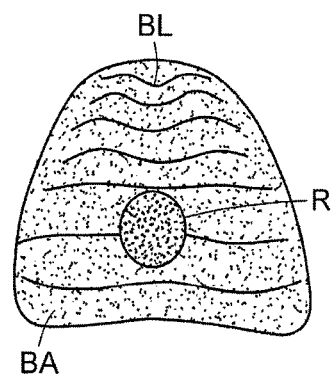
Figure 5D:
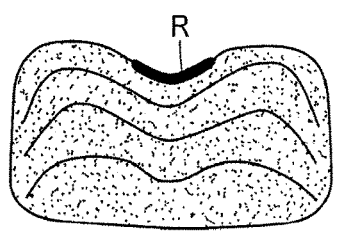

FIG. 3. Anatomical landmarks of the tongue. The tongue will be defined as the grey area of this schematic. From front to back the tongue is divided into a blade, body, and base. The genioglossus muscle (GG) inserts into a connective tissue boundary on the undersurface of the tongue (Bo). The entire region of the genioglossus muscle and its mucosa is referred to as the "frenulum area".
BA) Tongue base
BD) Tongue body
BL) Tongue blade
Bo) Boundary between tongue and genioglossus
C) Tongue curve
F) Frenulum
GG) Genioglossus muscle FIG. 4. Mechanism of airway obstruction and the effect of current therapies.

4A. Shows the normal tone in a tongue 451 while a patient is awake. The tongue 451 remains in position allowing the airway to remain open. The arrow 469 shows airflow through the airway, the small arrow 412 shows the relationship of pharyngeal wall 465 to the mandible 468.

4B. Sleep Apnea. During sleep muscle tone is lost in the tongue 451 and the tongue 451 becomes flaccid. Negative pressure in the pharynx during inspiration causes backward collapse of the tongue 451 in the velopharyngeal area, because the airway is narrowest at that point and the tongue curve (circle) is most deformable.

4C. Sleep Apnea. After the airway obstructs airflow 469 at the velopharyngeal area inspiration lowers the pressure in the pharynx further causing the base 453 of tongue 451 to deform and firmly block the airway.

4D. CPAP works by pumping air 416 at high pressure through the patient's nose, thereby splinting the pharynx open.

4E. Dental devices work by moving the entire jaw forward. Depicted is the impact of the dental device on the patient's mouth, but not the dental device itself. As the tongue 451 is attached to the soft tissues along the floor of the mouth, and they attach to the jaw, the tongue 451 is indirectly moved to expand the airway. Note that the jaw has moved in relation to the pharyngeal wall 465.

4F. The tissue retractor 401 (e.g., an LTR) prevents posterior deformation of tongue 451 curve by directly restraining the tongue 451 curve from moving backwards.

FIG. 5. Embodiment of the tissue retractor (e.g., an LTR) device. Shown is one embodiment of the LTR.

5A. The LTR has three main components: a retractor member (R), a shaft (S), and an anchor member (A).

5B. Side view of the tissue retractor (e.g., an LTR) inserted in a tongue.

5C. Back view of tongue curve showing retractor position.

5D. Back view of tongue base showing the curved midline shape taken from the posterior aspect of the tongue.

FIG. 6A-6E. Retractor member. This figure illustrates a retractor component of a tissue retractor 601 (e.g., an LTR) that can be mounted on a needle 635 for implantation within upper airway tissue 650 and deploys when the needle 635 is withdrawn. The retractor member 620 is shown as an integral component of the shaft 610 and is molded as one piece from soft elastomeric material.

6A. Four views, two side views and two front views of the retractor member 620 head. The plane of the retractor member 620 head rests at about 15° relative to the shaft 610.

6B. Side view of retractor member 620 head mounted within a needle 635. A part of the retractor member 620 head lays on the outer surface of the needle 635.

6C. Side view of needle 635 passing through tissue 650. Note that the retractor member 620 head lays flat against the needle 635 barrel and does not interfere with passage of the needle 635 through tissue 650.

6D. After the needle 635 penetrates mucosa enough to clear the tissue 650 the retractor member 620 head again extends away from the shaft 610 such that the retractor member 620 head rests at about 15° relative to the shaft 610.

6E. Slight traction on the shaft 610 causes the retractor head 620 to catch the mucosa and/or tissue 650 and come to rest in its working position.

FIG. 7. Shaft member 710. Shown is an improvement to the shaft of a tissue retractor 701 (e.g., an LTR) that maintains its retractor tension when the tongue 751 is relaxed, such as during sleep. However, during speech and swallowing, when the tongue base often moves backward, the activity of the tongue 751 squeezes the shaft 710 and thereby lengthens it. In this way there is little or no resistance to the normal tongue 751 movements.

7A. Schematic view of LTR in the tongue 751 with normal muscle tone. Note that the retractor member 720 head lays on the mucosal surface of the tongue base without indenting it.

7B. During sleep the tongue 751 loses all tone and tends to flop backward into the airway. The retractor member 720 head then resists this deformation.

7C. During swallowing and speech the tongue base sometimes moves backward. During these movements there is a strong contraction of the tongue muscles. This contraction squeezes the upper shaft 711, this in turn causes the shaft 710 to lengthen and move the tissue retractor 701.

FIG. 8. Anchor member 830, bolster 840

8A. Front view 842 of bolster 840.

8B. Top view 844 of bolster 840.

8C. Side view 846 of bolster 840.

8D. Side view of tongue 851 with unloaded tissue retractor 801 (e.g., LTR).

8E. The anchor member 830 and the shaft 810 are pulled forward and a portion of the shaft 810 is slotted into the cleft 848 on underside of the bolster 840.

8F. Bolster 840 in position under tongue 851.

8G. Close up view of tissue retractor (e.g., LTR) anchor member 830 sitting in the recess (i.e., the cleft 848) of the bolster 842.

8H. Top view of tongue 851 with a tissue retractor 801 (e.g., LTR) retractor member 820 and a bolster.

FIG. 9. Anchor member, dental

9A. Shows a modified anchor that is reversibly attached to the upper or lower front teeth. The anchor member 930 (A) interfaces with the teeth, the shaft 910 (S) connects to retractor/coupler 920 (R/C). The retractor/coupler either has a retractor member 920 that interfaces with tissue, or a coupler component that connects to an implanted retractor, shaft, or anchor member of an implanted tissue retractor (e.g., an LTR).

9AA. Shows a side view of the anchor member 930 (A) the anchor member 930 has depth that is wide, the shaft 910 and the retractor member 920 are also depicted.

9B. Drawing of top view of tongue 951 and mandible 968 with a tissue retractor 901 (e.g., an LTR) implanted from the tongue base 953 to the frenulum. The anchor 930 of the LTR can be reversibly attached to the R/C component 920 of the dental anchor.

9C. Another embodiment of a tissue retractor 901 having a modified anchor member 930 for use on the lateral teeth 998.

9D. Top view of tongue 951 and mandible 968 with a lateral dental anchor member 930. The anchor member 930 attaches to the molar tooth 998, the shaft 910 passes through or over the pharyngoglossal fold 967, and the retractor rests 920 against the posterior surface of the fold.

9E. A palatal prosthesis 972 provides an anchor member 930 with some possible coupling extensions for retraction or protraction of surrounding structures including the soft palate 966, the PGF 967, the floor of mouth 976, and the tongue 951 surface (couples at the tongue surface at, for example, a tongue stud.

FIG. 10. Anchor member, frenulum area.

Within the genioglossus muscle 1063 are small tendons upon which muscle fibers insert at various angles. The main tendon is in the middle of the muscle and smaller tendons branch off at various points. Preferably an anchor 1031 is inserted in the frenulum area 1060 such that the implanted portion of the anchor 1031 passes through a tendon. However, the anchor 1031 can be inserted into any spot in the frenulum area 1060 or inserted into soft tissue attached to the mandible 1068. The anchor 1031 could be coupled to a tissue retractor (e.g., an LTR) by a variety of mechanisms as described herein.

10A. Photograph of the side view of the tongue 1051 and mandible 1068 cut in the centerline (mid-sagittal plane).

10B. Drawing of the photograph of the side view of the tongue 1051 depicted in FIG. 10A.

10C. Close up of the frenulum area 1060 an anchor (A) 1031 is inserted into the frenulum 1060.

FIG. 11. Frenulum area embodiment.

11A. Photograph of the side view of the tongue 1151 and mandible 1168 cut at the centerline. The frenulum 1160 is the front edge of the genioglossus muscle 1163, frenulum area 1160 refers to the entire genioglossus 1163 and surrounding mucosa. The front and rear boundaries of the genioglossus muscle 1163 are marked by solid lines. The genioglossus muscle 1163 attaches to a small area on the inner surface of the mandible 1168 and tendinous extensions from that area. It fans out from these attachments to insert mostly into connective tissue along the length of the body and base of the tongue 1151 called the boundary layer 1161.

11B. Drawing of the photograph of the side view of the tongue 1151 depicted in FIG. 11A.

11C. Shown is a tissue retractor 1101 (i.e., an LTR) passing through the frenulum area 1160 and anchored externally to a dental anchor. The dental anchor can be, for example, a tooth (located in the region of the mandible 1168) over which the tissue retractor 1101 is looped. The implanted part of the LTR 1101 exerts anterior forces on the genioglossus 1163 muscle fascicles 1164 and this is conveyed to the boundary layer 1161 and finally to the tongue 1151 base (arrow/1153). The arrow 1153 shows the direction of force and the displacement from the tongue base to the boundary by the retractor pulling the frenulum area 1160 anteriorly.

11D. Shown is an LTR 1101 passing through the boundary layer 1161 and anchored to a modified anchor 1131 (e.g., a frenulum anchor). Displacement of the tongue 1151 is marked by the arrow.

11E. Shown is a fully implanted LTR 1101 in the frenulum area 1160 connecting the boundary area 1161 in two places. Note that the beneficial retraction of the tongue base 1153 causes some retraction of the tongue blade 1152, however, this retraction of the tongue blade 1152 does not interfere with tongue 1151 function.

FIG. 12. Tongue base implant.

12A. Photograph of a frontal section of tongue 1251 base.

12B. Drawing of 12A. Light lines are the connective tissue of the tongue superior layer (SL) 1258 and the midline septum (MS) 1255. The middle layer (ML) 1254 is the volume of the tongue 1251 beneath the (SL) 1258.

12C. Position of tissue retractor 1201 (e.g, an LTR) implant connecting SL 1258 and ML 1254.

12D. Photograph of the tongue 1251 seen in mid-sagittal plane. Oval marks the area of mechanical decoupling.

12E. Schematic drawing of the portion of the tongue 1251 in the box marked in the photograph shown in FIG. 12D.

12F. Position of tissue retractor 1201 implant.

FIG. 13. Tongue base embodiments

13A. Lateral (left) and top (right) drawings of the tongue 1351 with a tissue retractor 1301 (e.g., an LTR) in which a retractor member 1320 and an anchor member 1330 are connected by a shaft 1310 passing underneath the tongue base mucosa. Shown are an anchor member 1330, a retractor member 1320, and a shaft 1310 that connects the anchor member 1330 and the retractor member 1320. The shaft 1310 is shown as a dotted line when implanted in the soft tissue 1350, e.g., the tongue 1351. The shaft 1310 is shown as a solid line when it is outside soft tissue 1350 (see, FIG. 13D, for example). The arrow 1313 shows the direction of retraction when the retractor member 1320, the shaft 1310, and the anchor member 1330 interact to exert a pressure on at least a portion of the soft tissue 1350.

13B. Lateral (left) and top (right) drawings of the tongue 1351 with a tissue retractor 1301 (e.g., an LTR) with the shaft 1310 taking a more direct route through the tongue 1351 between a retractor member 1320 and an anchor member 1330.

13C. Lateral (left) and top (right) drawings of the tongue 1351 with a tissue retractor 1301 (e.g., an LTR) with the shaft 1310 exiting from mucosa close to the retractor member 1320 and connected to the anchor member 1330. Portions of the shaft 1310 closes to the retractor member 1320 and the anchor member 1330 are beneath the mucosa and other portions of the shaft 1310 are exterior to the tongue 1351.

13D. Lateral (left) and top (right) drawings of the tongue 1351 with a tissue retractor 1301 having an implanted anchor member 1330, an implanted retractor member 1320 and a reversible attachable shaft 1310.

13E. A lateral view of a partially implantable retractor member 1320, which has a first portion 1321 implanted in soft tissue 1350 and a second portion 1322 external to the soft tissue 1350. An anchor member 1330 could likewise be partially implantable.

13F. A top view of a partially implantable retractor member 1320.

13G. A lateral view of a partially implantable retractor member 1320 showing the shaft 1310 connecting to the second portion 1322 of the retractor member 1320, and the second portion 1322 is exterior to the soft tissue 1350.

13H. A lateral view of a partially implantable retractor member 1320 with the second portion 1322 extension depressed such that the second portion 1322 is substantially flush with soft tissue 1350 mucosa when the retractor member 1320 is not in use.

13I. Lateral (left) and top (right) drawings of tongue 1351 with a tissue retractor 1301 (e.g., an LTR) with an elastic sleeve or a band 1370 placed over the tongue blade and a shaft 1310 connecting to a partially implanted retractor member 1320. The arrow 1313 shows the direction of force and tongue base displacement.

13J. Lateral (left) and top (right) drawings of a tongue 1351 with a tissue retractor 1301 (e.g., an LTR) anchored by an anchor member 1330 in each PGF 1357 and a shaft 1310 passing across the tongue 1351 base and contacting at portion of a partially implanted retractor member 1320.

13K. Lateral (left) and top (right) drawings of a tongue 1351 with a first tissue retractor 1301*a* (e.g., an LTR) anchored beneath the tongue blade 1352 by a first anchor member 1330*a*, a first shaft 1310*a* passes through the tongue blade to a first retractor member 1320*a*. The first retractor member 1320*a* acts as a modified anchor member, which is the second anchor member 1330*b* on the superior surface of the tongue 1351. A second shaft 1310*b* passes posteriorly to a semi implanted second retractor member 1320*b*. At portion of the semi implanted second retractor member 1320*b* is implanted in the tongue 1351. The use of a first tissue retractor 1301*a* allows adjustment of tension of the second tissue retractor 1301*b* from the anchor site of the anchor member 1330*a* located beneath the tongue blade 1352.

13L. Lateral drawing of a tongue 1351 with a tissue retractor 1301 includes a rigid shaft 1310 that connects an anchor member 1330 below the tongue blade 1352 to a retractor member 1320 above the tongue blade 1352.

13M. Lateral drawing of a tongue with a sleeve (e.g., a band 1370) reversibly placed over the tongue blade 1352 and the tissue retractor 1301 shown in FIG. 13L is rotated forward by the band 1370. The band 1370 pushes and rotates the retractor member 1320 forward and pushes the anchor member 1330 forward. The counterforce that allows pushing of the tissue retractor 1301 comes from resistance of the tongue 1351 being compressed by the band 1370.

FIG. 14. The Superior Pharyngoglossal Fold (PGF).

14A. Side view of the upper airway showing the area of the tongue where the PGF inserts (PGFI). A smaller superior region is of particular significance as it receives overlapping insertions of muscles connecting to the soft palate and lateral pharyngeal walls (PHW), including but not limited to the palatoglossus and superior pharyngeal constrictor muscles.

14B. Side view of tongue in relation to mandible with the area of superior PGF attachment marked.

14C. The palatoglossus muscle (PA) is shown connecting the soft palate to the superior PGF.

14D. The superior pharyngeal constrictor muscle (SPHC) connects the pharyngeal walls to the superior PGF.

14E. Schematic showing that retraction force (RF) of the PGF is dispersed to the tongue base, soft palate, and lateral pharyngeal walls (PHW).

FIG. 15. Pharyngoglossal Fold embodiments

15A. Drawing showing the posterior collapse of the tongue 1551 and its effects on airflow 1569 through the airway.

15B. A retractor member 1520 at the PGF 1557 (i.e., the first PGF) and a shaft 1510 that passes across the frenulum 1560 to a retractor in the other PGF (i.e., the second PGF). The shaft 1510 can pass anteriorly to a dental anchor or other anchor in the patient's oral cavity.

15C. A retractor member 1520 in the PGF 1557 and a shaft 1510 passing through the tongue 1551 tissue to emerge and connect to a modified anchor 1531. An alternative embodiment shows the retractor member 1520 in the PGF 1557 passes through the tongue 1551 tissue through the floor of the mouth 1576 to an external anchor 1532 resting on the skin 1590.

15D. An implanted tissue retractor 1501 (e.g., an LTR) with a retractor member 1520 in or near the PGF 1557 and a shaft 1510 passing through tongue 1551 to an anchor member implanted in the genioglossus muscle or an anchor member implanted in structures located in or at the floor of the mouth 1576.

15E. A tissue retractor 1501 (e.g., an LTR) with a retractor member 1520 in the superior PGF 1557a and an anchor member 1530 in the inferior PGF 1557b. Arrow 1513 shows the inferior displacement of the tongue base 1553.

15F. A retractor member 1520 in the PGF 1557 and a shaft 1510 passing through the tongue 1551 to an anchor member 1530 on the superior surface of the tongue 1551.

FIG. 16. Pharyngoglossal Fold embodiments.

16A. A retractor member 1620 at the tongue base 1653 is connected by two sub-mucosal shafts 1610 to anchor members 1630 disposed in front of each PGF 1657.

16B. A sub-mucosal shaft 1610 connects two anchor members 1630 each anchor member 1630 is in front of each PGF 1657.

16C. Two implanted anchor members 1630 are in or near the PGFs 1657 and the first anchor member 1630 is connected to the second anchor member 1630 by a sub-mucosal shaft 1610.

16D. Magnets 1691 implanted in or near each PGF 1657 are connected by a sub-mucosal shaft 1610. The tissue retractor is "loaded" by exposing the implanted magnets 1691 to an external magnet that is attracted to the magnets 1691.

16E. Two figures on the left show a magnet 1691 implanted in a PGF 1657 is retracted by a magnet of opposite polarity attached to a modified anchor. Two figures on the right show a magnet 1691 enclosed in an implant that has two flanges to keep the implant in place within the PGF 1657.

16F. Left, a schematic of a tissue retractor 1601 that has an anchor member 1630 that can be a dental type modified anchor. The anchor member 1630 is a clasp that reversibly attaches to teeth 1698 as shown on right. A shaft 1610 of variable length attaches to a retractor member 1620 or to a coupling mechanism that in turn connects to an implanted retractor member. The implanted retractor member may be a magnet or mechanical mechanism. Right, Drawing of tongue 1651 and mandible 1668 seen from above. Two embodiments of the dental modified anchor are shown: in the bottom embodiment, the retractor member is a magnet that couples to an implanted magnet as shown in the two figures on the left of FIG. 16E; in the top embodiment, the shaft ends with a magnet that couples to a reversible magnetic implant as shown in the two figures on the right of FIG. 16E FIG. 17. Soft Palate embodiments.

17A. View of the mouth showing the soft palate (SP), palatoglossal folds (PAF), (Henry Gray. Anatomy of the Human Body. 1918) and Tongue Gag Area (TGA).

17B. Same view as FIG. 17A but with mucosa removed showing the underlying muscles (palatoglossus muscle, PA; palatopharyngeus muscle, PAPH) (right side) and the nerve and blood supply (left side).

17C. View of the left lateral pharyngeal wall area after mid-sagittal section of FIG. 17B. The tongue is retracted inferiorly.

Four positions for placement of tissue retractors are shown, in each of the four positions an anchor member 1730 is positioned in the superior PGF:

Position 1) the shaft passes next to palatoglossus muscle around the tonsil (TN), the retractor rest against lateral edge of soft palate. This embodiment increases the lateral velopharyngeal area.

Position 2) the shaft travels within the palatoglossus muscle, the retractor is near the midline soft palate. This embodiment increases medial velopharyngeal airspace.

Position 3) the shaft passes through the palatoglossus muscle, the palatine tonsil, and the palatopharyngeus muscle, the retractor rests against the posterior wall of the soft palate. This embodiment compresses and permanently remodels the palatine tonsil.

Position 4) the shaft passes 1 cm under the tongue base mucosa and the retractor rests against tongue base. This position of tissue retractor placement can be employed for tensing the tongue base.

FIG. 18. Tonsillar Fold embodiments

18A. The tissue retractor 1801 has a retractor member 1820 on the posterior surface of posterior tonsillar fold, at least a portion of the shaft 1810 is inside the tissue of the soft palate, the anchor member 1830 is on the anterior surface of anterior tonsillar fold. This is employed for compression of the palatine tonsil.

18B. A retractor member 1820 in the superior Palatoglossus fold and an anchor member 1830 in the inferior Palatoglossus Fold or PGF.

18C. The tissue retractor 1801 is implanted within the palatoglossus muscle.

18D. The anchor member 1830 at lateral aspect of soft palate, at least a portion of the shaft 1810 is inside the tissue of the soft palate, the retractor member 1820 midline of the soft palate.

18E. The tissue retractor 1801 retractor member 1820 is on the inner surface of the palatoglossal fold and the anchor member 1830 is a modified dental anchor that couples to a patient's tooth 1898.

18F. The tissue retractor 1801 retractor member 1820 is posterior the tonsillar fold, at least a portion of the shaft 1810 is inside the tissue of the soft palate, and the anchor member 1830 is anterior the tonsillar fold.

FIG. 19. Soft palate embodiments

19A. Top (left) and lateral (right) drawings of the soft palate the anchor member 1930 is in the superior pharyngeal side 19661 and the retractor member 1920 is in the inferior oral side 19662.

19B. Top (left) and lateral (right) drawings of the soft palate the retractor member 1920 is in the superior oral side 19662 and the anchor member 1930 is in the inferior pharyngeal side 19661.

19C. Top (left) and lateral (right) drawings of the soft palate. A bolster 1940 is added in front of the anchor member 1930 to load the tissue retractor 1901. Note the indentation and rotation of the soft palate 1966.

19D. Top (left) and lateral (right) drawings of the soft palate. A tissue retractor 1901 is totally implanted in the soft palate 1966.

19E. Top (left) and lateral (right) drawings of the soft palate. A retractor member 1920 and an opposing anchor member 1930 are disposed through the soft palate 1966.

19F. Top (left) and lateral (right) drawings of the soft palate. The tissue retractor 1901 provides an attachment for retainers (e.g., one or more bands 1970) that lift edge of soft palate 1966.

FIG. 20. Veterinarian embodiments—Shown are embodiments of this invention for equine dorsal displacement of the soft palate 2066.

20A. Normal configuration of the horse upper airway during exercise. Note that the soft palate 2066 overlaps and interlocks the epiglottis 2063 of the larynx to provide an open conduit for airflow 2069.

20B. In dorsal displacement of the soft palate (DDSP) in horses the soft palate 2066 is dislodged from its locked position and obstructs the airway from airflow 2069. This is believed to be caused by the backward movement of the tongue base 2053.

20C. An embodiment of a tissue retractor 2001 (i.e., an LTR) for this condition. The shaft 2010 reaches through the mandible 2068 to an adjustable anchor member 2030 in front of the mandible 2068.

20D. Another embodiment where the shaft 2010 connects to an anchor member 2030 on the tongue 2051 surface which is reversibly attached to the bit 2067 of a bridle during exercise.

20E. An embodiment that employs a tissue retractor 2001 to directly oppose dislodging the soft palate 2066 from its normal position. An anchor member 2030 in front of the soft palate 2066 passes backward and then through the epiglottis 2063 to a retractor member 2020 on the laryngeal surface of the epiglottis 2063.

20F. Another view of the of the soft palate 2066 and epiglottis 2063 employing the tissue retractor 2001 depicted in FIG. 20E.

20G. In an alternative embodiment a tissue retractor 2001*b*, 2001*c* (e.g., an LTR) passes from the PGF's 2057 to the lateral aspect of the soft palate 2066. The view is from the front and the tongue 2051 is transparent. For comparison, the midline embodiment described in FIG. 20E is also shown with the anchor member 2030 of the tissue retractor 2001*a* in the soft palate 2066.

Figures 21A, 21B:
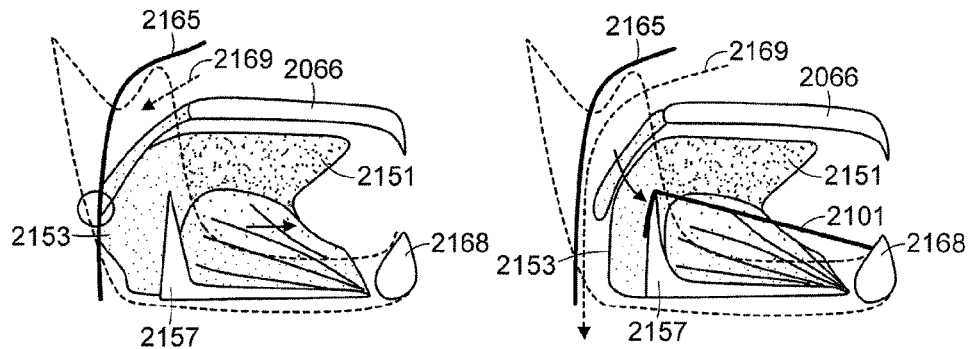
FIGS. 21A-21G illustrate a Non-invasive PGF retractor.

FIG. 21. Non-invasive PGF retractor

21A. Schematic of airway obstruction to airflow 2169 due to backward collapse of the tongue 2151.

21B. PGF 2157 retraction employs a soft "hook" that retracts the PGF 2157 forward and thereby retracts the base 2153 of the tongue 2151, the soft palate 2166 and the pharyngeal walls 2165.

21C. Close up view of a portion of a "hook" shaped retractor member 2120.

21D. Close up view of a clamp 2193 that remains in place surrounding the PGF 2157 by compressing the soft tissue of the PGF 2157 with its arms. The clamp 2193 would always be available for hooking up with, for example, a shaft and because it stays in position it would avoid causing the gag reflex each time it is placed.

21E. An embodiment of a clamp 2193 surrounding the PGF 2157 where compression is performed by two magnets 2191, 2192 of opposing polarity.

21F. Embodiment from 21E where the clamp's 2193 magnets 2191, 2192 are also used to couple to a shaft 2110A where the clamp 2193 acts as a retractor member 2030 that is attached by the shaft 2110A to a modified anchor.

21G. Drawing of two tissue retractors 2101 reversibly placed in a patient's mouth and the effect of the two tissue retractors 2101 on the tongue base 2153 (dotted line).

21H. Close-up view of a tissue retractor 2101 having a hook shaped anchor member 2130.

FIG. 22. Non-invasive retraction, clip embodiment.

22A. Side view of clamp 2293 on soft tissue fold. One method of reversibly attaching to the fold is to compress the tissue by the ends of the clamp 2293.

22B. Side view of a clamp 2293 having magnets 2291, 2292 of opposite polarity. The magnets attraction provides sufficient force for a stable clamp 2293 position and a shaft is unnecessary to maintain the clamp 2293 in position on the mucosal fold 2259.

22C. Front view of clamp 2293 on a soft tissue fold. The shaft 2210 connection between the arms of the clamp 2293 can serve to retract the edge of the mucosal fold 2259.

22D. Two clamps 2293A, 2293B are used to provide protraction (lengthening) of tissue, protraction can have a useful effect on structures that benefit from stiffening such as the soft palate and the tongue base.

22E. A clamp 2293 on anterior tonsillar pillar attached via a shaft 2210 to a dental anchor 2230 that is reversibly anchored to a tooth 2298.

22F. A clamp 2293 on posterior tonsillar pillar attached via a shaft 2210 to a dental anchor 2230 that is reversibly anchored to a tooth 2298.

22G. A clamp 2293 on the edge of soft palate attached via a shaft 2210 to a dental anchor 2230 that is reversibly anchored to a tooth 2298.

22H. Two clamps 2293A, 2293B attached by a shaft 2210C that retract the pharyngeal wall toward the aryepiglottic fold, thus stiffening the lateral pharyngeal wall.

FIG. 23. Non-invasive protraction and vacuum: Floor of Mouth Depression

23A. Side view. Floor of mouth 2376 is marked by a checkered pattern that extends from the mandible 2368 to the hyoid bone 2377.

23B. Front view. Floor of mouth 2376 connects to the bottom of each side of the mandible 2398.

23C. Top view. Tongue 2351 is transparent and triangular root 2349 of tongue can be seen. The anterior extension of the root 2349 is the genioglossus muscle 2363 (seen in FIGS. 23A and 23B) insertion into the mandible 2398.

23D. A bolster 2340 is pushed downward and slightly anterior by a shaft 2310 exerting a protracting force. Note the indentation of the floor of mouth 2376 and the altered position of the tongue 2351 and the PGF 2357.

23E. The floor of mouth 2376 is depression by the bolster 2340 is reflected by decreased height of tongue 2351 surface.

23F. The bolster 2340 is seen from above. Note the anterior displacement of the base of the tongue 2351.

23G. Side view. A vacuum device 2347 is a retractor member 2320 applied to the lateral tongue 2351. The vacuum device 2347 is positioned below the tongue 2351 adjacent the floor of mouth 2376 and the PGF 2357.

23H. Front view. A vacuum device 2347 is employed as a retractor member 2320 that displaces tongue 2351 tissue. Tongue 2351 tissue displacement is reflected by the decreased height of the tongue 2351 surface.

23I. Top view. A vacuum device 2347 is employed as a retractor member 2320 that displaces tongue 2351 tissue resulting in anterior displacement of the base of the tongue 2351 that avoids obstruction of the airway due to collapse of the tongue 2351 toward the soft palate 2366 (see FIG. 23G).

23J. A view of another vacuum device 2347 employed as a tissue retractor.

23K. A close up view of the vacuum device 2347 of FIG. 23J employed as a tissue retractor.

23L. A close up view of the vacuum device 2347 of FIG. 23K employed as a tissue retractor.

23M. A close up view of another embodiment of a vacuum device 2347.

23N. A close up view of another embodiment of a vacuum device 2347.

The term "subject" as used herein includes animals of mammalian origin, including humans. Anatomical terminology used to describe position and orientation as used herein can best be defined by the following description:

When referring to animals, that typically have one end with a head and mouth, with the opposite end often having the anus and tail, the head end is referred to as the cranial end, while the tail end is referred to as the caudal end. Within the head itself, rostral refers to the direction toward the end of the nose, and caudal is used to refer to the tail direction. The surface or side of an animal's body that is normally oriented upwards, away from the pull of gravity, is the dorsal side; the opposite side, typically the one closest to the ground when walking on all legs, swimming or flying, is the ventral side. On the limbs or other appendages, a point closer to the main body is "proximal"; a point farther away is "distal". Three basic reference planes are used in zoological anatomy. A "sagittal" plane divides the body into left and right portions. The "mid-sagittal" plane is in the midline, i.e. it would pass through midline structures such as the spine, and all other sagittal planes are parallel to it. A "coronal" plane divides the body into dorsal and ventral portions. A "transverse" plane divides the body into cranial and caudal portions.

When referring to humans, the body and its parts are always described using the assumption that the body is standing upright. Portions of the body which are closer to the head end are "superior" (corresponding to cranial in animals), while those farther away are "inferior" (corresponding to caudal in animals). Objects near the front of the body are referred to as "anterior" (corresponding to ventral in animals); those near the rear of the body are referred to as "posterior" (corresponding to dorsal in animals). A transverse, axial, or horizontal plane is an X-Y plane, parallel to the ground, which separates the superior/head from the inferior/feet. A coronal or frontal plane is an Y-Z plane, perpendicular to the ground, which separates the anterior from the posterior. A sagittal plane is an X-Z plane, perpendicular to the ground and to the coronal plane, which separates left from right. The mid-sagittal plane is the specific sagittal plane that is exactly in the middle of the body.

Structures near the midline are called medial and those near the sides of animals are called lateral. Therefore, medial structures are closer to the mid-sagittal plane, lateral structures are further from the mid-sagittal plane. Structures in the midline of the body are median. For example, the tip of a human subject's nose is in the median line.

Ipsilateral means on the same side, contralateral means on the other side and bilateral means on both sides. Structures that are close to the center of the body are proximal or central, while ones more distant are distal or peripheral. For example, the hands are at the distal end of the arms, while the shoulders are at the proximal ends.

DEFINITIONS

"Anchor" refers to a component of the device that mechanically couples to a site that is substantially immobile or substantially fixed relative to the retractor.

"Deformation" refers to an abnormal change in the shape of upper airway soft tissue structures. This deformation can be due to negative pressure acting on relaxed upper airway structures during sleep causing them to narrow the upper airway. Most preferably this soft tissue can be the tongue curve.

"Frenulum" refers to the vertical anterior edge of the genioglossus muscle. The frenulum passes from the floor of the mouth up to the centerline of the underside of the tongue. The frenulum marks the boundary between the tongue blade and tongue body.

"Frenulum area" refers to the genioglossus muscle and its surrounding mucosa.

"Loaded" refers to a tissue retractor (e.g., an LTR) that can have its tension adjusted such that it has minimal tension during the waking hours (e.g., "Unloaded") and higher therapeutic levels of tension during the sleeping hours (e.g., "Loaded"). The loaded configuration corresponds to the higher therapeutic levels.

"Modified anchor" is an additional component that allows attachment of the permanent anchor of the tissue retractor. In some embodiments the modified anchor allows the patient to adjust tension in the tissue retractor, specifically to increase tissue retractor tension during the sleeping hours (e.g., at night) and to reduce tissue retractor tension during the waking hours (e.g., during the day).

"Palate retractor" refers to a complete device used for the prevention of soft palate deformation.

"Permanent anchor" refers to an anchor component of a tissue retractor that remains on the tissue retractor for the duration of the implantation. In some embodiments, the permanent anchor prevents the anterior end of the shaft from slipping back into tissue (e.g., tongue tissue). In certain embodiments the permanent anchor also serves to connect to a "modified anchor" when a modified anchor is used.

"Pharyngeal wall retractor" refers to a complete device for the prevention of pharyngeal wall deformation.

"Protract" means to lengthen or push apart.

"Reverse deformation" refers to a change in soft tissue shape caused by the tissue retractor. In some embodiments reverse deformation refers to restoring a deformed structure to its normal shape. In other embodiments reverse deformation refers to an indentation of soft tissue in a given area due to the action of a tissue retractor.

"Sleep breathing disorders" refers to all breathing disorders occurring during sleep including but not limited to obstructive sleep apnea, obstructive sleep apnea syndrome, upper airway resistance syndrome, and snoring.

"Tongue base" refers to the part of the tongue posterior to the tongue curve. In anatomical terms the line of demarcation of the tongue base is the circumvalatte papillae, a grossly visible line of raised taste organs on the superior surface of the tongue.

"Tongue blade" refers to the part of the tongue anterior to the frenulum. It is covered by mucosa on its top, sides and undersurface.

"Tongue body" is the mid part of the tongue located between the tongue blade and tongue base.

"Tongue boundary" or "boundary" is the inferior surface of the tongue body and base. The genioglossus muscle inserts onto a large part of the boundary.

"Tongue curve" refers to the area of the tongue where its superior surface curves from a horizontal orientation (tongue body and blade) to a vertical orientation (tongue base). Preferably tongue curve refers to the soft tissue in this area between the mucosal covering of the tongue and the connective tissue boundary where the genioglossus muscle attaches.

"Tongue retractor" refers to a complete device used for the prevention of tongue deformation. In some embodiments it includes a retractor connected to a shaft which in turn is connected to an anchor.

"Laryngeal retractor" refers to a complete device for the prevention of laryngeal soft tissue deformation.

"Retractor" or "retractor head" or "retractor member" refers to a part of an overall tissue retractor. The retractor physically interacts with soft tissue, either directly or indirectly, to prevent it from deforming. In certain embodiments the retractor head is a disc located on an external surface of the tongue, in other embodiments the retractor head is an inflatable balloon, in other embodiments the retractor head may have curved parts that act like hooks, in other embodiments the retractor head may be a flexible wire passing through the tissue, or in some embodiments the retractor is totally implanted within tissue.

"Shaft" refers to that part of the tissue retractor that attaches to the retractor head (e.g. the retractor member) and serves to connect it to the anchor member. The shaft may be one or more of rigid, flexible, solid, hollow, one piece, or multiple linked pieces.

"Unloaded" refers to a tissue retractor that exerts little or no tension. This is usually meant as the configuration during the waking hours (e.g., during the day). In comparison, the tissue retractor is loaded to therapeutic levels during the sleeping hours (e.g., a night).

EXAMPLES

1. Retractor Member (FIG. 6)

Disclosed here, referring to FIG. 6A, is a tissue retractor 601, which includes a retractor member (i.e., the retractor head 620), a shaft 610, and an anchor member. One end of the shaft 610 connects to the retractor member 620 and the other end of the shaft 610 connects to an anchor member (not shown). Referring to FIGS. 6B-6E, the tissue retractor 601 retractor member 620 is inserted into a tissue 650 by a needle 635 and the tissue retractor 601 automatically deploys to its working shape.

Referring now to FIG. 6E, the retractor head 620 prevents at least a portion of the tissue 650 (e.g., the tongue base) from deforming. For example, in one embodiment, the deployed tissue retractor 601 has a retractor head 620 that prevents deformation of at least a portion of the tongue base to prevent obstruction of the patient's airway.

The preferred qualities for a retractor head 620 that rests upon tissue 650 (e.g., tongue base mucosa) are that its depth is minimal so that it is not noticeable to the patient yet its surface area is large enough to provide sufficient counterforce. The counterforce is a pressure that prevents deformation of at least a portion of the tissue 650 (e.g., tongue base mucosa). Integral to its design is the delivery device (e.g., the needle 635) used to insert the tissue retractor 601 (e.g., the LTR). In one embodiment, the entire device (e.g., the delivery device, the needle 635, and the tissue retractor 601 disposed on the needle 635) is inserted from the anterior tongue with minimal instrumentation used at the back of the tongue. Therefore the retractor head 620 preferably automatically deploys to its working shape (i.e., FIG. 6E) after being implanted by a needle 635 inserted from the front of the tongue.

Part of this aspect of the invention includes improvements in the design of the retractor head 620 that allow it to be easily inserted. In certain embodiments, this insertion would be by a needle 635. Therefore one embodiment of this invention is a retractor head 620 that folds within a needle 635 but deploys to its working shape after insertion. Many mechanisms are known that allow a device to be minimized for insertion in the body, non-limiting examples include nitinol wire, high pressure balloons, and spring mechanisms. These mechanisms work well but add complexity and unnecessary expense.

In one embodiment, the retractor component, the retractor head 620, is oval shaped (10 mm long, 5 mm wide, 2.5 mm deep) and is molded together with the shaft 610 (1 mm in diameter) as a single piece from moderate consistency medical grade silicon (Shore 80 durometry, Nusil, Ca) (FIG. 6A). The retractor head 620 is tilted 75° in relation to the shaft 610. When the tissue retractor 601 is threaded into the needle bore 645 of a needle 635 (FIGS. 6B-6C) one side of the oval retractor head 620 extends out of the needle 635 port and projects at a 15° angle relative to the outside wall of the needle 635. When the needle 635 is inserted through tissue 650 this extension of the retractor head 620 is pushed flush against the needle 635 wall and causes a minimum increase in the needle 635 profile (FIG. 6C). However, immediately after the needle 635 passes through tissue 650 (e.g., mucosa) the retractor member 620 reverts to its extended position (FIG. 6D). The needle 635 is pulled back and removed from the tissue 650 causing the retractor member 620 to catch at least a portion of the tissue 650 (i.e., the mucosa), which prevents the tissue retractor 601 from being withdrawn along with the needle 635 from the tissue 650. After the needle 635 is removed, minor tension on the shaft 610 causes the retractor head 620 to rotate into proper position and lay flush against the mucosa (FIG. 6E).

The practical advantage of this invention is that the physician can rapidly and easily insert and withdraw the needle 635 and the tissue retractor 601 device automatically settles into its proper position when the retractor head 620 deploys and contacts the tissue 650.

2. Shaft Member. (FIG. 7)

Figure 7A:
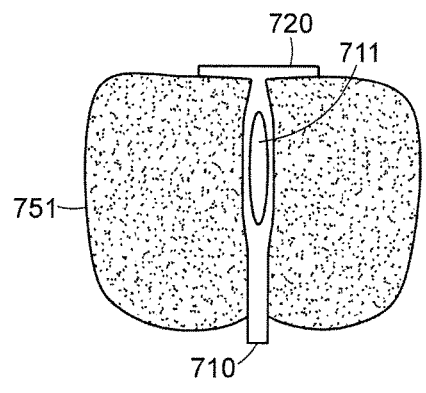
FIGS. 7A-7C illustrate a Shaft member.
Figure 7B:
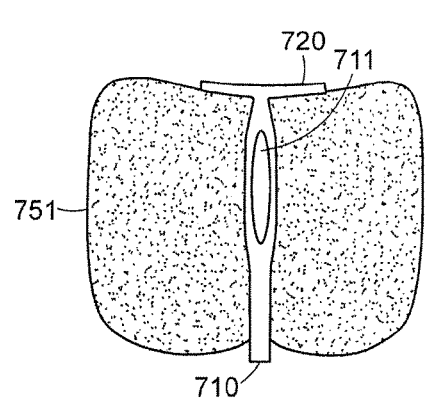
Figure 7C:
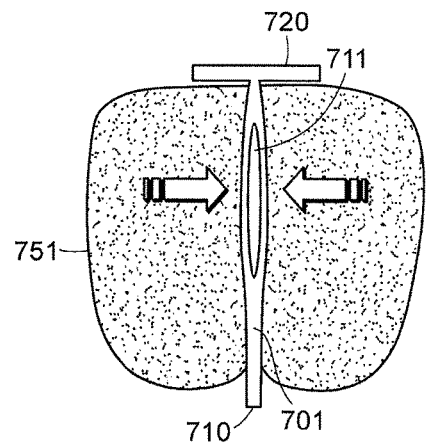

Referring now to FIGS. 7A-7C, disclosed here is a modified shaft 710 that adapts its length to avoid interfering with normal movements of the tongue 751 (e.g., the tongue base).

The counterforce exerted against the back of the tongue 751 base is preferably present during sleep but not during the awake state. More preferably, the counterforce is present when the tongue 751 is relaxed and vulnerable to posterior collapse, but not during speech and swallowing. During swallowing the tongue base moves rapidly backward about 1 cm to contact the back wall of the pharynx. The tongue base moves similarly during some speech movements, albeit with much less force. It is desirable that these swallowing and speech movements are not impaired.

In one embodiment of the shaft 710 the section within the tongue 751 is a distensible portion 711, one non-limiting example being a balloon. Compression of the balloon portion 711 of the shaft 710 allows the shaft 710 to lengthen. During swallowing the tongue 751 contracts forcefully around the shaft 710. This contraction squeezes the balloon portion 711 and lengthens it, thereby displacing the retractor head 720 superiorly. As the tongue base moves superiorly in the area of the retractor head 720 during swallowing, the compression exerted on the shaft 710 causes the shaft 710 to lengthen proportionally and prevents the retractor head 720 from exerting unneeded counterforce on the tongue base during swallowing. However, the ability to exert the proper amount of counterforce when the tongue 751 is relaxed is maintained. The amount of distensibility is from about 0.01 cm to about 10 cm, or about 1 cm.

The decrease of counterforce by the retractor head 720 during swallowing and speech can be accomplished by many known mechanical and electromechanical mechanisms. Those skilled in the art can readily appreciate that the invention can have multiple embodiments.

3. Anchor Member: Bolster, Dental, Implanted (FIGS. 8,9,10)

Disclosed here are modified anchors that allow reversible loading of an implanted tissue retractor (i.e., LTR).

Referring now to FIGS. 8A-8H, the anchor 830 is the anterior component of the tissue retractor 801 (i.e., LTR) that resists displacement of the shaft 810 and retractor head 820. In a preferred embodiment the tissue retractor 801 (i.e., LTR) is under little or no tension during the day (unloaded state) and is adjusted to exert tension at night (loaded state). In this embodiment the anchor 830 merely prevents the anterior end of the shaft 810 from being pulled back into tongue tissue 851. For this purpose a small flange is sufficient. However, at night when further retractor counterforce is desired, the anchor 830 can be replaced, modified, or supplemented; collectively referred to as a modified anchor.

One embodiment of a modified anchor is a bolster 840 that is interposed between the permanent anchor 830 and the tongue 851. This bolster 840 either lengthens the shaft 810, or if the shaft 810 is set at a fixed length it increases the total volume compressed between retractor head 820 and shaft 810. In either case the addition of the modified anchor (e.g., the bolster 840) causes a reversible increase in retractor 820 counterforce.

Figure 8C:
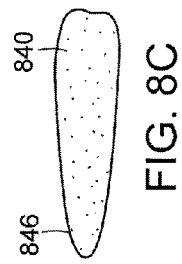
FIGS. 8A-8H illustrate an Anchor member, bolster.
Figure 8B:
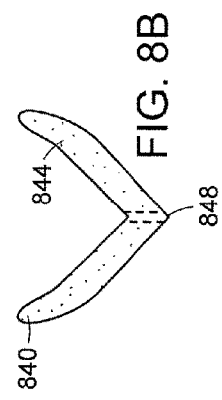
Figure 8H:
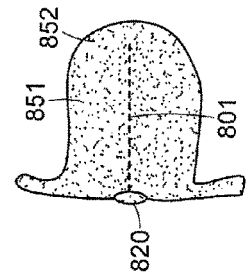
Figure 8E:
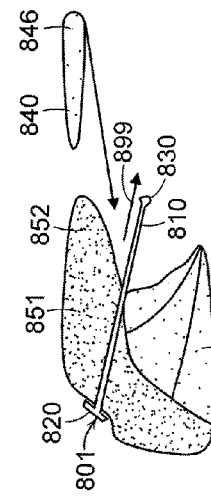
Figure 8G:
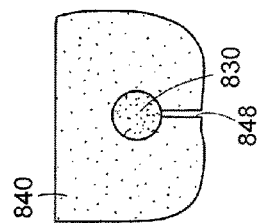
Figure 8A:
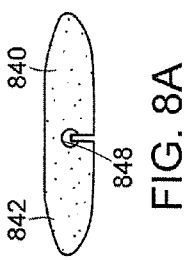
Figure 8D:
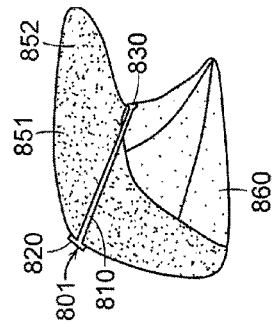
Figure 8F:
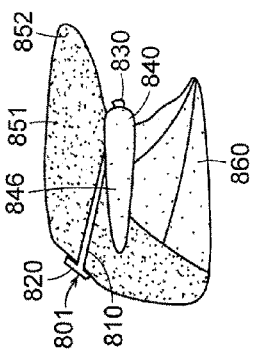

In one embodiment of the modified anchor the bolster 840 is composed of silicon gel and is shaped as a V (FIGS. 8A-8C). The concave inner surface of the 'V' adapts to the wedge shape of the frenulum 860, the structure underneath the tongue blade 852. The intent of the 'V' shape is to spread the retracting counterforce across a wide surface area of the frenulum 860. In the center of the anchor 830 bolster 840 is a conduit through which the permanent anchor 830 and shaft 810 is threaded. In one embodiment the conduit is a cleft 848 beginning in the center of the top center edge. This cleft 848 is about the width of the shaft 810 but less then that of the permanent anchor 830. The patient can reach under the tongue 851 and pull the permanent anchor 830 forward in direction 899 (FIGS. 8D-8F), slip the bolster 840 under the tongue 851, lay the shaft 810 into the cleft 848, and release the permanent anchor 830. The permanent anchor 830 then securely rests against the front surface of the cleft 848 and exerts force. The cleft 848 may be reinforced with a harder grade of silicon or another biocompatible material.

Figure 9A:
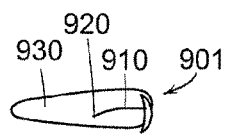
FIGS. 9A-9E illustrate an Anchor member, dental.
Figure 9A:
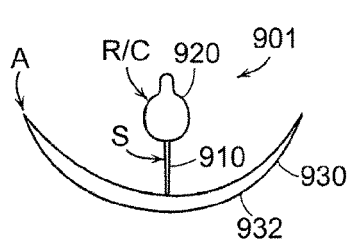
Figure 9C:
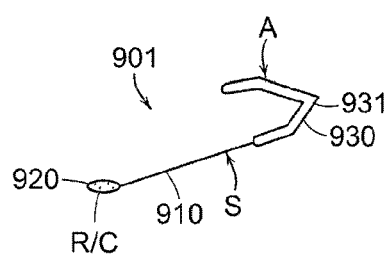
Figure 9B:
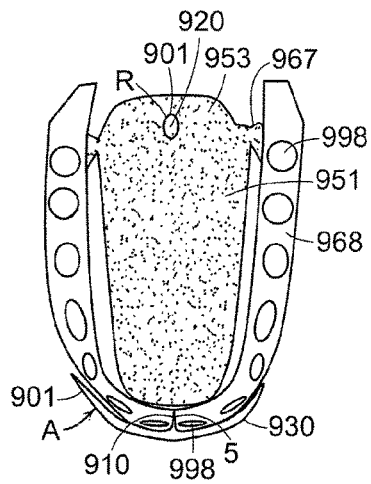
Figure 9D:
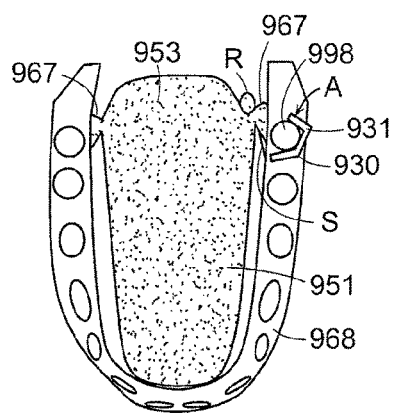

Another embodiment of this invention is to secure the permanent anchor to a modified bolster that is permanently or reversibly attached to the teeth, a dental anchor (FIGS. 9A-9E). Many devices that attach to teeth are known in the art. A non-limiting example is 'T' shaped. The top cross bar of the "T" 932 rests against the front surface of the lower incisor teeth 998. The initial section of the vertical line of the "T" 932 is thin enough to pass between the front two incisor teeth 998. This vertical part widens to allow the retractor head 920 to be threaded. The final part of the "T" 932 narrows again to about the width of the shaft 910. This mechanism allows the anchor 930 to be easily and reversibly attached to the dental bolster (FIGS. 9A-9B).

Another embodiment is a dental anchor 931 optimized for use on the sides of the mouth rather then the front. This embodiment (FIGS. 9C-9D) anchors 931 to a molar or premolar tooth 998 or neighboring structures. This embodiment is advantageous due to the short distance between the tissue retractor (e.g., an LTR) and the modified anchor, its position on the lateral aspect of the tongue 951 is unlikely to interfere with normal tongue function, and it is easily accessible for placement, adjustment and removal by patient and physician.

In a further embodiment a dental prosthesis is used as an anchor disposed in the soft palate, the palatoglossal folds, the pharyngoglossal folds, the tongue, or other upper airway sites to anchor to a tissue retractor. Dental prostheses are well known in the dental arts. In some embodiments, dental prosthesis provide a wide and stable platform for anchoring embodiments of a tissue retractor. Further embodiments can take advantage of the large size and position of these prostheses.

Figure 9E:
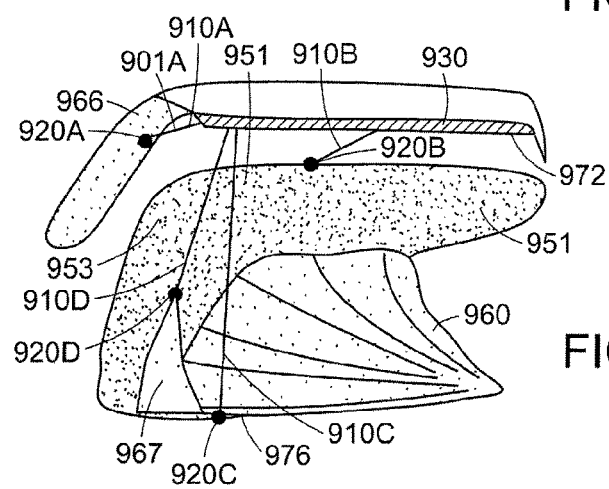

Referring now to FIG. 9E, in one embodiment, the anchor member 903 is a palatal prosthesis 972. The palatal prosthesis 972 is disposed on a portion of the soft palate 966. For example, the palatal prosthesis 972 may be disk disposed on a surface of the soft palate 966. Alternatively, the palatal prosthesis 972 may be a hook disposed inside a portion of the soft palate 966. The palatal prosthesis 972 may be a suction cup disposed on a portion of the soft palate 966. In one embodiment, a tissue retractor 901A includes a retractor member 920A disposed on another portion of the soft palate 966, the anchor member 930 is the above described palatal prosthesis 972, and a shaft 910A is disposed between the retractor member 920A and the anchor member 930. The placement of the retractor member 920A and the palatal prosthesis 972 can be selected to enlarge the airway in the area around the soft palate 966. In another embodiment, a tissue retractor 920B is disposed on the surface of the tongue 951. For example, the tissue retractor 920B is a tongue stud on the surface of the tongue 951. The tongue stud may be part of a conventional tongue piercing. The shaft 910B connects the tongue stud to the palatal prosthesis 972. The shaft 910B can have an end that connects to the tongue stud retractor member 920B by encircling or looping about all or a portion of the tongue stud. The shaft 910B can be an elastic material. The retractor member 920B is pulled toward the direction of the palatal prosthesis 972 thereby enlarging the airway behind the tongue base 953. In one embodiment, a retractor member 920C is disposed in the floor of the mouth 976. A shaft 910C is disposed between the palatal prosthesis 972 and the floor of the mouth 976.

In one embodiment, the retractor member 920C provides a protraction force that is directed to push the floor of the mouth 976 in the direction opposite the palatal prosthesis 972. More specifically, in one embodiment, the protraction force is directed inferiorly. The protection force can be provided by the shaft 910C. The shaft 910C can be a rigid material. Alternatively, the shaft 910C is made from a material that lengthens. The shaft 910C can have passive properties that enable it to lengthen, for example, the shaft 910C can include a compressed elastic, a compressed spring element, or a nitinol wire, for example. In one embodiment, the shaft includes a pressurized fluid, an electric motor or other means that exert a lengthening force. For example, the shaft 910C can include two hollow tubes with one tube sliding within the other tube to change the overall tube length. In another embodiment, the shaft 910C is a fixed length that is longer than the distance between the palatal prosthesis 972 and the floor of the mouth 976.

In one embodiment, a bolster is disposed between the shaft 910C and the floor of the mouth 976 such that the shaft 910C does not contact mucosa on the floor of the mouth 976. The bolster improves the patient's comfort. In one embodiment, the bolster feels soft and/or pliable and is biocompatible. The bolster can range in size from a 0.1 cm long by 0.1 cm wide square or to the entire surface area of the floor of the mouth. In one embodiment, the bolster is 0.5 cm wide and 1.5 cm long. Suitable bolsters are sized to fit on the floor of mouth 976 adjacent the patients tongue 951. The bolster may be positioned along the floor of the mouth from the front wall of the PGF 967 to the back wall of the mandible 968 behind the lower incisor teeth. In one embodiment, the shaft 910C exerts force to the area of the floor of mouth 976 directly incront of the PGF 967 such that the protraction force of the shaft 910C pushes a bolster such that the force is transmitted to the tongue base 953.

In one embodiment, a retractor member 920D is disposed in the PGF 967. A shaft 910D is disposed between the palatal prosthesis 972 and the retractor member 920D. The shaft 910D may be a rigid material or it may be a material that lengthens when exposed to a force. The shaft 910D exerts force by protraction or inferior force on the PGF 967. Because the PGF 967 is attached to the tongue base 953 the force exerted by the shaft 910D on PGF 967 is directly transmitted to the tongue 951, which causes protraction of the tongue base 953 thereby opening the patient's airway.

Referring still to FIG. 9E, in one embodiment, a tissue retractor for treatment of a breathing disorder includes an anchor member 930 sized for placement on or in a patient's soft palate and a shaft 910 having a first end and a second end, the first end connected to the anchor member 930. The tissue retractor also includes a retractor member 920 connected at or near the second end of the shaft 910. At least one of the shaft 910 and the retractor member 920 is positioned on or in a soft tissue located in the patient's oral cavity or pharynx. The anchor member 930, the shaft 910, and the retractor member 920 exert a force that prevents deformation of at least a portion of the soft tissue to prevent obstruction of the patient's airway. The force may be a retraction force or, alternatively, a protraction force. The retractor member 920 may be positioned on or in the soft palate, the pharyngoglossal fold, the floor of mouth, or the tongue, for example. In one embodiment, the retractor member 920 is a tongue stud on the surface of a tongue 951.

A method for treatment of a breathing disorder can include positioning a palatal prosthesis 972 on or in the patient's soft palate, positioning a retractor member 920 on or in a soft tissue located in the patient's oral cavity or pharynx, connecting a first end of a shaft 910 to the palatal prosthesis 972, and connecting a second end of the shaft 910 to the retractor member 920. At least one of the palatal prosthesis 972, the shaft 910, and the retractor member 920 interact to exert a force that prevents deformation of at least a portion of the soft tissue to prevent obstruction of the patient's airway Optionally, as discussed above, to maximize adjustability, a bolster may be inserted between the end of the shaft 910 and the patient's tissue, for example, the bolster may be inserted between the shaft 910 and the floor of the mouth 976. At least one of the palatal prosthesis 972, the shaft 910, and the retractor member 920 interact to exert one of a retraction force or a protraction force that prevents deformation of at least a portion of the soft tissue to prevent obstruction of the patient's airway.

Those skilled in the art can understand that a variety of electrical or mechanical mechanisms could be incorporated within these dental prosthesis. As a non-limiting example, an electrical motor could be used to control the force applied to coupled tissue retractors at multiple locations in the upper airway.

Referring now to FIGS. 10A-10C, in still another embodiment, the modified anchor 1031 is partially implanted into the floor of the mouth. In one embodiment of this invention a puncture is made across the frenulum 1060 or soft tissue structures of the floor of the mouth. The frenulum 1060 has a central tendon (CT) 1067. Generally, the frenulum area 1060B includes the whole genioglossus 1063 and its surface mucosa. The frenulum 1060A includes the front edge of the frenulum area 1060B. In one embodiment, a shaft (e.g., a flexible shaft) is threaded through the puncture and the ends are connected to create the modified anchor 1031, a ring like structure. The modified anchor 1031 is securely fixed within tissue (FIG. 10). In one embodiment, during sleeping hours (e.g., at night) the modified anchor 1031 is reversibly attached to the permanent anchor of a tissue retractor and the modified anchor 1031 is disengaged from the permanent anchor of the tissue retractor during waking hours (e.g., in the morning).

4. Frenulum Area Embodiments

Referring now to FIGS. 11A-11E, disclosed are methods and devices for retracting or preventing deformation of the tongue base 1153 by retracting the genioglossus muscle 1163 or the boundary fascia 1161 upon which the genioglossus muscle 1163 inserts (this area is collectively referred to as the frenulum area 1160).

It has been unexpectedly found that the shaft 1110 of the tissue retractor 1101 (i.e., an LTR) can be safely passed across the undersurface of the tongue 1151. The undersurface of the tongue 1151 contains the frenulum area 1160, which is the mucosa covering the genioglossus muscle 1163.

Figure 11B:
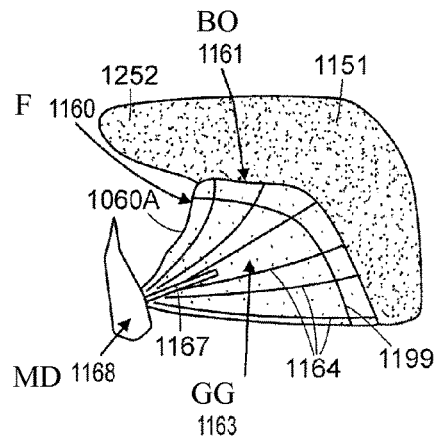
FIGS. 11A-11E illustrate a Frenulum area embodiment.
Figure 11A:
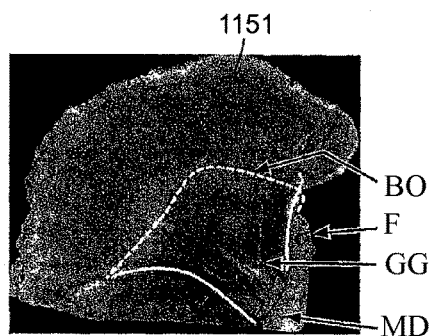
Figure 11C:
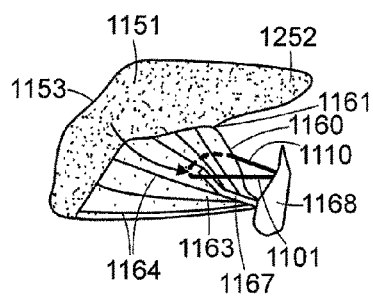

Thus, this under tongue 1151 tissue contains the genioglossus muscle 1163 and its anterior edge is the frenulum 1160 (FIGS. 11A-11B). A central tendon 1167 is substantially in the center of the genioglossus muscle 1163 spanning from the mandible 1168 up to the undersurface of the tongue 1151. The genioglossus 1163 muscle originates from the mandible 1168 and has multiple separate muscle fascicles 1164 that fan out from a horizontal to vertical angle. The genioglossus fascicles 1164 attach to a layer of connective tissue within the tongue 1151 called the boundary 1161 (FIGS. 11A-11B, dotted line). The genioglossus fascicles 1164 normally act by exerting force in the axis of the fascicle 1164 onto the part of the boundary 1161 to which the fascicles 1164 are attached. However, even when inactive, the fascicles 1164 are mechanically coupled to the tongue boundary 1161 and can exert a force on the tongue 1151 if the fascicles 1164 passively move. Unexpectedly, movement of a portion of the tongue 1151 can be done by pulling these fascicles 1164 perpendicular to their axis (FIG. 11C). To simplify the mechanism, in one embodiment, the genioglossus fascicles 1164 are lassoed by the tissue retractor 1101, which in one embodiment, is made from the shaft 1110. In one embodiment, the force provided by the tissue retractor 1101 in the genioglossus 1163 is substantially evenly distributed.

There are certain important considerations in placing a retractor through the genioglossus 1163: First, the genioglossus 1163 is soft in comparison to the tongue base 1153, therefore, too much force applied in a localized area of the genioglossus 1163 can tear the tissue or cause undesirable tissue remodeling over time, sometimes called the "cheese cutter effect". However, there is a central tendon 1167 to the genioglossus 1163 that is very strong. This central tendon 1167 is located approximately 1 cm from the edge of the frenulum area 1160. In one embodiment, the tissue retractor 1101 is located anterior to the central tendon 1167. In another embodiment, the tissue retractor 1101 is disposed posterior to the central tendon 1167. Second, the nerve supply to the genioglossus 1163 passes along the superior aspect of the muscle, therefore the top 0.5 cm of the muscle, the area 1199 directly below the tongue blade 1152, is not a preferable site for the tissue retractor 1101 implant.

In one embodiment, the tissue retractor 1101 is a shaft 1110 that has a 5 cm length of elastomeric material that is ribbon shaped. The cross sectional dimensions of the shaft 1110 are 0.5 mm depth and 3 mm width. The wider dimension of the width of the shaft 1110 will exert force on a wider area of the genioglossus 1163 tissue, because, due to its dimensions, the shaft 1110 force is dispersed over a wider area then the narrow edge of the ribbon. The tissue retractor 1101 shaft has a length that ranges from about 0.5 cm to about 5 cm, a width that ranges from about 0.1 mm to about 10 mm, and a depth that ranges from about 0.1 mm to about 2 mm.

Figure 11D:
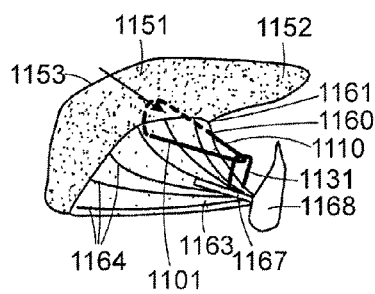

During insertion of the tissue retractor 1101 into the frenulum area 1160, the shaft 1110 is attached to a needle and passed through the genioglossus 1163 muscle approximately 1 cm behind the frenulum 1060A. Referring now to FIG. 11D, the ends of the shaft 1110 are then reversibly coupled to a modified anchor 1131. The middle section of the shaft 1110 itself exerts anterior retracting force onto the genioglossus muscle 1163 and acts as a retracting head. One or both ends of the shaft 1110 can then be brought forward and secured to a modified anchor 1131. In one embodiment, the location or angle of the modified anchor 1131 is selected to enable a desired position of the tissue retractor 1101 in the genioglossus muscle 1163. In another embodiment, the modified anchor is a tooth. The position of the tissue retractor 1101 is determined based upon the anatomy of the tongue 1151.

This displacement of the genioglossus muscle 1163 is transmitted to the tongue base 1153 causing some degree of concavity in the tongue base 1153. The passive movement is preferably in an anterior and inferior direction. In one embodiment, the displacement of the genioglossus muscle 1163 is transmitted to the tongue base 1153 and prevents the tongue base 1153 from obstructing the patient's airway. For example, the displacement of the genioglossus muscle 1163 prevents the tongue base 1153 from falling toward another tissue in the patient's airway.

The advantages of genioglossus muscle 1163 retraction is that this muscle group is easily accessible beneath the tongue 1151. The tissue of the genioglossus muscle 1163 is soft and easily compressed, making it easy to pierce without complications. The position under the tongue 1151 is invisible to others, a quality important for the patient.

A further embodiment of this invention is to pass the tissue retractor 1101 (e.g., the LTR) deeper into the tongue 1151 to couple directly to the boundary layer 1161 (FIG. 11D). The boundary layer 1161 is a relatively firm connective tissue structure which spans the length of the body of the tongue 1151. In one embodiment, the boundary layer 1161 receives the insertion of the tissue retractor 1101 through the genioglossus muscle 1163. For example, the shaft is in the genioglossus muscle 1163 and the anchor member and retractor member loop around some of the boundary layer 1161 to get firm traction. The advantages of coupling to the boundary layer 1161 are that it provides a more secure attachment then the genioglossus 1163 itself. However, greater care is needed for placement of the tissue retractor 1101 device. Specifically the lingual arteries course just superior and lateral to the boundary layer 1161 so it is essential that the insertion of the shaft 1110 of the tissue retractor 1101 be made medial to the structure of the lingual arteries.

Figure 11E:
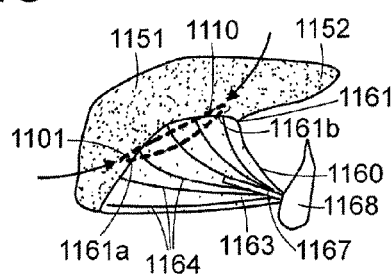
Figure 12C:
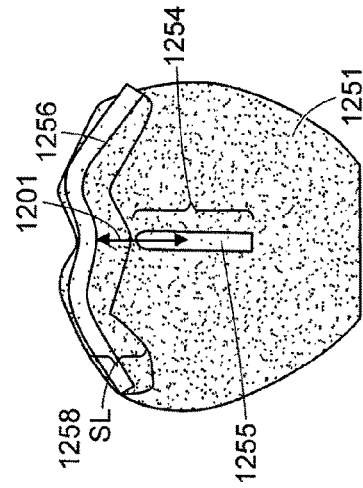
FIGS. 12A-12F illustrate a Tongue base implant.
Figure 12F:
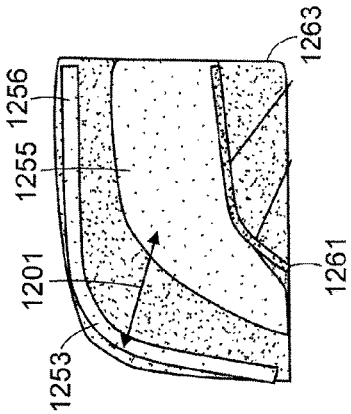
Figure 12B:
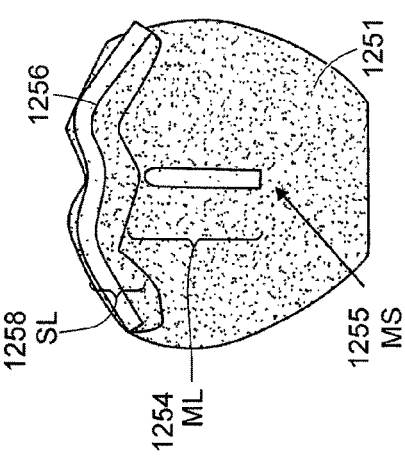
Figure 12E:
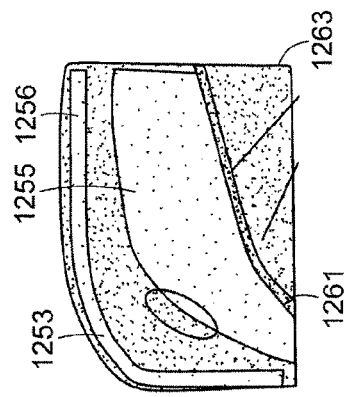
Figure 12A:
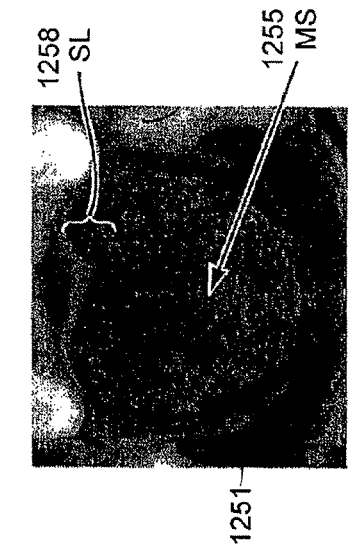
Figure 12D:
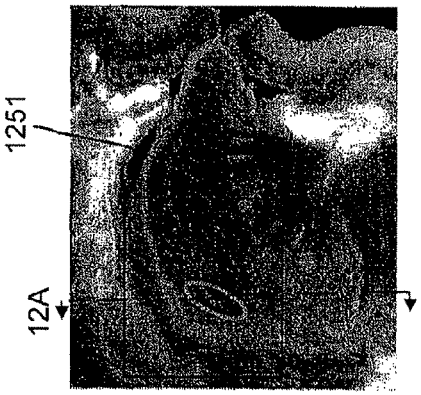
Figure 14A:
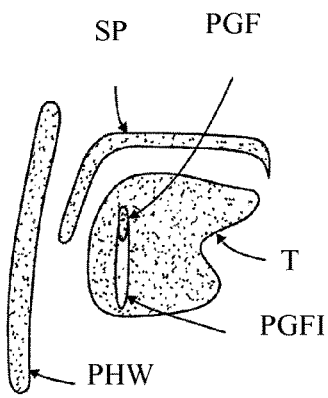
FIGS. 14A-14E illustrate The Superior Pharyngoglossal Fold.
Figure 14B:
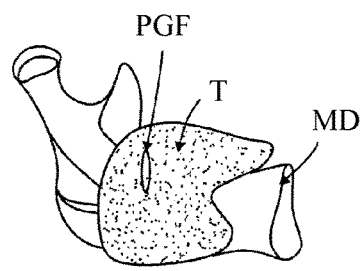
Figure 14C:
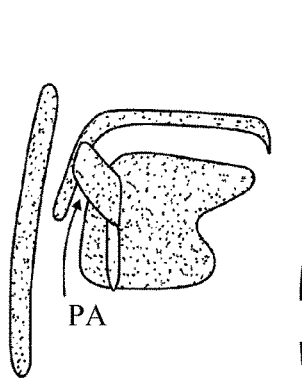
Figure 14D:
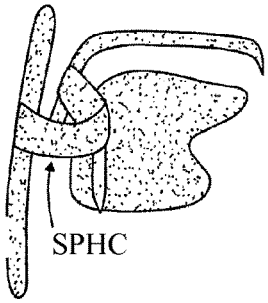
Figure 14E:
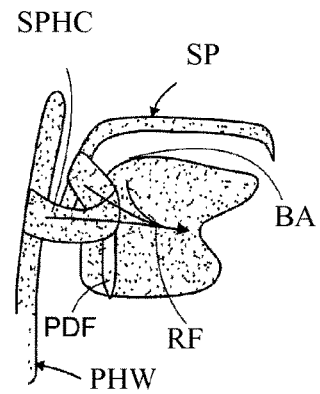

In a further embodiment, a fully implanted tissue retractor 1101 (e.g., an LTR) connects one site that effects the tongue base 1153 and is anchored at another site that does not. A non-limiting example of a fully implanted tissue retractor 1101 is shown in FIG. 11E. Here the posterior boundary layer 1161a is coupled to the anterior boundary layer 1161b. Tension between the two sites displaces the tongue base 1153 forward. Simultaneously there is some displacement force exerted around the anterior boundary site 1161b, but the displacement force on the anterior boundary site 1161b has insignificant effects on normal tongue 1151 function.

The tissue retractor 1101 may have a shape other than the ribbon shaped shaft 1110, however, the tissue retractor 1101 is positioned to take advantage to the genioglossus muscle 1163 and/or the behavior of the genioglossus fascicles 1164. In one embodiment, multiple tissue retractors 1101 are positioned in the frenulum area 1160 to prevent the tongue base 1153 from obstructing the patient's airway.

5. Implanted Tongue Base Retractor (FIG. 12)

Disclosed here are methods of implantation and devices that are implanted within the tongue and exert highly localized forces to prevent mechanical decoupling of tongue base structures.

Chronic implants within the tongue are technically challenging and potentially dangerous. The tongue is a mobile structure and tongue movements during swallowing and speech are dependent on this mobility. The tongue has no bones within it and its mechanism of movement is unique among the muscular structures of the body. Most skeletal muscles are attached to bones and movement occurs as mechanical levers. In the tongue, structures cause movement by expanding and changing their shape and volume. The mechanism is called a muscular hydrostat and is can be likened to a flexible hydraulic system. In addition, the tongue has extensive nerve and blood supply that can be easily damaged. Moreover, the tongue has a tremendous ability to remodel itself when effected by implants and other forces. When the tongue remodels itself, it adapts quickly to pressure exerted on its structure. In response to the pressure exerted on a portion of the tongue by, for example, an implant, the portion of the tongue reshapes to become, for example, thinner in region of the pressure exerted by the implant. This thinning of the tongue tissue is one reason why many prior art devices have failed, due to gradual loss of tension or extrusion. Moreover any implant is a potential site for infection and scarring. For these reasons any invasive intervention in the tongue must be designed with a detailed knowledge of tongue anatomy and physiology. Therefore, the implanted embodiments disclosed in this invention are carefully designed to be minimally invasive and to focus their effects on critical areas of pathology without risking interference with normal function.

Referring now to FIGS. 12A-12F, an implanted tissue retractor 1201 (e.g., an LTR) disclosed here is a very minimal device implanted into the tongue 1251 for example, in the tongue base 1253. The implanted tissue retractor 1201 attaches to structures within the tongue 1251 to prevent a portion of the tongue 1251 from obstructing the patient's airway by, for example, falling toward another structure in the patient's oral cavity or pharynx. In some embodiments, the at least a portion of the implanted tissue retractor 1201 is made from a flexible material that does not impede the mobility required for normal tongue 1251 function.

The tongue 1251 is covered by mucosa and this mucosa has underlying connective tissue 1256. The connective tissue 1256 is thickest below the superior surface of the tongue 1251. The connective tissue 1256 is a collagenous structure covered in mucosa in the superior layer (SL) 1258 of the tongue 1251. This superior surface is intimately connected to the underlying superior longitudinal muscle. Together the mucosa connective tissue 1256 and muscle form a superior layer (SL) 1258 that spans the superior surface of the tongue 1251 from the tongue tip to its base 1253. This superior layer is normally coupled to the underlying middle layer (ML) 1254 of the tongue 1251, which is largely composed by the transverse muscle. The transverse muscle originates from a fascial sheet called the medial septum (MS) 1255 oriented in the centerline of the tongue (mid-sagittal plane).

Although not wishing to be bound by theory, studies by the inventor suggest that the vibration during snoring and the stretching during airway obstruction gradually loosen the attachment of the superior layer 1258 to the middle layer 1254. This is reflected by a mechanical decoupling, a widening of the superior layer 1258 in the area of the tongue curve, marked by an oval in FIGS. 12D-12E. This mechanical decoupling results in a more flaccid and compliant tongue base 1253 that deforms more easily when the pressure in the airway decreases, thereby making the patient susceptible to sleep apnea and other sleep breathing disorders.

In one embodiment (see, FIGS. 12C and 12F) of the invention a very small tissue retractor 1201 (e.g., an LTR) is inserted at the curve of the tongue base 1253 to correct the mechanical decoupling of the tongue layers. In one embodiment, the tissue retractor 1201 (e.g., an LTR) is symmetrical with an arrowhead shaped retractor head and an arrowhead shaped anchor. Each end of the tissue retractor 1201 (e.g., an LTR) mechanically hooks into soft tissue. Preferably, the tissue retractor 1201 is connected between the connective tissue fascia of the mucosa 1256 and the midline septum 1255. Each end of the tissue retractor 1201 can have a hooking mechanism. The hooking mechanism can be varied and many variations are known in the art. Non-limiting examples of suitable hooking mechanisms on the tissue retractor 1201 are: hooks, barbs, helixes, staples, screws, sutures, biointegrated permanent material, collagen, and elastin. The hooking mechanism on each end of the tissue retractor 1201 can be the same as one another or can be different from one another. The tissue retractor 1201 has an anchor member and a retractor member connected by a shaft. For example, in one embodiment, the anchor member is a staple and the retractor member is a hook. However, in one embodiment, the tissue retractor 1201 has a short elastic shaft with a hook of firmer consistency at either end.

In one embodiment, a breathing disorder is treated with a tissue retractor 1201 in which a retractor member is connected at a first end of a shaft and an anchor member is connected at a second end of the shaft. The shaft is inserted into a patient's tongue 1251 between the superior layer 1258 and the middle layer 1254. One of the retractor member and the anchor member is attached to the mucosa tissue fascia, for example, to the connective tissue 1256. The other of the retractor member and the anchor member is attached to the midline septum 1255 tissue fascia. At least one of the shaft, the retractor member, and the anchor member interact to exert a pressure that prevents a portion of the patient's tongue 1251 from obstructing the patient's oral cavity or pharynx. The tissue retractor 1201 prevents a portion of the patient's tongue 1251 from moving toward other soft tissue located in the patient's oral cavity or pharynx. As a result, the airway is maintained in the open position. In some embodiments, the pressure is a counterforce pressure. In other embodiments, the pressure is exerted on the tongue base 1253. In some embodiments, the portion of the patient's tongue is the midline septum 1255 of the tongue 1251. The middle layer 1254 of the tongue 1251 can include the midline septum 1255. In some embodiments, the tissue retractor 1201 (e.g., the retractor member, the shaft, and the anchor) are positioned on a needle, the needle is inserted to a desired depth within the patient's tongue 1251, the needle is removed, and the tissue retractor 1201 remains where inserted in the patient's tongue 1251.

In alternative embodiments, the implanted tissue retractor 1201 (e.g., an LTR) can vary in overall length from 1 mm to 3 cm in length. Alternatively, longer length tissue retractors 1201 (e.g., LTR's) can couple the tongue base 1253 tissue to the boundary fascia 1261. The tissue retractor 1201 can couple the tongue 1251 and genioglossus muscle 1263, through the boundary layer 1261 to the genioglossus muscle 1263. The tissue retractors 1201 can couple the tongue 1251 to the floor of the patient's mouth or to the mandible. Coupling of the tissue retractor 1201 to the patient's tissue can be accomplished via barbs, hooks, fibrotic reaction, or other methods known in the art. The tissue retractor 1201 implant can be composed of biodegradable material that decomposes in from about a week to about a year, for example. Many materials used for surgical sutures can be adapted for use in a tissue retractor 1201 to enable the material to be biodegraded or bioresorbed when implanted in the body of the patient.

Preferably the shaft of the tissue retractor 1201 is oriented such that the force on the retractor is at least one orientation that includes downward, forward, and to the side. In one embodiment, the tissue retractor 1201 is oriented a combination of downward and forward. Multiple tissue retractor 1201 implants may be used along the midline of the tongue 1251 to distribute the coupling force without interfering with normal function. Depending on the anatomy of the patient, tissue retractor 1201 implants may be inserted at any site in the tongue 1251. In one embodiment, the tissue retractor 1201 is implanted in the midline septum 1255 of the tongue 1251. In another embodiment, the tissue retractor 1201 is implanted in the midline of the tongue curve 1253. One or more of the following aspects of the tissue retractor 1201 can be used to mold the effects of the tissue retractor 1201 for the exact needs of the individual patient: implant site and orientation, shaft length and elasticity, and hook size, shape, and hardness.

The tissue retractor 1201 implant may be bioresorbable over a period of from about 1 day to about 10 years, or from about 1 month to about 1 year, or from about 1 month to about 6 months. Preferably, the time range allows sufficient time for remodeling of the tongue 1251 in a manner that avoids breathing disorders such as snoring and sleep apnea, for example. In one embodiment, a the tissue retractor 1201 implant is bioresorbed, which is preferable to a tissue retractor 1201 implant that is permanently left in the tongue, without bioresorption.

It is preferable that permanent or bioresorbable tissue retractor 1201 implants be inserted into superficial levels of the tongue 1251 in areas normally not undergoing a great amount of shape change during normal tongue 1251 activity. Such positioning minimizes the possibility that the tissue retractor 1201 implantation will impede normal function, particularly if there is an infection or fibrous reaction to the implant. To plan for atraumatic removal of the implant in cases of, for example, infection, pain or other complication, the tissue retractor 1201 implant should be designed to be easily removed from the patient's tongue 1251 without extensive surgery. To facilitate removal of the tissue retractor 1201 implant, the tear strength of the ends of the tissue retractor 1201 (e.g., the tear strength of either the retractor member or the anchor member or both) should range from about 1 to about 1000 grams. In one embodiment, the tear strength of hooking mechanisms at each end of a tissue retractor 1201 is about 500 grams. In another embodiment, the tear strength of the ends of the tissue retractor 1201 should range from about 10 to about 100 grams. In one embodiment, where the ends of the tissue retractor 1201 has hooks with one or more arms at the first end, then one or more of the arms of the hook fold straight at a tear strength limit, which allows the tissue retractor 1201 implant to be removed from the patient's tongue 1251 without further damage to tissue of the tongue 1251 as the tissue retractor 1201 is extracted.

In further embodiments, referring now to FIGS. 12A-12F, a method for treatment of a breathing disorder employs a tissue retractor 1201, which includes a retractor member connected at or near a first end of a shaft and an anchor member connected at or near a second end of the shaft. In accordance with the method, a shaft is inserted into a patient's tongue 1251 between the superior layer 1258 and the middle layer 1254. One of the retractor member and the anchor member is attached to the mucosa tissue fascia. The other of the retractor member and the anchor member is attached to the midline septum 1255 tissue fascia. At least one of the shaft, the retractor member and the anchor member interact to exert a counterforce pressure that prevents a portion of the patient's tongue 1251 from obstructing the patient's oral cavity or pharynx. The method can also include positioning the tissue retractor 1201, namely the retractor member, the shaft, and the anchor member, on a needle and inserting the needle to a desired depth within the patient's tongue 1251, and thereafter removing the needle to leave the tissue retractor 1201 inserted in the patient's tongue 1251.

In some embodiments, the portion of the patient's tongue 1251 that is prevented from obstructing the patient's oral cavity or pharynx is the base 1153 of the patient's tongue. In some embodiments, one or more of the shaft, the retractor member, and the anchor member is bioresorbable. After insertion of the tissue retractor 1201 into the patient's tongue 1251 all or a portion of the tissue retractor 1201 is bioresorbed by the patient's body. In some embodiments, the portion of the patient's tongue 1251 is the midline of the tongue. The middle layer 1254 can be the midline septum 1255.

6. Tongue Base Retraction (FIG. 13)

Disclosed here are embodiments of the invention that focus on retracting tissue of the tongue base, particularly the tongue base mucosa. This has the advantage that it is easy to insert by the physician, minimally invasive and easily adjustable by the patient.

Referring now to FIGS. 13A-13D, in one embodiment, the tissue retractor 1301 device is inserted from one site to another site and both sites are on the superior surface of the tongue 1351, which can include the tongue base surface. The anterior part of the tissue retractor 1301 device is the anchor member 1330 and the posterior part is the retractor member 1320. In the tissue retractor, a shaft 1310 runs between the anchor member 1330 and the retractor member 1320. Tension between the retractor member 1320, the shaft 1310, and the anchor member 1330, retracts the tongue 1351 surface and displaces the tongue base. Although the counter traction of the tissue retractor 1301 affects the anterior tongue surface, it has no effect on normal tongue 1351 function.

In one embodiment, referring to FIG. 13A, the shaft 1310 of the tissue retractor 1301 passes directly underneath the mucosa of the tongue 1351. In another embodiment, referring to FIG. 13B, the shaft 1310 takes a more direct line through the tongue 1351. Passing the shaft directly underneath mucosa of the tongue 1351 (see, FIG. 13A) is easier for the physician than inserting it directly through the tongue 1351 (see, FIG. 13B). In the configuration shown in FIG. 13A, the force at the retractor member 1320 (e.g., the retractor head) is oriented laterally, and this causes the mucosa posterior to the retractor member 1320 to be pulled taut with some degree of indentation. In the more direct route inserted through the tongue 1351 and shown in FIG. 13B, the retraction force of the retractor member 1320 is oriented close to perpendicular to the tongue surface and there is more indentation then mucosal tension as compared to the less direct route where the shaft 1310 passes directly underneath the mucosa of the tongue 1351. The exact orientation of the tissue retractor 1301 and the insertion path of the tissue retractor 1301 can be varied to maximize the beneficial effects of the tissue retractor 1301 in the patient's tongue 1351.

Referring now to FIG. 13C, in another embodiment, the tissue retractor 1301 shaft 1310 runs most of its course along the surface of the tongue 1351. A portion of the shaft 1310 is disposed under the mucosa close to the retractor member

1320 and is connected to the retractor member 1320, another portion of the shaft 1310 is disposed under the mucosa close to the anchor member 1330 and is connected to the anchor member 1330, and the remainder of the shaft 1310 is disposed along the external surface of the tongue 1351. This has the advantage of avoiding even the minimally invasive tunnels formed by FIGS. 13A and 13B. Furthermore the configurations disclosed in FIGS. 13A, 13B, and 13C, can be combined and the shaft 1310 can travel the entire distance under the mucosa or can re-emerge one or more times (13. C).

In another embodiment, referring now to FIGS. 13D-13H, at least a portion of the anchor member 1330 and/or at least a portion of the retractor member 1320 can be embedded beneath mucosa on the soft tissue 1350 and the shaft 1310 is, optionally, detachable. In one embodiment the anchor member 1330 has a first portion and a second portion and/or the retractor member 1320 has a first portion 1321 and a second portion 1322. The first portion (e.g., of the anchor member and/or the retractor member 1321) has one diameter and the second portion (e.g., of the anchor member and/or the retractor member 1322) has another diameter. The first portion has a diameter that ranges from about 1 mm to about 20 mm, from about 2 mm to about 10 mm, or from about 3 mm to about 7 mm. The second portion has a diameter that ranges from about 1 mm to about 20 mm, from about 2 mm to about 10 mm, or from about 3 mm to about 7 mm.

In one embodiment, referring to FIGS. 13E-13H, the first portion 1321 is a silastic disc about 5 mm in diameter that is implanted under the mucosa of the soft tissue 1350. The second portion 1322 has a 1 mm diameter extension 1323 that comes out of the pocket of soft tissue 1350 in which the first portion 1321 is implanted. The extension 1323 ends in a second portion 1322 which, in one embodiment, is a 2 mm disc. The shaft 1310 reversibly couples to the extension 1323 between the first portion 1321 and the second portion 1322. Preferably, shafts 1310 are elastomeric. In one embodiment, the shaft 1310 is a simple medical grade rubber band. In another embodiment, the shaft 1310 is a 1×1 mm strip of elastomeric material with expansion at either end to accommodate precut keyholes for attachment (e.g., reversible attachment) to an external portion of an implanted anchor member 1320 or retractor member 1330. In one embodiment, the attachment holes have 2 mm or greater inner keyholes to allow the end of the stretched shaft 1310 to pass over the retractor second portion 1322 and/or the extension 1323 and 1 mm outer holes or clefts that slot into the extension 1323. In some embodiments, materials of the tissue retractor are pigmented to match the color of the tongue mucosa 1350. Referring now to FIG. 13H, in a further embodiment, the patient is allowed to depress the elevated extension 1323 and/or the retractor second portion 1322 so that it is flush with the mucosa, particularly when the tissue retractor is not in use. Suitable mechanisms known in the art may be used to allow reversible depression of a button like device of the retractor member 1320.

In a further embodiment, referring to FIG. 13I, an anchor member 1330 is composed of an elastic sleeve or band 1370 slipped over the tongue 1351 blade. The shaft 1310 may be an integral part of the band 1370 or, alternatively, the shaft 1310 is a separate attachable component. The band 1370 may be made of biocompatible materials such as silicone or other biocompatible elastomers. The distal end of the shaft 1310 can be reversibly attached to a portion of the retractor member 1320. In one embodiment, referring again to FIGS. 13E-13H, the shaft 1310 reversibly couples to the extension 1323 between a first portion 1321 and the second portion 1322. In another embodiment, a portion of the shaft 1310 reversibly attaches to the second portion 1322 of the retractor member 1320.

Suitable mechanisms by which a portion of the shaft 1310 and the implant (e.g., the retractor member 1320) are coupled may include elastic bands, clips, magnets of opposite polarity, a first magnet and a material of opposite polarity, and other mechanisms well known to those skilled in the art. The advantages of this arrangement are that only a small partially embedded implant (e.g., retractor member 1320 having an implanted first portion 1321 and a second portion 1322) is needed to achieve retraction of the soft tissue 1350 (e.g., a portion of the tongue 1351).

Referring now to FIGS. 13A-13I, a tissue retractor 1301 for treatment of a breathing disorder has a retractor member 1320 with a first portion 1321 sized for implantation into a soft tissue located in a patient's oral cavity or pharynx and a second portion 1322 sized for placement external to the soft tissue. A portion of a shaft 1310 (e.g., the first end 1311 of the shaft 1310) contacts the second portion 1322 of the retractor member 1320 and another portion of the shaft 1310 connects at or near an anchor member 1330. At least one of the retractor member 1320, the shaft 1310, and the anchor member 1330 interact to exert a pressure that prevents deformation of at least a portion of the soft tissue that prevents obstruction of the patient's airway. In one embodiment, the shaft 1310 is external to the soft tissue. In some embodiments, a first end 1311 of the shaft 1310 connects at or near the anchor member 1330, a second end of the shaft 1310 connects at or near a second anchor member 1330, and the portion of the shaft 1310 exerts the pressure on the second portion 1322 of the retractor member 1320. In some embodiments, the anchor member 1330 is a first magnet, the first end 1311 of the shaft 1310 comprises a second magnet that attracts to the first magnet, the second anchor member 1330 comprises a third magnet, and the second end of the shaft 1310 comprises a fourth magnet that attracts to the third magnet.

In some embodiments, the second portion 1322 of the retractor member 1320 has a low profile when not contacting the shaft 1310.

The anchor member 1330 can be a band 1370 surrounding at least a portion of the external diameter of a patient's tongue 1351. The anchor member 1330 can be a stud (e.g., a tongue stud commonly used in tongue piercing typically associated with non-medical and cosmetic applications) on the external surface of a patient's tongue 1351.

In some embodiments, a method for treatment of a breathing disorder includes implanting a first portion 1321 of a retractor member 1320 into a soft tissue located in a patient's oral cavity or pharynx with a second portion 1322 of the retractor member exterior to the soft tissue. A first end 1311 of a shaft 1310 is connected to the retractor member 1320 and an anchor member 1330 is connected to a second end of the shaft 1310. At least one of the retractor member 1320, the shaft 1310, and the anchor member 1330 interact to exert a pressure that prevents deformation of at least a portion of the soft tissue that prevents obstruction of the patient's airway. The shaft may be external to the soft tissue. The second portion 1322 of the retractor member 1320 has a low profile when not connected to the first end 1311 of the shaft 1310. In some embodiments, the anchor member 1330 has a first portion implanted in a soft tissue located in a patient's oral cavity or pharynx and an anchor member 1330 second portion external to the soft tissue. In some embodiments, the anchor member 1330 is a band 1370 surrounding at least a portion of the external diameter of a patient's tongue 1351. In other embodiments, the anchor member 1330 is a stud on an external surface of the patient's tongue 1351. In one embodiment, at least a portion of the retractor member 1320 is positioned in the region of the pharyngoglossal fold.

In some embodiments, referring now to FIG. 13J, a first anchor member 1330 is positioned in a first region of soft tissue located in a patient's oral cavity or pharynx and a second anchor member 1330 is positioned in a second region of soft tissue. A first portion of a retractor member 1320 is inserted into a third region of soft tissue located in the patient's oral cavity or pharynx and a second portion of the retractor member 1320 is exterior to the third region of soft tissue. A first end of a shaft 1310 is connected at or near the first anchor member 1330 and a second end of the shaft 1310 is connected at or near the second anchor member 1330. One or more of the first anchor member 1330, the second anchor member 1330, the retractor member 1320, and the shaft 1330 interact to exert a pressure that prevents deformation of at least a portion of soft tissue to prevent obstruction of the patient's airway. In one embodiment, at least a portion of the shaft exerts a pressure on the retractor member that prevents deformation of the third region of soft tissue. In one embodiment, the first anchor member 1330 is a first magnet, the first end of the shaft 1310 is a second magnet that attracts to the first magnet, the second anchor member 1330 is a third magnet, and the second end of the shaft 1310 is a fourth magnet that attracts to the third magnet. Optionally, one of the above-described magnets is replaced with a material other than a magnet (e.g., a ferrous material) to which another magnet is attracted.

In some embodiments, referring still to FIG. 13J, an anchor member 1330 is placed in each PGF 1357. The anchors 1330 are attachment points for a shaft 1310 (e.g., an elastic band) passing over the base of the tongue 1351 the shaft 1310 serves to retract the base of the tongue 1351. For example, one method for breathing disorder treatment includes positioning a first anchor member 1330 in the region of the first pharyngoglossal fold 1357, positioning a second anchor member 1330 in the region of the second pharyngoglossal fold 1357, and connecting a first end of a shaft 1310 at or near the first anchor member 1330 and connecting a second end of the shaft 1310 at or near the second anchor member 1330. At least one of the first anchor member 1330, the second anchor member 1330 and the shaft 1310 interact to distribute a force on at least a portion of a tongue 1351 that prevents obstruction of the patient's airway. A force is applied to the portion of the tongue 1351 the prevents the portion of the tongue 1351 from falling toward other tissues located in the oral cavity or pharynx. In this way, the patient's airway is maintained in the open position.

In some embodiments, the first anchor member 1330 comprises a first magnet, the first end of the shaft 1310 comprises a second magnet that attracts to the first magnet, the second anchor member 1330 comprises a third magnet, and the second end of the shaft 1310 comprises a fourth magnet that attracts to the third magnet.

In one embodiment, a first portion of a retractor member 1320 is inserted into the tongue 1351, a second portion of the retractor member 1320 is exterior to the tongue 1351, and at least a portion of the shaft 1310 contacts the second portion of the retractor member 1320. At least one of the first anchor member 1330, the second anchor member 1330, the retractor member 1320, and the shaft 1310 interact to distribute a force on at least a portion of the tongue 1351 to prevent obstruction of the patient's airway. In one embodiment, a portion of the shaft 1310 (e.g., a first end of the shaft 1310) contacts, is coupled to, or presses upon a smaller retractor member 1320 that is semi-implanted in the tongue 1351 tissue. In one embodiment, at least a portion of the shaft 1310 is internal to the tongue 1351.

Referring now to FIG. 13K, a first tissue retractor 1301*a* (e.g., an LTR) is anchored beneath the tongue 1351 blade by a first anchor member 1330*a*, a first shaft 1310*a* passes through the tongue blade to a first retractor member 1320*a*. The first retractor member 1320*a* acts as a modified anchor member and provides a second anchor member 1330*b* on the superior surface of the tongue 1351. A second shaft 1310*b* passes posteriorly to a semi implanted second retractor member 1320*b*. The semi implanted second retractor member 1320*b* has a first portion implanted in the tongue 1351 and a second portion exterior to the tongue 1351. The use of a first tissue retractor 1301*a* allows adjustment of tension of the second tissue retractor 1301*b*. For example, the anchor site of the first anchor member 1330*a* located beneath the tongue blade 1352 can be adjusted such that the retraction force of the first retractor member 1320*a* is altered. In this way, adjustment of the first anchor member 1330*a* adjusts the second anchor member 1330*b*. Thus, the force exerted by the second retractor member 1320*b* by the second anchor member 1330*b* is altered by adjusting the first anchor member 1330*a*. More specifically, in one embodiment, the patient manipulates the second tissue retractor 1301*b* by twisting the first tissue retractor 1301*a* to pull slack from the shaft 1310*b* and thereby increase the force exerted by the semi implanted second retractor member 1320*b*.

Referring now to FIG. 13L, a tissue retractor 1301 includes a shaft 1310 sized for insertion into a patient's tongue 1351, a retractor member 1320 is connected at or near a first end of the shaft 1310 the retractor member 1320 is positioned at the external surface of the tongue 1351 and an anchor member 1330 is connected at or near a second end of the shaft 1310. Referring also to FIG. 13M, a band 1370 is sized to surround at least a portion of the external diameter of the tongue 1351 and the band 1370 moves in the direction 1379 to exert a pressure on at least one of a portion of the retractor member 1320 and a portion of the shaft 1310 to prevent deformation of a portion of the tongue 1351 preventing deformation of a portion of a tongue 1351 avoids obstruction of the patient's airway. A force is applied to the portion of the tongue 1351 the prevents the portion of the tongue 1351 from falling toward other tissues located in the oral cavity or pharynx. In this way, the patient's airway is maintained in the open position. In some embodiments, the band 1370 is dimensioned to rotate and push at least one of a portion of the retractor member 1320 and a portion of the shaft 1310.

In one embodiment, the tissue retractor 1301 is a rigid shaft 1310 that connects an anchor member 1330 below the tongue blade 1352 to a retractor member 1320 above the tongue blade 1352. Referring now to FIG. 13M, a sleeve (e.g., a band 1370) is reversibly placed over the tongue blade 1352. The tissue retractor 1301 shown in FIG. 13L is rotated forward by the band 1370. More specifically, the retractor member 1320 and/or a portion of the shaft 1310 are rotated forward by the band 1370 when the band 1370 is reversibly placed over the tongue blade 1352. The rotation of the retractor member 1320, along with the rigid shaft 1310, displaces the tissue of the tongue base 1353 along the midline. In some embodiments, the band 1370 rotates in the band direction 1379 shown in FIG. 13M to displace the tissue of the tongue base 1353 such that the tissue of the tongue base 1353 does not fall toward the soft palate, the pharyngeal wall, and/or other tissues in the oral cavity or pharynx and the patient's airway is maintained in the open position.

In some embodiments, referring to FIGS. 13L-13M, a method for treatment of a breathing disorder includes inserting at least a portion of a shaft 1310 into a patient's tongue 1351, connecting a retractor member 1320 at or near a first end of the shaft 1310 at an external surface of the tongue 1351, and connecting an anchor member 1330 at or near a second end of the shaft 1351. The method for treatment includes surrounding at least a portion of the external diameter of the tongue 1351 with a band 1370 disposed adjacent the retractor member 1320 and moving the band 1370 in, for example, the direction 1379 to exert a pressure on at least one of a portion of the retractor member 1320 and at least a portion of the shaft 1310 to prevent deformation of at least a portion of the tongue 1351 that prevents obstruction of the patient's airway. In some embodiments, moving the band 1370 comprises rotating the band 1370 and pushing at least a portion of the retractor member 1320 and at least a portion of the shaft 1310 to displace at least a portion of the tongue 1351 to prevent obstruction of the patient's airway. In this way at least a portion of the tongue 1351 does not fall toward other tissues in the oral cavity or pharynx (e.g., the soft palate and/or the pharyngeal wall) and the patient's airway is maintained in the open position.

Referring still to FIGS. 13L-13M, the tissue retractor 1301 is a common tongue ring (e.g., the retractor member 1320 is the tongue stud that sits on the top surface of the tongue 1351). And the band 1370 sits adjacent the tongue stud and rotates the tongue ring (e.g., the tongue stud and a portion of the shaft of the tongue ring) to displace at least a portion of the tongue 1351 to prevent obstruction of the patient's airway. In some embodiments, the tissue retractor 1301 can be loaded, e.g., the band 1370 is placed adjacent to the tissue retractor 1301 when avoiding obstruction of the patient's airway is desired (e.g., at a time when the patient plans to sleep).

In other embodiments, referring to FIGS. 13K-13L and to the previously described FIG. 9E, the retractor member 1320 (e.g., the tongue stud of a common tongue ring) is connected to a palatal prosthesis, one or more of the patient's teeth, or other dental anchor by, for example, a rubber band or a suture. Alternatively or in addition, the anchor member 1330 (e.g., the portion of a common tongue ring beneath the tongue) can be connected to a modified anchor (e.g., a dental anchor or an anchor in the frenulum area).

7. Pharyngoglossal Fold

Referring now to FIGS. 14A-14E, 15A-15F, and 16A-16F, disclosed here are methods and devices for using the PGF as a retractor or anchor site in order to beneficially effect the tongue, pharyngeal walls and/or soft palate. On both sides of the tongue thin folds of mucosa connect the tongue to the mandible. These are called the pharyngoglossal folds (PGF). Within these folds are the palatoglossal, superior constrictor, styloglossus and hyoglossus muscles, from superior to inferior respectively. The PGFs separate the oral cavity (anterior) from the pharynx (posterior). Anterior to this PGF attachment there is no lateral connection of the tongue and it is freely mobile. One of the muscles within the PGF is the palatoglossus which courses superiorly to connect with the soft palate, thereby forming what is seen in mouth as the anterior tonsillar pillar.

Unexpectedly, the PGF has been found to have several advantages as a retraction site that enlarges the pharyngeal airspace. The connective tissue of the PGF is connected with the connective tissue of the tongue. Therefore, it has been unexpectedly found that traction on the PGF is transmitted to the base of tongue. Moreover, as the superior pharyngeal constrictor and palatoglossus muscles are attached to the PGF and in turn connect with the lateral pharyngeal walls and soft palate these structures, the superior pharyngeal constrictor and palatoglossus muscles, can also be retracted (FIG. 14). In particular, a preferred site within PGF is its superior end, at the superior end many of these muscles (e.g., the superior pharyngeal constrictor, palatoglossus muscles, the lateral pharyngeal walls, and the soft palate) overlap as they insert into the tongue. Therefore, retraction at one site expands the pharyngeal airway by simultaneously stiffening and/or retracting the tongue base, lateral pharyngeal walls and soft palate. This combined effect of an expanded pharyngeal airway has a beneficial effect on sleep disordered breathing.

A further advantage of the PGF is that it is easily accessible to both the physician and patient. The PGF is not normally seen during examination of the mouth as it is in a folded state and hidden by the tongue surface that sits above the PGF. However, the PGF can be easily palpated by sliding a finger along the floor of the mouth next to the mandible, at the level of the edge of the mandible a smooth vertical wall is reached which blocks entry into the pharynx, this smooth vertical wall is the PGF. To visualize the PGF the tongue can be retracted medially with a tongue blade.

A further advantage of the PGF is that the PGF does not have a lot of sensory innervation. The area of the mouth around the PGF is highly sensitive. Specifically, the tonsillar pillars (discussed in greater detail in association with FIG. 17) and the tongue surface next to the PGF are particularly sensitive areas of the upper airway that can cause reflex gagging. However, it has unexpectedly been found that touching the PGF itself causes little or no reflex gagging. Moreover, where there is any sensation (e.g., even a small amount of sensation) caused by contacting or touching the PGF, when a device is placed in the region of the PGF and contacts the PGF for a period of time any sensation disappears within minutes of the device contacting the PGF.

A further advantage of the PGF is that it is thin and easy to puncture yet contains enough connective tissue to provide a firm interface with all or a portion of a tissue retractor (e.g., a retractor member, a shaft, and an anchor member). Anatomical studies by the inventor have shown that the PGF has few neurovascular structures. The PGF has a thickness that ranges from about 1 mm to about 3 mm. Therefore contacting, piercing, or puncturing the PGF is generally safe and there is little risk of damage to the PGF, due to the PGF thickness. The tissue in the PGF has only a minor amount of blood vessels and nerves.

Figure 15A:
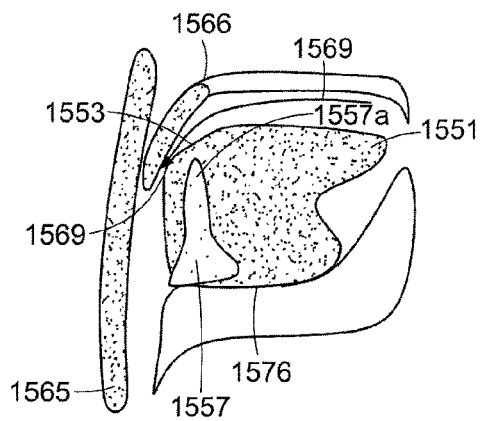
FIGS. 15A-15F illustrate Pharyngoglossal Fold embodiments.

In some embodiments, a tissue retractor (e.g., an LTR) is used to displace the PGF and/or tissue in the region of (e.g., neighboring) the PGF. In some embodiments, retraction of the PFG is in an anterior direction such that anterior retraction of the PGF displaces the entire base of the tongue anteriorly thereby increasing the patients retroglossal and retropalatal airspace. FIG. 15A shows an obstructed airway and FIGS. 15B-15F show anterior retraction of the tongue base due to PGF retraction. In some embodiments, inferior retraction of the PGF displaces the tongue base inferiorly thereby removing tissue volume from the retropalatal area, the narrowest part of the upper airway. Thus inferior retraction increases the retropalatal airspace, which is desirable for treatment of breathing disorders such as, for example, sleep apnea. In another embodiment, lateral retraction of the PGF would stiffen and flatten the posterior surface region of the tongue base. A flatter posterior surface region of the tongue base may improve the available airspace in the patient's upper airway and therefore be desirable for breathing disorder treatment. Without being bound to any theory, it is believed that one or more of anterior retraction, interior retraction, and lateral retraction of the PGF are more effective for breathing disorder treatment than are posterior retraction or medial retraction of the PGF.

Retraction of the PGF may be in a single direction or in multiple directions (e.g., retraction of the PGF may be unilateral or bilateral). For example, in one embodiment the PGF on one side of a patient's mouth (e.g., the first side) is subject to anterior retraction by a first tissue retractor and the PGF on the other side of the patient's mouth (e.g., the second side) is subject to anterior retraction by a second tissue retractor. Methods of PGF retraction could be acute, just during an obstructive episode, or semi acute, while sleeping (e.g., overnight), or for extended durations. Extended durations of PGF retraction would likely cause tissue remodeling that would cause the patient's tongue to tend to remain in a more anterior position such that when the tissue retractor is removed from the PGF and no force is being applied to the PGF the tissue remodeled tongue remains positioned in a more anterior position than its location prior to being subject to PGF retraction.

FIGS. 15A-15F depict the PGF 1557 and embodiments of PGF 1557 retraction. FIG. 15A shows the posterior collapse of the tongue 1551 whereby the tongue base 1553 collapses toward the pharyngeal wall 1565 and/or the soft palate 1566 to reduce size of the patient's airway. Some patient's having breathing disorders including snoring and sleep apnea suffer from a reduction of available patient airway to airflow 1569 as depicted by FIG. 15A. Airway airflow 1569 reduction caused by the posterior collapse of the tongue 1551 can actually obstruct a portion of the airway or can create the sensation to the patient that the reduced size airway is obstructed to airflow 1569. In accordance with some embodiment's of breathing disorder treatment, devices and methods are employed to improve the patient's airway in a manner that prevents obstruction (e.g., prevents actual obstruction and/or prevents an airway size reduction that produces the sensation in the patient that the airway is obstructed to airflow 1569).

Figure 15B:
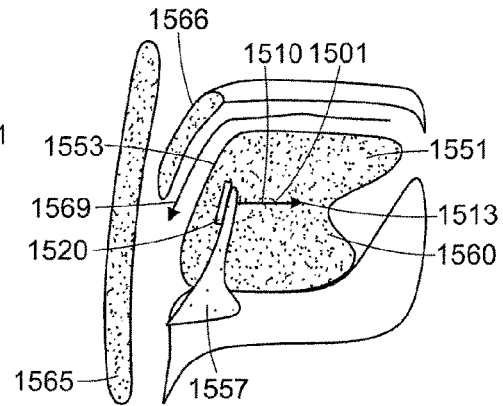

Referring now to FIG. 15B, in one embodiment, a retractor member 1520 is positioned at or near the PGF 1557 (i.e., the first PGF), a shaft 1510 connects to the retractor member 1520 and passes across the frenulum 1560 (i.e., on the external surface of the frenulum 1560) to attach to a similarly positioned retractor member 1520 positioned at or near the PGF on the opposite side of the patient's oral cavity (i.e., the second PGF). More specifically, in some embodiments, a retractor member 1520 is adjacent the PGF 1557 (i.e., the first PGF) and a portion of the shaft 1510 is inserted into the PGF 1557, another portion of shaft 1510 passes across the frenulum 1560, the shaft 1510 enters the other PGF (i.e., the second PGF) and another retractor member is adjacent the second PGF. The two PGF's are moved in the retraction direction 1513. Movement of the two PGF's in the retraction direction 1513 opens up the patient's airway to airflow 1569 by, for example, moving the tongue base 1553 in the retraction direction 1513 rather than toward the pharyngeal wall 1565 and/or toward the soft palate 1566.

Figure 15C:
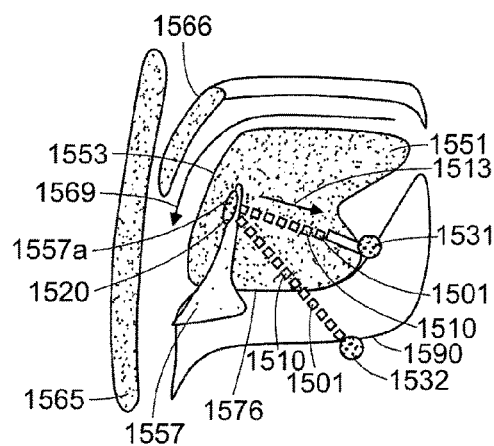

Referring now to FIG. 15C, a retractor member 1520 is about or in the PGF 1557 and a shaft 1510 passes through the tongue 1551 tissue to emerge and connect to a modified anchor 1531. The modified anchor 1531 may be a dental appliance or a tooth, for example. In one embodiment the retractor member 1520 lays against the PGF 1557, a portion of the shaft 1510 passes through the PGF and another portion of the shaft 1510 passes through the tongue 1551 to the modified anchor 1531 located adjacent the frenulum and/or in the region of the mandible. Movement of the PGF 1557 in the retraction direction 1513 opens up the patient's airway to airflow 1569 by, for example, moving the tongue base 1553 in the retraction direction 1513 rather than toward the pharyngeal wall 1565 and/or toward the soft palate 1566.

Referring still to FIG. 15C an alternative embodiment is also depicted showing that the retractor member 1520 in the PGF 1557 passes through the tongue 1551 tissue through the floor of the mouth to an external anchor 1532 resting on the patient's skin 1590, e.g., against the patient's chin. In one embodiment, the retractor member 1520 lays against the PGF 1557, a portion of the shaft 1510 passes through the PGF 1557 and another portion of the shaft 1510 passes through the tongue 1551 to the external anchor 1532 resting external to the oral cavity on the patient's skin 1590. The tissue retractor 1501 opens up the patient's airway to airflow 1569 by, for example, moving the tongue base 1553 in the retraction direction 1513 rather than toward the pharyngeal wall 1565 and/or toward the soft palate 1566.

Figure 15D:
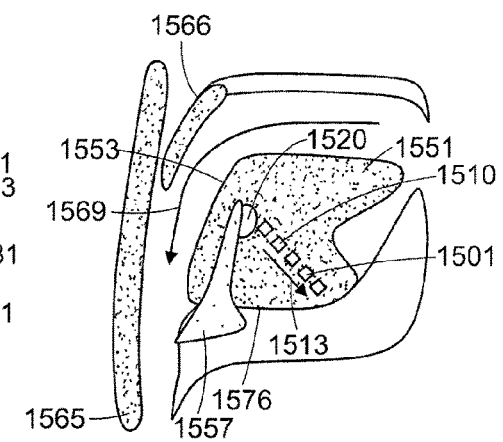

In one embodiment, referring now to FIG. 15D, an implanted tissue retractor 1501 has a retractor member 1520 implanted within the PGF 1557 (or in neighboring tongue 1551 tissue) and a shaft 1510 passes through the tongue 1551 and passes anteriorly and inferiorly to an implanted anchor in the tongue 1551, an implanted anchor in the genioglossus muscle, and/or an implanted anchor in structures located in or at the floor of mouth. The tissue retractor 1501 opens up the patient's airway to airflow 1569 by moving the PGF 1557 in the retraction direction 1513, which moves the tongue base 1553 away from the pharyngeal wall 1565 and/or the soft palate 1566.

Figure 15E:
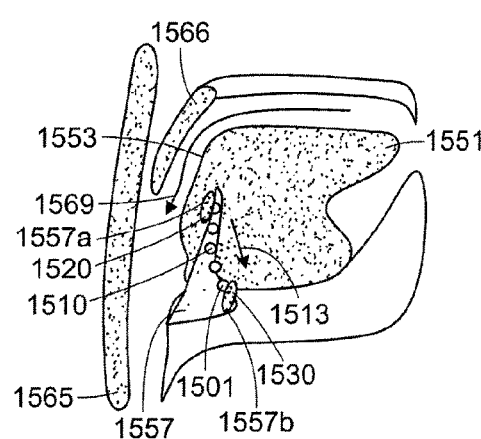

Referring now to FIG. 15E, in one embodiment the retractor member 1520 is implanted against the superior PGF 1557a and the shaft 1510 passes inferiorly through or outside the PGF 1557 to an anchor member 1530 that is implanted against the same PGF 1557 either on the same side or on the opposite side of the retractor member 1520. Referring still to FIG. 15E, the tissue retractor 1501 includes a retractor member 1520 in the superior PGF 1557a, a shaft 1510 passing through or outside the PGF 1557, and an anchor member 1530 in the inferior PGF 1557b. This method retracts the superior PGF 1557a in an inferior direction, namely, in the retraction direction 1513, which opens up and prevents obstruction of the patient's airway to airflow 1569. Retraction of the PGF 1557 avoids soft tissue movement toward the pharyngeal wall 1565 and/or the soft palate 1566.

Figure 15F:
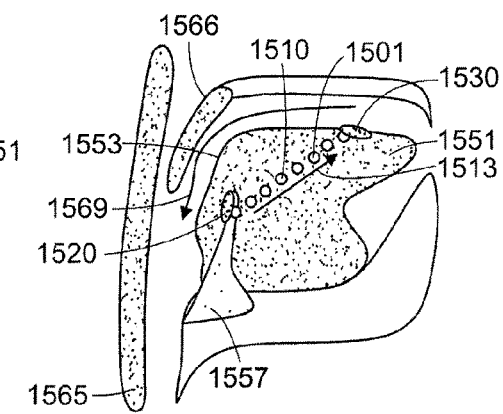

In a further embodiment, referring now to FIG. 15F, the retractor member 1520 sits against the PGF 1557, a portion of the shaft 1510 passes through the PGF 1557 and another portion of the shaft 1510 passes through the tongue 1551 medially and superiorly to an anchor member 1530 on the superior surface of the tongue 1551. In some embodiments, the anchor member 1530 is the tongue stud of a common non-medical tongue piercing and one end of the shaft couples to the anchor member 1530 (i.e., the tongue stud). For example, in some embodiments, an end of the shaft 1510 contains a material that attracts to the tongue stud such as, for example, a magnet that attracts to the tongue stud. In other embodiments, an end of the shaft 1510 has a hook or a loop that couples with all or a portion of the anchor member 1530 (e.g., a tongue stud). This movement of the PGF 1557 by the tissue retractor avoids movement of the tongue base 1553 toward the pharyngeal wall 1565 and/or the soft palate 1566. In this way, the airway airflow 1569 is maintained open and free from obstruction (or the sensation of obstruction).

Figure 16A:
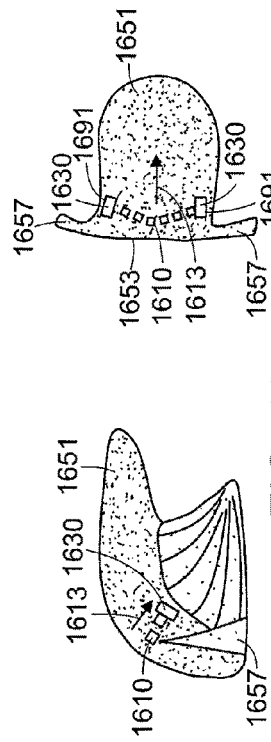
FIGS. 16A-16F illustrate Pharyngoglossal Fold embodiments.

In some embodiments, referring to FIG. 16A, a retractor member 1620 is disposed in the tongue base 1653. An anchor member 1630 is disposed in each PGF 1657. For example, in one embodiment, an anchor member 1630 is disposed in the anterior (i.e., the front) of each PGF 1657. A shaft 1610 connects each anchor member 1630 to the retractor member 1620 such that a first shaft 1610 is disposed between the anchor member 1630 disposed in the first PGF 1657 and the retractor member 1620 and a second shaft 1610 is disposed between the anchor member 1630 disposed in the second PGF and the retractor member 1620. The first shaft 1610 and the second shaft 1510 may be inside the tongue 1651, i.e., they may be sub-mucosal. In some embodiments, there is a single shaft 1610 with a first end connected to the first anchor member 1630, a second end connected to the second anchor member 1630, and a portion of the shaft 1610 contacts the retractor member 1620. The single shaft 1610 may be sub-mucosal or, alternatively, it may be on the exterior surface of the tongue 1651. In another embodiment, the retractor member 1620 is implanted at the tongue base 1653 and connects to two shafts 1610, one shaft 1610 is placed at the first PGF 1657 and the other shaft 1610 is placed at the second PGF 1657.

Figure 16B:
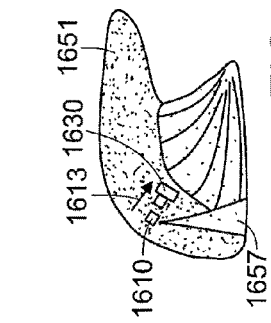

In some embodiments, referring to FIG. 16B, an anchor member 1630 is disposed in each PGF 1657. For example, in one embodiment, an anchor member 1630 is disposed in the anterior (i.e., the front) of each PGF 1657. A single shaft 1610 connects to each anchor member 1630 such that a first end of the shaft 1610 connects to an anchor member 1630 disposed in the first PGF 1657 and the second end of the shaft 1610 connects to an anchor member 1630 disposed in the second PGF 1657. At least a portion of the shaft 1610 is disposed substantially adjacent the base 1653 of the tongue 1651 and the shaft 1610 can be exterior to the tongue 1651. Alternatively, all or a portion of the shaft 1610 may be inside the tongue 1651, i.e., it may be sub-mucosal.

Figure 16C:
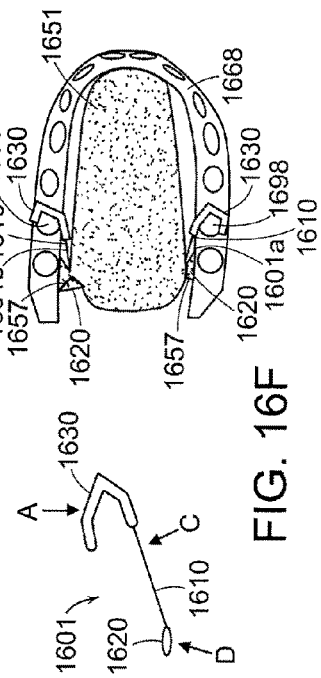

In some embodiments, referring now to FIG. 16C, an anchor member 1630 is implanted in or near each PGF 1657. A single shaft 1610 connects to each anchor member 1630 such that a first end of the shaft 1610 connects to an anchor member 1630 disposed in or near the first PGF 1657 and the second end of the shaft 1610 connects to an anchor member 1630 disposed in or near the second PGF 1657. At least a portion of the shaft 1610 is disposed substantially adjacent the base 1653 of the tongue 1651 and the shaft 1610 can be exterior to the tongue 1651. Alternatively, all or a portion of the shaft 1610 may be inside the tongue 1651, i.e., it may be sub-mucosal. In one embodiment, the two anchor members 1630 are each anterior to the two PGF's 1657.

Figure 16D:
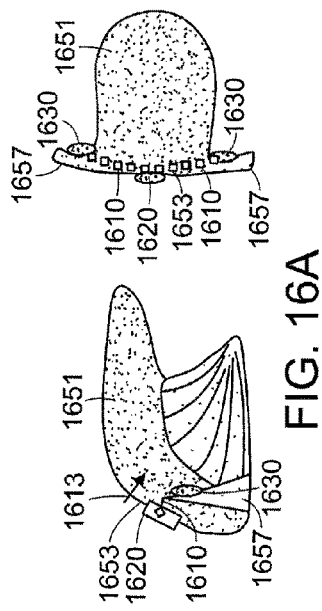

In a further embodiment, referring now to FIG. 16D, an anchor member 1630 is implanted in or near each PGF 1657 and each anchor member 1630 is a magnet 1691 or other nonferrous material. A single shaft 1610 connects to each anchor member 1630 such that a first end of the shaft 1610 connects to an anchor member 1630 disposed in or near the first PGF 1657 and the second end of the shaft 1610 connects to an anchor member 1630 disposed in or near the second PGF 1657. In one embodiment each end of the shaft 1610 includes a magnet or other material that has a polarity opposite to the polarity of the anchor member 1630 implanted at or near the PGF's. At least a portion of the shaft 1610 is disposed substantially adjacent the base 1653 of the tongue 1651 and the shaft 1610 can be exterior to the tongue 1651. Alternatively, all or a portion of the shaft 1610 may be inside the tongue 1651, i.e., it may be sub-mucosal. In one embodiment, the two anchor members 1630 are each anterior to the two PGF's 1657. In some embodiments, external structures having a polarity opposite the implanted anchor members 1630 (e.g., the magnets 1691) are employed to bond the implanted anchor member 1630*s* to the external structures. For example, a dental appliance or insert such as a mouth guard can contain a region that attracts to the implanted anchor members 1630 and that moves the PGF 1657 or the region of the PGF 1657 in a desired direction. Such methods move the PGF 1657 in the retraction direction 1613, which opens up and prevents obstruction of the patient's airway. A patient can use the dental appliance at night to alleviate symptoms associated with breathing disorders including, for example, sleep apnea.

Figure 16E:
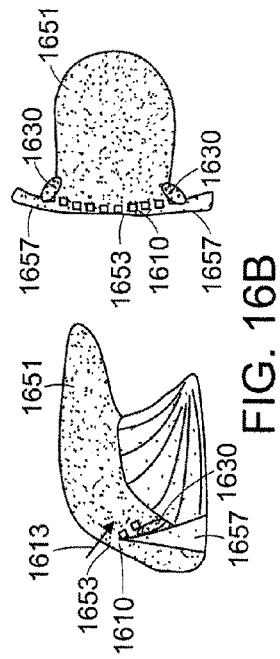

Referring now to FIG. 16E (two figures on the left), in some embodiments, a retractor member 1620 can be implanted in the PGF 1657. The retractor member 1620 can be a magnet 1691 implanted in a PGF 1657 that is retracted by a magnet 1691 or other material of opposite polarity. The magnet 1691 of opposite polarity can be attached to a modified anchor, for example. A variety of coupling mechanisms could be used to retain the retractor member 1620 magnet 1691 within the PGF 1657.

Referring now to FIG. 16E (two figures on the right) a retractor member 1620 can be an implanted magnet 1691 enclosed that has two flanges to keep the magnet 1691 in place within the PGF 1657. For example, the retractor member 1620 can have a flange surface near its posterior aspect that would provide the interface against the PGF 1657 to cause anterior retraction of the PGF 1657. The flange surface can have a rim that forms an edge around a portion of the PGF 1657 that is being retracted.

In another embodiment, the retractor member 1620 has a first flange with an exterior edge and an interior shaft, the interior shaft can have a first conduit. The second flange can likewise have an exterior edge and an interior shaft having a second conduit. When the retractor member 1620 is implanted in the PGF 1657 the first flange is adjacent the posterior aspect and the interior shaft pierces the PGF to provide a first conduit that flows through the PGF 1657 the second flange interior shaft mates with first flange interior shaft and the second flange is adjacent the anterior aspect. Thus the first conduit and the second conduit of the retractor member 1620 cut through the PGF 1657 and provide a single conduit through the PGF 1657.

Referring to FIG. 16E (the two figures on the left and the two figures on the right) where magnets 1691 are implanted within each PGF 1657 external modified anchors with magnets or other materials of opposite polarity may be used to bond to the implanted magnets 1691 and to anchor them to external structures. Suitable external modified anchors can include, for example, a dental appliance or insert such as a mouth guard that has a region that attracts to the implanted magnets 1691. This embodiment is minimally invasive and allows the patient a very high degree of comfort during the day when the implant is unconnected and therefore unloaded (e.g., when the modified anchor is not inserted in the patient's mouth). Suitable modified anchors can include various shaft and anchor combinations. A variety of external modified anchors can be tested without needing to replace the retractor member implant (e.g., the magnet 1691).

In some embodiments, a tissue retractor 1601 is employed in the region of the PGF 1657 such that the anchor member 1630 of the tissue retractor 1601 is coupled to a dental anchor (e.g., the anchor member 1630 is coupled to the patient's tooth 1698 or other dental structure in the patient's mouth). The anchor member 1630 could be a full loop, a partial loop, or a hook that anchors to the tooth 1698 or to a palatal prosthesis. The tissue retractor 1601 retractor member 1620 couples to the PGF 1657 using magnets or other mechanical mechanisms known in the art. In some embodiments, the dental anchor is employed to retract the PGF 1657. An advantage of this device is that the PGF 1657 is very close to the mandibular teeth and a secure but reversible loading of the implanted tissue retractor 1601 between the PGF 1657 and the teeth 1698 can therefore be achieved with short devices. Moreover, due in part to the relatively short route from the PGF 1657 to the molar teeth 1698 the tissue retractor 1601 is unlikely to cause the patient significant discomfort.

Figure 16F:
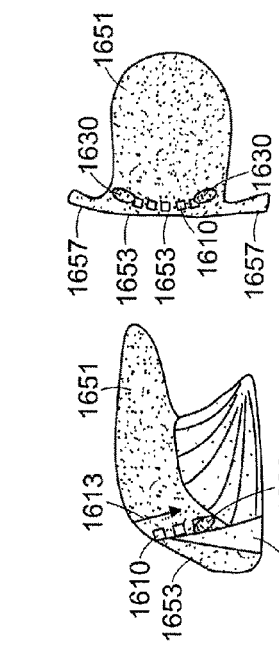

FIG. 16F (on the left) shows a schematic of a tissue retractor 1601 having an anchor member 1630 that aligns with a dental type modified anchor. The anchor member 1630 reversibly attaches to teeth 1698 as shown on right. A shaft 1610 of variable length attaches to a retractor member 1620 (e.g., a coupling mechanism) that in turn connects to an implant in the mouth. The implant can be a magnet that is positioned at or near the PGF 1657. For example, the retractor member 1620 may be a magnet or a mechanical mechanism. FIG. 16F (on the right) depicts a drawing of a tongue and a mandible as seen from above.

FIG. 16F (on the right) shows a tissue retractor 1601a having a magnet implanted at or near the PGF 1657 the implanted magnet is attracted to an end of the shaft 1610 that is coupled to a retractor member 1630 that surrounds the patient's tooth 1698. In one embodiment, the end of the shaft 1610 has a magnet that is attracted to the magnet implanted at or near the PGF 1657. FIG. 16F (on the right) also shows the tissue retractor 1601b that acts to mechanically hook the PGF 1657, which is described in greater detail in FIG. 21H in association with the tissue retractor 2101. Referring now to FIGS. 16A-16F forces on the retractor member 1620, anchor member 1630, and/or shaft 1610 improve the patient's airway in a manner that prevents obstruction (e.g., prevents actual obstruction and/or prevents an airway size reduction that produces the sensation in the patient that the airway is obstructed to airflow). In some embodiments, the PGF 1657 is moved in a direction that opens up the patient's airway and prevents obstruction of the patient's airway to airflow. In some embodiments, soft tissue movement toward the pharyngeal wall and/or the soft palate is avoided. In other embodiments, the tongue base 1653 is moved in a direction away from the pharyngeal wall and/or the soft palate.

All of a portion of the tissue retractors described herein may be coupled to structures such as, for example, the PGF, the area lateral to the PGF, the styloglossus, hyoglossus, chondroglossus, pharyngeal constrictor, levator and tensor of the palate, masetter, temporalis, pterygoid, facial, and platysma muscles; the hyoid, mandible, facial, and vertebral bones; the thyroid, cricoid, epiglottic cartilages; the stylohyoid, ptyrogomandibular ligaments, and other fascial structures.

8. Soft Palate and Tonsillar Folds

Figure 17A:
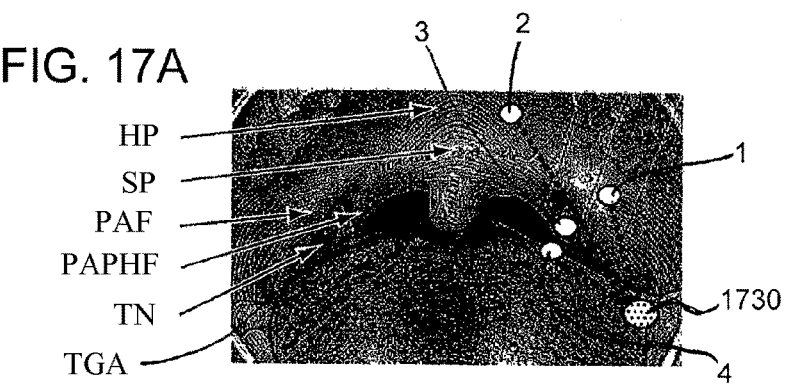
FIGS. 17A-17C illustrate Soft Palate embodiments.
Figure 17B:
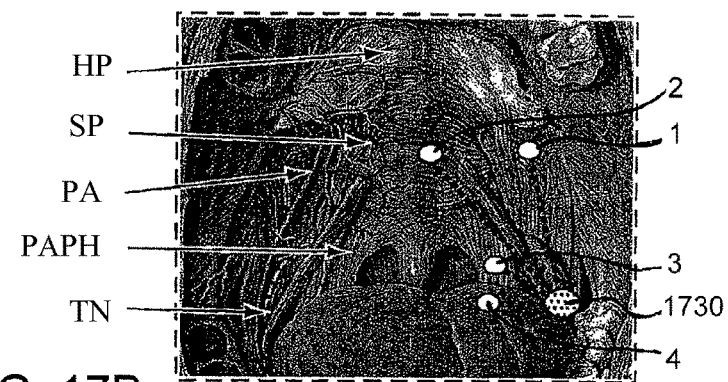
Figure 17C:
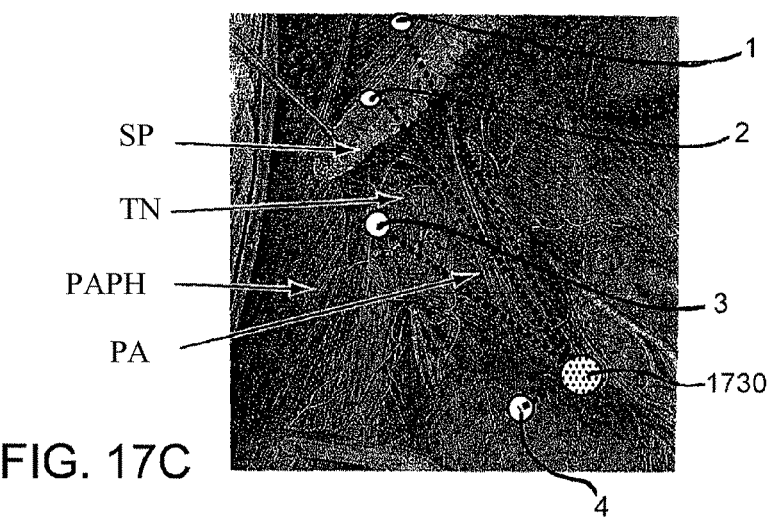

Disclosed here are methods and devices for retracting the lateral pharyngeal walls and soft palate. FIGS. 17A-17C show the basic anatomy of the internal soft palate structures and some embodiments employing tissue retractors to retract portions of the soft palate. The soft palate is a thin muscular structure that separates the nasopharynx and velopharynx from the oral cavity. It begins at the edge of the hard palate and extends downward toward the throat. In the midline it ends at the uvula, and on each side it divides into two folds that surround the palatine tonsils: the anterior tonsillar fold, also called the palatoglossal fold, inserts into the side of the tongue near the superior PGF; the posterior tonsillar fold, also called the palatopharyngeal fold (PAPHF), inserts into the lateral pharyngeal wall.

Excess length or thickness of the soft palate decrease the volume of the velopharynx and contribute to snoring and sleep apnea. In addition, laxity of the soft palate and laxity of the pharyngeal walls predisposes a patient's airway to airway collapse. Tissue retractors and methods employing tissue retractors can reversibly or persistently thin, stiffen, and/or retract the soft palate and pharyngeal wall structure to avoid obstruction of the patient's airway.

Tissue retractors can be employed in a portion of the soft palate in a manner similar to tissue retractor placement in the tongue or the PGF, for example. In accordance with one tissue retraction method, an anchor member is disposed external the PGF, a shaft is disposed through the PGF and through the soft palate, and the retractor is on an external surface of the soft palate. Specifically, a tissue retractor placed in the soft palate could rest in place unloaded with a minimum tension (e.g., from about 1 gm to about 100 gm, or from about 5 gm to about 15 gm) that is sufficient to keep the shaft within the soft palate tissue with the anchor member and/or retractor member resting against the mucosa (e.g., against the external surface of the soft palate). The patient would therefore have little or no sensation of the presence of the tissue retractor. During the time for sleep (e.g., at night) the tissue retractor could be "loaded" (e.g., the tension exerted on the tissue retractor could be increased to from about 1 gm to about 1000 gm, or from about 5 gm to about 100 gm). In some embodiments, the tissue retractor is loaded by placing a modified anchor (e.g., a bolster) between the anchor and the mucosa. In other embodiments, the tissue retractor is loaded when it is connected to a dental anchor (e.g., a dental device like a retainer or mouth guard, a tooth, or a dental implant). The exact site and orientation of the lateral tissue retractor has a great influence on whether the effects of the tissue retractor are primarily to compress or to displace tissue.

FIGS. 17A-17C show different views of four exemplary tissue retractor positions where each of the four tissue retractors has an anchor member 1730 positioned in the same anchor site, at the superior PGF. The remaining portions of each of the four tissue retractors (i.e., the shaft and retractor member) has a different placement position and each of the four tissue retractor has a different beneficial effect. Generally, at least a portion of the shaft is disposed inside the tissue of the soft palate.

FIG. 17A is a view of the mouth showing the soft palate and palatoglossal folds. FIG. 17B is the same view as FIG. 17A, but with mucosa removed showing the underlying muscles (right side) and the nerve and blood supply (left side). FIG. 17C show the view of the left lateral pharyngeal wall area after mid-sagittal section of FIG. 17B and the tongue is retracted inferiorly. Four positions for placement of tissue retractors are shown, in each of the four positions an anchor member 1730 is positioned in the superior PGF. In position 1 the shaft passes next to palatoglossus muscle around the tonsil, the retractor rest against lateral edge of soft palate. This embodiment increases the lateral velopharyngeal area. Position 1 is oriented to achieve inferior displacement of the lateral aspect of the soft palate, thereby enlarging the velopharynx.

In position 2 the shaft travels within the palatoglossus muscle, the retractor is near the midline soft palate. This embodiment increases medial velopharyngeal airspace. In position the tissue retractor passes to the midline of the soft palate. The exact location, force and number of tissue retractors can be varied in order to best treat the specific pathology of each patient In position 3 the shaft passes through the palatoglossus muscle, the palatine tonsil, and the palatopharyngeus muscle, the retractor rests against the posterior wall of the soft palate. This embodiment compresses and permanently remodels the palatine tonsil. In position 3 the tissue retractor passes across the tonsil to a retractor on the pharyngeal side of the posterior tonsillar pillar. The tonsils in sleep apnea patients often are enlarged relative to the tonsils in individuals who do not suffer from sleep apnea and this enlargement contributes to the excess soft tissue of the upper airway. Tension in the shaft would compress and the tonsils and decrease their volume.

In position 4 the shaft passes 1 cm under the tongue base mucosa and the retractor rests against tongue base. This position of tissue retractor placement can be employed for tensing the tongue base. In position 4 the tissue retractor passes from the superior PGF to the mucosa of the tongue base. This embodiment stiffens the mucosa of the tongue base and prevents the tongue base from deforming backward.

Referring now to FIGS. 15-17, a method for treatment of a breathing disorder includes positioning a shaft having a first end and a second end in a patient's oral cavity or pharynx and connecting one of a retractor member and an anchor member at or near the first end and in the region of the pharyngoglossal fold. The other of the retractor member and the anchor member is connected at or near the second end of the shaft. At least one of the shaft, the retractor member, and the anchor member interact to distribute a force on at least one of a tongue base, a lateral paryngeal wall, a tonsillar fold, or a soft palate and the force prevents obstruction of the patient's airway. Optionally at least a portion of the retractor member or at least a portion of the anchor member is positioned: on an external surface of the pharyngoglossal fold or behind the pharyngoglossal fold. In one embodiment, at least a portion of the retractor member or at least a portion of the anchor member is disposed inside the region of the pharyngoglossal fold. In some embodiments, the first end of the shaft comprises a first magnet and one of the retractor member and the anchor member comprises a second magnet or a ferrous material that attracts to the first magnet. In some embodiments, the retractor member is in the region of the pharyngoglossal fold and the anchor member couples to a tooth. In some embodiments, at least a portion of the shaft is internal to at least one of the pharyngoglossal fold and a tongue. Optionally, at least a portion of the anchor member or at least a portion of the retractor member is positioned inside the patient's mouth, in the region of the patient's frenulum, external to the patient's mouth, adjacent a surface of a tongue, inside a tongue, or external to a soft palate.

Referring still to FIGS. 15-17, a tissue retractor for treatment of a breathing disorder can include a retractor member having a first magnet, a shaft sized for placement in a patient's oral cavity or pharynx with a first end of the shaft having a second magnet or other material that attracts to the first magnet, and an anchor member connected at or near the second end of the shaft. At least one of the shaft, the retractor member and the anchor member interact to distribute a force on a soft tissue in the patient's oral cavity or pharynx, and the force prevents obstruction of the patient's airway. The anchor member can couple to a tooth, for example, the anchor member can surround at least a portion of the tooth.

Figure 18A:
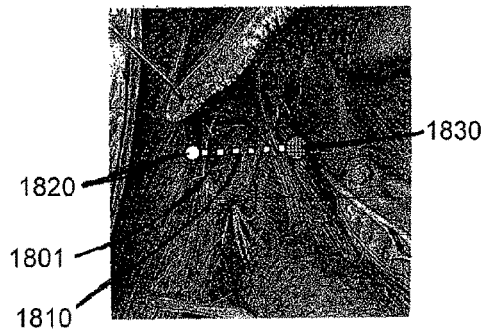
FIGS. 18A-18F illustrate Tonsillar Fold embodiments.
Figure 18B:
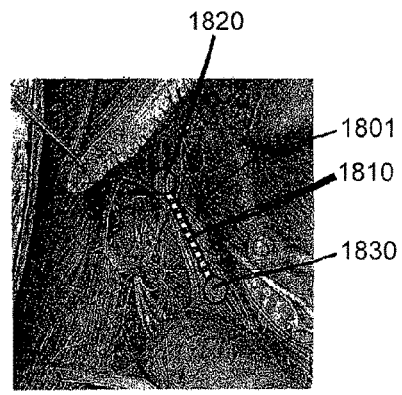

FIGS. 18A-18F show a variety of methods for treatment of a breathing disorder employing a tissue retractor 1801 in the tonsillar folds. Referring to FIG. 18A, a tissue retractor 1801 includes a retractor member 1820 connected to a first end of a shaft 1810 and an anchor member 1830 connected to a second end of the shaft 1810. The retractor member 1820 is on the posterior surface of posterior tonsillar fold, at least a portion of the shaft 1810 is inside the tissue of the soft palate, and the anchor member 1830 is positioned on the anterior surface of anterior tonsillar fold. The tissue retractor 1801 placement shown in FIG. 18A compresses the palatine tonsil. Referring now to FIG. 18B, the retractor member 1820 is in the superior Palatoglossus fold an anchor member 1830 is in the inferior Palatoglossus Fold or PGF. A shaft 1810 connects the retractor member 1820 to the anchor member 1830.

Figure 18C:
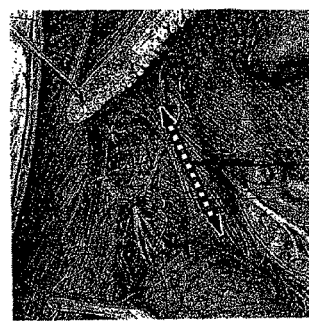
Figure 18D:
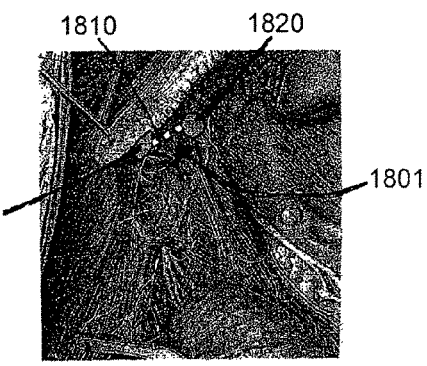
Figure 18E:
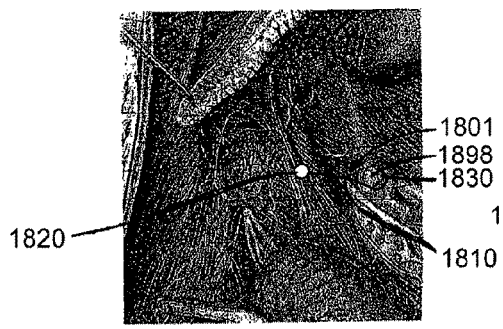
Figure 18F:
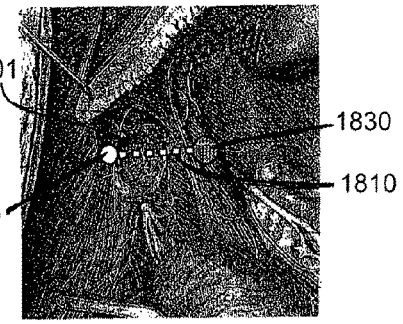

Referring now to FIG. 18C, the tissue retractor 1801 is implanted within the palatoglossus muscle, this fully implanted tissue retractor 1801 including an anchor member and a retractor member connected by a shaft is implanted in non tongue tissue for treatment of breathing disorders. In one embodiment, the inferior end of the tissue retractor 1801 is the anchor member and the superior end of the tissue retractor 1801 is the retractor member. Referring now to FIG. 18D, the anchor member 1830 is positioned at the lateral portion of the soft palate, at least a portion of the shaft 1810 is positioned inside the tissue of the soft palate, and the retractor member 1820 is positioned at the midline of the soft palate. Referring now to FIG. 18E, the tissue retractor 1801 has a retractor member 1820 on the inner surface of the palatoglossal fold and the tissue retractors anchor member 1830 is a modified dental anchor that couples to a patient's tooth 1898. In one embodiment, the anchor member 1830 surrounds a portion of the patient's tooth 1898. For example, the anchor member 1830 can have the shape of a hook that surrounds only a portion of the patient's tooth 1898. All or a portion of the shaft 1810 may be inside the soft palate tissue. Alternatively, both the shaft 1810 and the anchor member 1830 are external to the soft palate tissue. Referring now to FIG. 18F, the tissue retractor 1801 has a retractor member 1820 that is located posterior to the tonsillar fold, at least a portion of the shaft 1810 is inside the tissue of the soft palate, and the anchor member 1830 is anterior the tonsillar fold. The tongue, the lateral pharyngeal walls, and the soft palate can alone or in combination contribue to obstructions related to breathing disoreders such as sleep apnea. More specifically, the lateral pharyngeal walls and the soft palate contribute extra soft tissue that decreases the volume of the velopharyngeal airspace. In patients that suffer from breathing disorders such as obstructive sleep apnea the lateral pharyngeal walls and the soft palate can become flaccid. Suitable tissue retractors can be employed to retract and/or tighten the soft tissue in the lateral pharyngeal walls and the soft palate thereby enabling patentcy of the patient's airway. In some embodiments, all or a portion of the patient's tonsils are compressed, thereby directly decreasing the volume of the patients tissue by, for example, tissue remodeling.

Referring now to FIGS. 18A-18F, a method for treatment of a breathing disorder includes implanting into a tonsillar fold in a patient's oral cavity or pharynx a shaft 1810 with a retractor member 1820 connected at a first end and an anchor member 1830 connected at a second end. At least one of the shaft 1810, the retractor member 1820, and the anchor member 1830 interact to distribute a force on a soft tissue in the patient's oral cavity or pharynx. The force exerted on the soft tissue prevents obstruction of the patient's airway.

Referring still to FIGS. 18A-18F, a method for treatment of a breathing disorder includes implanting at least a portion of a shaft 1810 having a first end and a second end into a tonsillar fold in a patient's oral cavity or pharynx. One of a retractor member 1820 and an anchor member 1830 is connected at or near the first end of the shaft 1810 and the other of the retractor member 1820 and the anchor member 1830 are connected at or near the second end of the shaft 1810. At least one of the retractor member 1820 and the anchor member 1830 is external to the tonsillar fold and at least one of the shaft 1810, the retractor member 1820, and the anchor member 1830 interact to distribute a force that prevents obstruction of the patient's airway. In one embodiment, the force pushes at least a portion of the soft palate to open at least a portion of the patient's airway. In some embodiments, the anchor member 1830 surrounds at least a portion of the patient's tooth 1898. In some embodiments, the anchor member 1830 is external to an anterior tonsillar fold.

FIGS. 19A-19F show embodiments for treatment of a breathing disorder in which a tissue retractor 1901 is disposed in a patient's soft palate 1966. FIG. 19A shows an embodiment of a midline tissue retractor 1901 disposed in the soft palate 1966 with an anchor member 1930 disposed on the pharyngeal side 19661 near the hard palate. The shaft 1910 passes through soft tissue of the soft palate 1966, and the retractor member 1920 head is in the uvular area (FIG. 18D). The retractor member 1920 is disposed on the oral side 19662 of the soft palate 1966. In one embodiment, the anchor member 1930 is disposed on the superior pharyngeal side 19661 and the retractor member 1920 is on the inferior oral side 19662. The retractor member 1920 can be inserted so that it faces any of the forward, downward or backward direction. The anchor member 1920 can rest against the mucosa on the pharyngeal side 19661. The anchor member 1930 can be available to couple to a modified anchor on the pharyngeal side 19661 of the soft palate 1966. The modified anchor can be, for example, an implant disposed in the pharyngeal wall.

FIG. 19B shows a tissue retractor 1901 disposed in the soft palate 1966 with an anchor member 1930 disposed on the inferior pharyngeal side 19661, the shaft 1910 passes through soft tissue of the soft palate 1966, and the retractor member 1920 is disposed on the superior oral side 19662 of the soft palate 1966. The retractor member 1920 could be inserted so it faces either forward, downward or backward. Optionally, the anchor member 1930 could rest against the mucosa on either the oral side 19662 or the pharyngeal side 19661. The anchor member 1930 would be available to couple to a modified anchor such as a dental appliance on the oral side 19662 or a modified anchor on the pharyngeal side 19661.

FIG. 19C shows the effect of a modified anchor on the shape and position of the soft palate 1966. The modified anchor can be used in conjunction with a tissue retractor 1901. In one embodiment, the modified anchor is a bolster 1940. The tissue retractor 1901 is disposed in a patient's soft palate 1966 such that a shaft 1910 passes through the soft tissue of the soft palate 1966, the retractor member 1920 is connected at or near a first end of the shaft 1910 and the anchor member 1930 is connected at or near a second end of the shaft 1910. At least one of the anchor member 1930 and the retractor member 1920 is disposed on an external surface of the soft palate 1966. The bolster 1940 is, in one embodiment, disposed between the external surface of the patient's soft palate 1966 and the anchor member 1930. In one embodiment, the bolster 1940 has a recess in its surface that is designed to allow the anchor member 1930 head to fit into the bolster 1940 recess, such that after insertion the combined anchor member 1930 and bolster 1940 presents a smooth and soft continuous surface. The surface of the combination bolster 1940 and anchor member 1930 avoids effect on speech and/or swallowing and causes minimal discomfort to the patient. The bolster 1940 rotates, stiffens, and indents the soft palate 1966 all of which serves to decrease the patient's susceptibility to snoring and airway obstruction. The amount of tension added by the bolster 1940 ranges from about 1 gm to about about 500 gms, from about 5 gms to about 250 gms, or from about 10 gms to about 50 gms. Additional of the bolster 1940 to the tissue retractor 1901 can, in one embodiment, "load" the tissue retractor 1901 so that the "loaded" tissue retractor 1901 prevents obstruction of the patient's airway.

FIG. 19D shows another embodiment of a tissue retractor 1901 disposed in the patient's soft palate 1966. The tissue retractor 1901 is implanted in the patient's soft palate 1966. The tissue retractor 1901 includes a shaft with a retractor member connected at or near a first end and an anchor member connected at or near a second end. In one embodiment of the implanted tissue retractor 1901 the anchor member is superior to the retractor member. In another embodiment of the implanted tissue retractor 1901, the retractor member is superior to the anchor member.

FIG. 19E shows an embodiment of a tissue retractor 1901 where the anchor member and the retractor member are both disposed on the external surface of the soft palate 1966 and each of the anchor member and the retractor member are aligned on either side of the soft palate 1966 (i.e., the retractor member opposes the anchor member and the shaft is disposed through the soft tissue of the soft palate 1966). In one embodiment, the aligned anchor member and retractor member of the tissue retractor 1901 are employed to compress a thickened soft palate 1966. Each of the anchor member and the retractor member of the tissue retractor 1901 provide tension along the tissue retractor 1901 shaft that compresses and thins the soft palate 1966 tissue that lies between the anchor member and the retractor member.

FIG. 19F, shows an embodiment of a tissue retractor 1901 where the anchor member and the retractor member are both disposed on the external surface of the soft palate 1966 and each of the anchor member and the retractor member are aligned on either side of the soft palate 1966 (i.e., the retractor member opposes the anchor member and the shaft is disposed through the soft tissue of the soft palate 1966). One or more band 1970 is adjacent the external surface of the soft palate 1966, for example, the band(s) 1970 are adjacent the edge of the soft palate 1966 with a first end of the band 1970 substantially adjacent the anchor member and a second end of the band 1970 substantially adjacent the retractor member of the tissue retractor 1901. For example, in one embodiment, the first end of the band 1970 is disposed between the anchor member and the external surface of the soft palate 1966, optionally, a portion of the shaft external to the soft tissue is placed through an aperture disposed in the first end of the band 1970. Likewise, the second end of the band 1970 is disposed between the retractor member and the external surface of the soft palate 1966 and another portion of the shaft external to the soft tissue is placed through an aperture disposed in the second end of the band 1970. Alternatively, each end of the band 1970 is held between the anchor member and the soft tissue and the retractor member and the soft tissue by compressive force.

Referring to FIGS. 19A-19F, a method for treatment of a breathing disorder includes inserting a shaft 1910 into a soft palate 1966 located in a patient's oral cavity or pharynx, connecting a retractor member 1920 at or near a first end of the shaft 1910, and connecting an anchor member 1930 at or near a second end of the shaft 1910. At least one of the shaft 1910, the retractor member 1920, and the anchor member 1930 interact to exert a pressure that prevents deformation of a portion of the soft palate 1966 to prevent obstruction of the patient's airway. In one embodiment, at least one of the retractor member 1920 or the anchor member 1930 is on an external surface of the soft palate 1966. In some embodiments, the method employs a band 1970, a first end of the band 1970 connects at or near the retractor member 1920, a second end of the band 1970 connects at or near the anchor member 1930, and the band 1970 externally surrounds at least a portion of the soft palate 1966. At least one of the shaft 1910, the retractor member 1920, the anchor member 1930, and the band 1970 interact to exert a pressure that prevents deformation of a portion of the soft palate 1966 to prevent obstruction of the patient's airway. The pressure that prevents deformation of a portion of the soft palate 1966 avoids the tissue of the soft palate from moving toward regions of soft tissue within the patient's oral cavity or pharynx, for example, a portion of the tissue of the soft palate 1966 does not move toward the patient's tongue. The portion of the soft palate 1966 is retrained from being displaced and deformed to retrict and/or close the patient's airway. Optionally, the method includes disposing a bolster 1940 on an external surface of the soft palate 1966 between the external surface of the soft palate 1966 and one of the retractor member 1920 and the anchor member 1930.

Referring still to FIGS. 19A-19F, a tissue retractor 1901 for treatment of at least one of snoring and sleep apnea includes a shaft 1910 sized for insertion into a patient's soft tissue, a retractor member 1920 connected at or near a first end of the shaft 1910, the retractor member 1920 positioned on an external surface of the patient's soft tissue, an anchor member 1930 connected at or near a second end of the shaft 1910, and a band 1970. The band 1970 is sized to surround at least a portion of the external diameter of the patient's soft tissue, a first end of the band 1970 is connected at or near the retractor member 1920, and a second end of the band 1970 is connected at or near the anchor member 1930. At least one of the shaft 1910, the retractor member 1920, the anchor member 1930, and the band 1970 interact to exert a pressure that prevents deformation of a portion of the soft tissue to prevent obstruction of the patient's airway. In one embodiment of the tissue retractor 1901, the anchor member 1930 is positioned on an external surface of the patient's soft tissue.

9. Veterinarian Embodiments

Figure 20A:
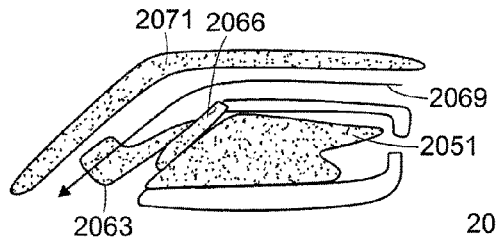
FIGS. 20A-20G illustrate Veterinarian embodiments.
Figure 20E:
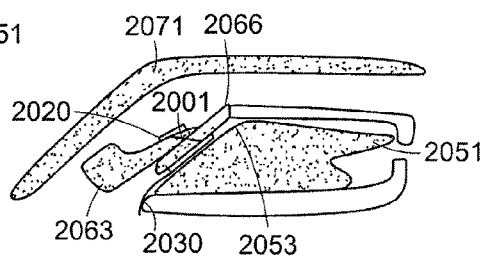

Referring now to FIGS. 20A-20G disclosed here are methods and devices to treat sleep apnea and related disorders in mammals such as, for example, horses. A non-limiting example of an non-human upper airway disorder is dorsal displacement of the soft palate (DDSP) in horses. Race horses are superb animal athletes that place the greatest demands on respiration. All non-human mammals have a different configuration of their upper airways. FIG. 20A shows the normal configuration of the horse upper airway during exercise. The soft palate 2066 overlaps and interlocks the epiglottis 2063 of the larynx to provide an open conduit for airflow 2069 in the pharynx air space. Referring still to FIG. 20A, specifically the soft palate 2066 and larynx are much closer and they usually interlock. Specifically, the soft palate 2066 is firmly held around the epiglottis 2063 of the larynx so that the airway flow from the nose through the posterior pharyngeal wall 2071 and into the lungs is protected and secure. In race horses this is of special importance because of the tremendous volume of air that must smoothly flow into and out of the lungs with each breath during exercise.

Figure 20B:
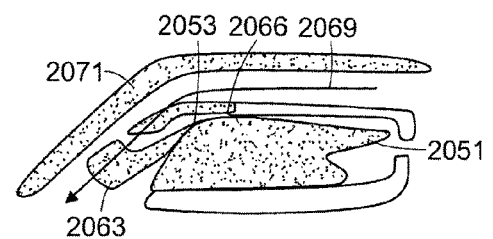

Referring now to FIG. 20B, in some horses this interlocking of the soft palate 2066 and epiglottis 2063 breaks down and the soft palate 2066 passes backward over the epiglottis 2063. In DDSP the soft palate 2066 is dislodged from its locked position and obstructs the airway to airflow 2069. This displacement of the soft palate 2066 immediately interferes with breathing and then the animal stops running. Although the cause of DDSP is not known with certainty, many trainers believe that the tongue 2051 causes the displacement by moving backward and pushing the soft palate 2066 out of position. The displacement is believed to be caused by the backward movement of the tongue base 2053. For this reason many trainers actually tie the race horse's tongue 2051 forward prior to the race, a solution that is crude and uncomfortable for the animal.

Methods and devices are employed to prevent DDSP both by preventing backward displacement of the tongue 2051 and by securely coupling the soft palate 2066 to the epiglottis 2063. In humans, the conditions surrounding sleep disordered breathing involve a relaxed tongue 2051 during sleep. In horses the situation is quite different: the tongue 2051 and other upper airway structures are much larger and are maximally active. Therefore, the tissue retractor 2001 (e.g., the LTR) must be adapted to these harsher conditions. Moreover, in horses secure prevention of backward movement of the tongue 2051 does not allow normal swallowing. Therefore it is necessary that the tissue retractor 2001 be used only when necessary to avoid upper airway obstruction (e.g., DDSP). For example, the tissue retractor 2001 can be loaded immediately before exercise and then unloaded immediately after exercise. Moreover the loading and unloading of the tissue retractor 2001 needs to be done by the trainer, with or without the cooperation of the horse.

Figure 20F:
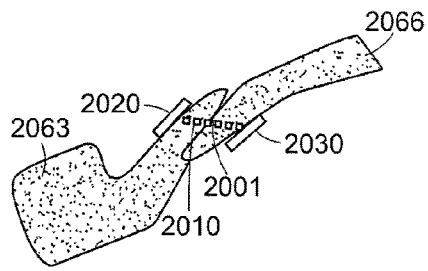
Figure 20C:
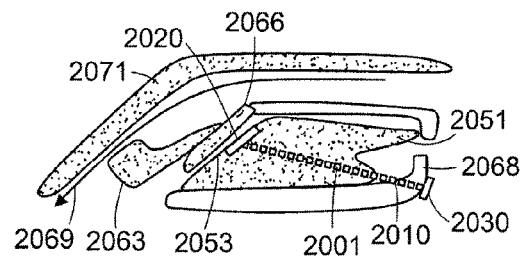
Figure 20D:
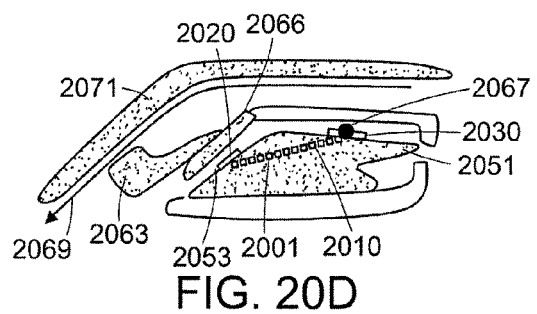

Referring now to FIGS. 20C-20D, in some embodiments, a tissue retractor 2001 (e.g., an LTR) is used to prevent movement of the tongue 2051 backwards preventing backward movement of the tongue 2051 prevents dorsal displacement of the soft palate 2066 in a horse. The situation in the breathing disordered equine patient differs in many substantial ways from that of the breathing disordered human. In horses, the problem occurs when the animal is awake and exercising at its full capacity. It is believed that the tongue 2051 base 2053 moves backward and pushes the soft palate 2066 out of its normal position where it is interlocked with the epiglottis 2063 (this is shown in FIG. 20B). Therefore the tongue 2051 retracting forces needed in horses are much higher than the tongue retracting force used in humans. For example, the amount of force employed to retract the horses tongue 2051 ranges from about 1 gm to about 50 Kg, from about 10 gm to about 10 Kg, or from about 100 gm to about 1 Kg. To accommodate and/or exert these high forces the tissue retractor 2001 used in horses employs materials such as, for example, stainless steel or materials of comparable tensile strength to stainless steel.

In some embodiments, referring now to FIG. 20C, the tissue retractor 2001 spans from the tongue base 2053 through the mandible 2068 where the tissue retractor 2001 can be accessed inside of the horses lip. The retractor member 2020 is at the tongue base 2053, the retractor member 2020 connects to a first end of the shaft 2010. A portion of the shaft 2010 passes through the tongue 2051, a portion of the shaft 2010 passes through the mandible 2068, and the second end of the shaft connects to the anchor member 2030, which is adjacent the mandible 2068. In one embodiment, a portion of the shaft 2010 reaches through the mandible 2068 to an adjustable anchor member 2030 in front of the mandible 2068. Optionally, a bolster can be placed to load the tissue retractor 2001 prior to exercise. In one embodiment, a bolster is placed between the mandible 2068 and the anchor member 2030. In another embodiment, a bolster is placed between the tongue base 2053 and the retractor member 2020.

FIG. 20D shows an embodiment of the tissue retractor 2001 that takes advantage of certain unique circumstances present in horses. Specifically, a bridle is usually placed on the horse's head when racing to control the horse. Most bridle's have a bit 2067, a bar which passes across the horse's mouth. This bit 2067 can be used as modified anchor to couple to and load the tissue retractor 2001. Referring still to FIG. 20D, the tissue retractor 2001 passes from the tongue base 2053 to the superior surface of the tongue 2051. The tissue retractor 2001 is unloaded most of the time and only becomes loaded when it is connected to the bit 2067 of the horse's bridle prior to exercise. In one embodiment, the shaft 2010 connects to an anchor member 2030 on the tongue 2051 surface, which is reversibly attached to the bit 2067 of a bridle during exercise. The retractor member 2020 is at the tongue base 2053. Once the anchor member 2030 of the tissue retractor 2001 is loaded into the bit 2067, the tongue base 2053 is retracted by the retractor member 2020.

Figure 20G:
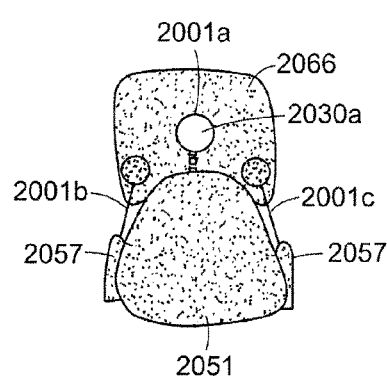

In some embodiments, referring now to FIGS. 20E-20F, the soft palate 2066 and the epiglottis 2063 are secured together. In some embodiments, a tissue retractor 2001 (i.e., an LTR) passes from the soft palate 2066 to the epiglottis 2063 to resist displacement of the soft palate 2066 and the epiglottis 2063. In other embodiments, the tissue retractor 2001 passes from the soft palate 2066 to the epiglottis 2063 and restores the interlocked configuration between the soft palate 2066 and the epiglottis 2063 if the two should become displaced. In one embodiment, referring now to FIGS. 20E-20F, a tissue retractor 2001 directly opposes dislodging the soft palate 2066 from its normal position. An anchor member 2030 is positioned in front of the soft palate 2066, a portion of the shaft 2010 passes backward through the soft palate 2066 and then another portion of the shaft 2010 passes through the epiglottis 2063 to a retractor member 2020 on the laryngeal surface of the epiglottis 2063. A first end of the shaft 2010 is connected at or near the anchor member 2030 and a second end of the shaft 2010 is connected at or near the retractor member 2020. Referring now to FIG. 20G, in one embodiment, a tissue retractor 2001b, 2001c is positioned through each PGF 2057 and each tissue retractor 2001b, 2001c attaches to a lateral aspect of the soft palate 2066. In addition, a tissue retractor 2001a (similar to the tissue retractor show in FIGS. 20E and 20F) may also be positioned to secure the soft palate 2066 and the epiglottis together.

Referring now to FIGS. 20A-20G, methods of treatment of a breathing disorder in a horse include, for example, inserting a shaft 2010 into a horses tongue 2051, connecting a retractor member 2020 at or near a first end of the shaft 2010, and connecting an anchor member 2030 at or near a second end of the shaft 2010. The anchor member 2030 is external to the horses mandible 2068. At least one of the shaft 2010, the retractor member 2020, and the anchor member 2030 interact to exert a pressure that prevents obstruction of the horses airway to airflow 2069. A tissue retractor 2001 for treatment of a breathing disorder in a horse can include a shaft 2010 sized for insertion into a horses tongue 2051, a retractor member 2020 connected at or near a first end of the shaft 2010, and an anchor member 2030 connected at or near a second end of the shaft 2010, the anchor member 2030 is external to the horses mandible 2068 and at least one of the shaft 2010, the retractor member 2020, and the anchor member 2030 interact to exert a pressure that prevents obstruction of the horses airway.

Referring now to FIG. 20D, some methods for treatment of a breathing disorder in a horse include inserting a shaft 2010 into a horses tongue 2051, connecting a retractor member 2020 at or near a first end of the shaft 2010, and connecting an anchor member 2030 at or near a second end of the shaft 2010, the anchor member 2030 is external to the horses tongue 2051. The anchor member 2030 is hooked to a bit 2067 of the horses bridal. Hooking the anchor member 2030 to the bit 2067 "loads" the tissue retractor 2001. At least one of the shaft 2010, the retractor member 2020, the anchor member 2030, and the bit 2067 interact to exert a pressure that prevents obstruction of the horses airway to airflow 2069. A tissue retractor for treatment of a breathing disorder in a horse includes a shaft 2010 sized for insertion into a horses tongue 2051, a retractor member 2020 connected at or near a first end of the shaft 2010, and an anchor member 2030 connected at or near a second end of the shaft 2010, the anchor member 2030 is external to the horses tongue 2051 and the anchor member 2030 hooks to a bit 2067 of a horses bridal. At least one of the shaft 2010, the retractor member 2020, the anchor member 2030, and the bit 2067 interact to exert a pressure that prevents obstruction of the horses airway to airflow 2069.

Referring now to FIGS. 20E-20F, a method for treatment of a breathing disorder in a horse includes inserting a shaft 2010 through an epiglottis 2063 and a soft palate 2066, connecting a retractor member 2020 at or near a first end of the shaft 2010, the retractor member 2020 is external to the soft palate 2066, and connecting an anchor member 2030 at or near a second end of the shaft 2010, the anchor member 2030 is external to the epiglottis 2063. At least one of the shaft 2010, the retractor member 2020, and the anchor member 2030 interact to maintain the epiglottis 2063 adjacent to the soft palate 2066 and to prevent obstruction of the horses airway.

The method for treatment can also include, referring now to FIG. 20G, positioning a first tissue retractor 2001a between the epiglottis and the soft palate 2066 and positioning a second tissue retractor 2001b such that a retractor member is in the region of the pharyngoglossal fold 2057 and at least a portion of the anchor member is attached to the soft palate 2066. Optionally, a third tissue retractor 2001c is positioned such that a retractor member is in the region of the other pharyngoglossal fold 2057 and at least a portion of its anchor member is attached to the soft palate 2066. At least one of the first tissue retractor 2001a, the second second tissue retractor 2001b and the third tissue retractor 2001c interact to distribute a force and to prevent obstruction of the horses airway.

10. Non-Invasive Embodiments

Disclosed here, for example, a FIGS. 21A-21H and 22A-22H, are methods and devices for non-invasively retracting mucosa and displacing soft tissue volume for the treatment of sleep apnea and related disorders. A major advantage of these non-invasive retraction methods is that no surgical procedure is needed, and suitable non-invasive devices can be easily inserted and removed by, for example, the patient or the treating medical professional.

At present the only effective non-invasive therapy for sleep apnea is CPAP. CPAP displaces the soft tissue with air pressure and, although effective in many cases, it is uncomfortable for the patient and has a very low compliance rate. FIG. 4D depicts the mechanism by which CPAP relieves airway obstruction. The only other non-invasive therapies which have some effect on sleep apnea are dental devices. Other effective non-invasive therapies include the use of dental devices that work by moving the jaw down and forward, thereby indirectly moving the entire floor of mouth and tongue. By this method the airway is expanded and the mucosa connecting the jaw to the pharynx is slightly stretched and stiffened. Unfortunately, the joint connecting the jaw to the skull can only be stretched a small amount so that there is a limit to how much the airway can be expanded. Therefore, at present, dental devices are only effective in some mild sleep disorder cases. FIG. 4E depicts the mechanism by which a dental device relieves airway obstruction.

It is counterintuitive that any tissue retractor device could retract the tongue and other soft tissue in a patient's mouth without puncturing mucosa. The tongue and pharynx are highly sensitive to contact and any stimulation of the tongue and/or pharynx can cause gagging. Moreover, the whole region within the patient's mouth is covered with slippery mucosa and is always moving. Therefore, it is contrary to expectation that a non-invasive retraction device can remain in place in the soft tissue of a patient's mouth without some firm anchoring to tissue.

In one non-invasive embodiment referring now to FIGS. 21B-21C and 21G-21H a portion of a tissue retractor 2101 pushes or tugs on the PGF 2157 to retract the PGF 2157 thereby avoiding airway obstruction to airflow 2169. More specifically, the retractor member 2120 lies within the groove formed by the base 2153 of the tongue 2151 and the lateral pharyngeal wall 2165. A portion of the retractor member 2120 contacts the PGF 2157, for example, a portion of the retractor member 2120 contacts along the vertical back surface of the PGF 2157.

In one embodiment the retractor member 2120 is thin, soft and form fitted to comfortably distribute force to the mucosa of the PGF 2157. The retractor member 2120 can be made of any of a number of materials suited to placement in a patient's oral cavity or pharynx, a non-limiting example is a soft gel-like silicone such as, for example, NuSil Technology MED-6380 firm RTV gel, available from NuSil Technology LLC, Carpinteria, Calif. The retractor member 2120 can extend solely in the region of the PGF 2157. Alternatively, the retractor member can extend from the region of the PGF 2157 downward as far as the esophagus. In some embodiments the retractor member 2120 is sized to retract from the PGF 2157 to one or more of the upper esophageal spincter, the pyriform sinuses, the vocal folds, the aryepiglottic folds, the epiglottis and/or the lateral pharyngeal walls. Retractor members 2120 are sized in accordance with the desired placement and the desired extent of retraction force. The length of the retractor member 2120 can range from about 1 mm to about 100 cm, from about 0.5 cm to about 5 cm, and from about 1 cm to about 2 cm.

Retractor members 2120 are shaped to suit the region of placement and desired extent of retraction in accordance with patient anatomy. Suitable retractor members 2120 have a wedge shape or triangle shape as shown in FIG. 21H. In one embodiment, the widest plane of the wedge shaped retractor member 2120 ranges from about 1 mm to about 10 mm wide. In one embodiment, a retractor member 2120 is sized to (e.g., the wedge shaped retractor member widest plane) compresses the tongue base 2153 and decreases its compliance, thereby helping to prevent posterior collapse of the tongue base 2153. The retractor member 2120 (e.g., the wider base) can then also coax the tongue base 2153 anteriorly (FIG. 21G-21H). The retractor member 2120 can have other shapes including, but not limited to, the shapes described in FIGS. 9A-9D.

The retractor member 2120 can be the shape of a hook and the retractor member 2120 can be used at many sites disclosed herein. To remain in place without movement the hook shaped retractor member 2120 should be "loaded" to exert retraction force while in position. Positioning the retractor member 2120 at the PGF 2157 site is advantageous, because the retractor member 2120 is surrounded by tissue on all sides of the PFG 2157 and even the top of the retractor member 2120 is covered by the overhanging lateral part of the tongue 2151. In one embodiment, referring now to FIG. 21C, the retractor member 2120 has the shape of a hook and the retractor member 2120 hooks the PGF 2157 much like eyeglasses hook over the ear. The hook shaped retractor member 2120 exerts a force on the PGF 2157 that avoids the obstruction of the patient's airway. The muscles that pass from the lateral pharyngeal walls into the tongue act as a portion of a spinchter that provides and prevents access to the airway, such as during swallowing. The tissue retractors disposed on the various regions of soft tissue pull this spinchter open thereby to maintain opennes of the patient's airway.

The tissue retractor 2101 retractor member 2120 is connected to the first end of the shaft 2110 and its anchor member 2130 is connected to the second end of the shaft 2110. In some embodiments the shaft 2210 passes directly from the top of the retractor member 2120 over the PGF 2157 to connect via the anchor member 2130 with one or more of anchoring sites. Suitable anchoring sites include, for example, the patient's teeth and particularly the molars. The teeth 2198 and specifically the molars are at a relatively short distance from the PGF 2157. For example, molar teeth are at a distance of from about 1 mm to about 5 cm from the PGF 2157. Alternatively, the anchor member 2130 may be anchored to one or more dental appliances that are well known in the art. Suitable dental appliances can be anchored to teeth (e.g., molar teeth), the patient's gums, dental posts, or dental bridges.

The anchor member 2130 can couple to one or more of the patient's teeth 2198. For example, the anchor member 2130 can surround all or a portion of a patient tooth 2198. In one embodiment, the anchor member 2130 has the shape of a hook and surrounds at least a portion of the tooth 2198 (see, e.g., FIG. 21G-21H).

Dental appliances can have a wide variety of mechanisms to attach to the shaft 2110 or to an anchor member 2130. One method suitable for attaching the shaft 2110 to the a dental appliance or to a patient's teeth include the use of rubber bands, for example, rubber bands similar to those typically used in orthodontics. In one embodiment, a tissue retractor 2001 employs a orthodontic rubber band as its anchor member 2130 and the rubber band reversibly couples to a dental appliance in the patient's mouth. In another embodiment, a tissue retractor 2001 employs a rubber band as its shaft 2110, for example, one portion of a rubber band reversibly attaches to a portion of a retractor member 2120 that is placed in the region of the PGF 2157 and another portion of the rubber band reversibly attaches to an anchor member 2130 that couples to a molar. The advantage of the embodiment employing a removable shaft 2110 is that the shaft 2110 device (e.g., a rubber band) is easily removable and replaceable, completely adjustable, and the distance traveled by the shaft 2110 between the retractor member 2120 and the to anchor member 2130 could be very short, thereby achieving the goal of retraction of the PGF 2157 with minimal patient discomfort.

Referring now to FIGS. 21D-21F and 22A-22H, in another embodiment a tissue retraction clamp 2193, 2293 is designed to remain attached to a mucosal fold 2159, 2259 such as a tissue fold in a patient's oral cavity or pharynx by non-invasive means. The tissue retraction clamp 2193, 2293 can remain attached to the tissue fold for a limited amount of time, or, optionally, the tissue retraction clamp 2193, 2293 can remain attached to the tissue fold indefinitely. In one embodiment, the tissue retraction clamp 2193, 2293 is clipped over (e.g., it surrounds) a mucosal fold 2159 in the oral cavity or pharynx such that that it can remain in place for extended periods or time. Mucosal folds 2159, 2259 are malleable such that compression of the mucosal fold 2159, 2259 with the clamp 2159, 2259 indents at least a portion of the tissue of the mucosal fold 2159, 2259 and maintains the clamp 2159, 2259 substantially in its position on the mucosal fold 2159, 2259 such that the clamp 2159, 2259 resists migration out of position. (See, e.g., FIGS. 21D-F and 22A-22C).

Figures 21C, 21D, 21E, 21F:
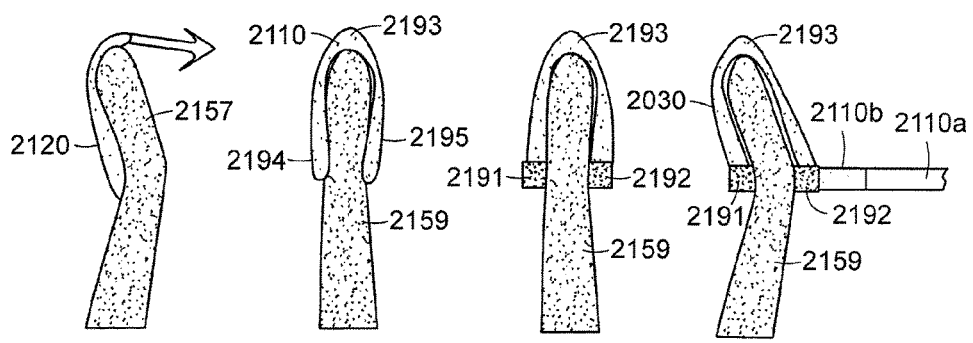
Figure 21G:
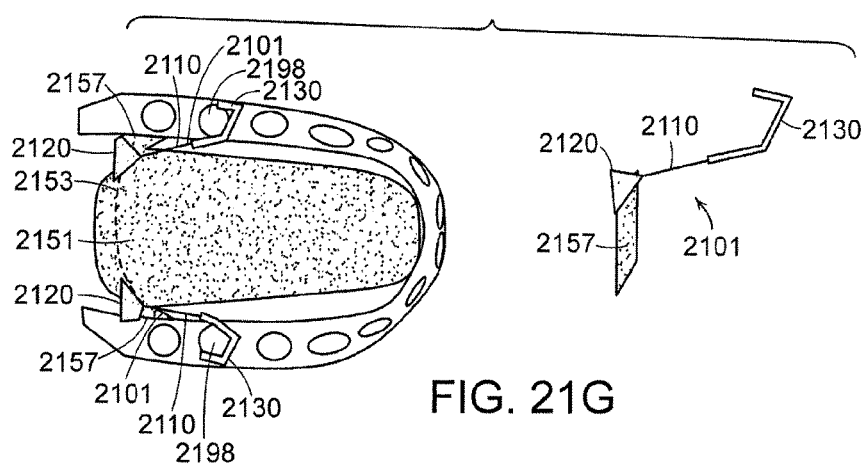
Figure 22A:
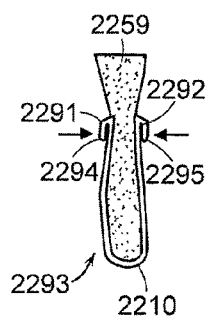
FIGS. 22A-22H illustrate a Non-invasive retraction, clamp embodiment.
Figure 22B:
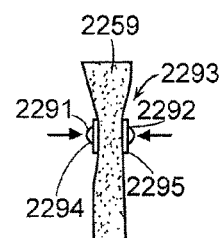
Figure 22C:
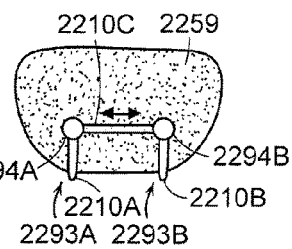

Referring now to FIGS. 21D and 22A, in some embodiments, the tissue retraction clamp 2193, 2293 is sized for placement in a patient's upper airway on, for example, a mucosal fold 2159, 2293 located in the patient's upper airway. In one embodiment, the clamp 2193, 2293 includes a first arm 2194, 2294 and a second arm 2195, 2295. A shaft 2110, 2210 can connect the first arm 2194, 2294 and the second arm 2195, 2295. For example, the first arm 2294 is connected at or near a first end of the shaft 2210 and the second arm 2295 is connected at or near a second end of the shaft 2210. In some embodiments, referring now to FIGS. 21E-21F and 22A-22B, the clamp 2193, 2293 includes a first magnet 2191, 2291 that is attracted to a second magnet 2192, 2292. The second magnet 2192, 2292 can have a polarity opposite to the first magnet 2191, 2291, alternatively, the second magnet 2192, 2292 can be made of a material (e.g., a suitable non ferrous material) to which the first magnet 2191, 2291 is attracted. In some embodiments, referring now to FIG. 22A, the first magnet 2291 is connected at or near a first end of the shaft 2210 and the second magnet 2292 is connected at or near a second end of the shaft 2210.

Mucosal folds 2159, 2259 are malleable and compression by the clamps 2193, 2293 indents the tissue fold and resists migration of the clamps 2193, 2293 out of position. In one embodiment, the ends of the arms 2194, 2195, 2294, 2295 exert a compressive force on the mucosal folds 2159, 2259. In one embodiment, the compressive force is mechanical. Suitable mechanical forces may be generated by the plastic physical properties of all or a portion of the clamp 2193, 2293. In some embodiments, a spring is incorporated into the clamp 2193, 2293, for example on one or more of the first arm 2194, 2294 and the second arm 2195, 2295. In one embodiment, all or a portion of the clamp 2193, 2293 includes nitinol or other material that maintains force. Optionally, portions of the clamp 2193, 2293 contain magnets (or a magnet and a non ferrous material) that create a force of attraction when brought in proximity to one another. In another embodiment, the clamp 2193, 2293 is loaded at its apex and the arms 2194 and 2195 or 2294 and 2295 are attracted to one another by a spring mechanism similar to what found in a paper clip.

Referring now to FIGS. 21A-21H and 22A-22H, a method for treatment of a breathing disorder includes positioning a clamp 2193, 2293 sized for placement in a patient's upper airway on a mucosal fold 2159, 2259 located in a patient's upper airway and compressing the mucosal fold 2159, 2259 with the clamp 2193, 2293 at a pressure that substantially maintains the clamp 2193, 2293 in its position on the mucosal fold 2159, 2259. The clamp 2193, 2293 indents at least a portion of the mucosal fold 2159, 2259 to prevent obstruction of the patient's airway. In some embodiments, the clamp 2193, 2293 exerts a pressure that is not greater than the perfusion pressure of the mucosal fold 2159, 2259. In some embodiments, the clamp has a first magnet 2191, 2291 and a second magnet 2192, 2292 of opposite polarity, more specifically, the first magnet 2191, 2291 is connected at or near a first end of a shaft 2110, 2210 and the second magnet 2192, 2292 of opposite polarity is connected at or near a second end of the shaft 2110, 2210. In some embodiments, the clamp 2193, 2293 has a first arm 2194, 2294 connected at or near a first end of a shaft 2110, 2210 and a second arm 2195, 2295 connected at or near a second end of the shaft 2110, 2210, the first arm 2194, 2294 is attracted to the second arm 2195, 2295 by a spring force. In some embodiments, the clamp 2193, 2293 has a shaft 2110, 2210 that exerts at least one of a protracting or a retracting force on the mucosal fold 2159, 2259.

In some embodiments, a tissue clamp 2193, 2293 for treatment of a breathing disorder includes a first arm 2194, 2294 connected at or near a first end of a shaft 2110, 2210 and a second arm 2195, 2295 connected at or near a second end of the shaft 2110, 2210. The first arm 2194, 2294, the second arm 2195, 2295 and the shaft 2110, 2210 are dimensioned to surround a mucosal fold 2159, 2259 located in a patient's upper airway. The first arm 2194, 2294 is attracted to the second arm 2195, 2295 by a force and the force indents at least a portion of the mucosal fold 2159, 2259 to prevent obstruction of the patient's airway. The force can be, for example, a magnetic force or a spring force.

In one embodiment, referring now to FIG. 21F, a clamp 2193 has a first magnet 2191 and a second magnet 2192 that is attracted to the first magnet 2191 thereby to create an attraction force that indents the mucosal fold 2159. In one embodiment, a first end of a shaft 2110A has third magnet 2110B and the third magnet 2110B is attracted to at least a portion of the clamp 2193. For example, the third magnet 2110B is attracted to the second magnet 2192. Optionally, the shaft 2110A and its third magnet 2110B are brought into proximity to the clamp 2193 thereby to move the mucosal fold 2159 in a direction that creates an indentation in at least a portion of the mucosal fold to prevent obstruction of the patient's airway. In some embodiments, the shaft 2110A is attached to an anchor member such as, for example, an anchor member that anchors about a dental structure such as, for example, a tooth. In some embodiments, a clamp 2193 placed surrounding a mucosal fold 2159 a patient's oral cavity or pharynx and when the patient seeks to "load" the tissue retractor the clamp 2193 becomes the retractor member, the magnet 2110B at the first end of the shaft 2110A is brought in proximity to the clamp 2193 and attracts to the clamp 2193, the second end of the shaft 2110 is connected to an anchor member, for example, the second end of the shaft 2110 is attached to an anchor member having a hook shape that surrounds at least a portion of the patient's tooth. Accordingly, referring now to FIGS. 21F and 22F, magnets can be used to reversibly couple a clamp 2193, 2293, to an anchor member 2230 via a shaft 2110A, 2210. In one embodiment, the clamp 2193, 2293 compresses the mucosa (e.g., the mucosal fold 2159, 2259) and the retraction via the anchor member 2230 and the shaft 2210 retracts the edge of the tissue fold.

In some embodiments, the tissue retraction clamp 2193, 2293 is clipped over (e.g., it surrounds) a mucosal fold 2159, 2259 in the oral cavity or pharynx such that that it can remain in place for extended periods or time without connection to an anchor (FIGS. 21C-21E and 22A-22D). In one embodiment, referring now to FIG. 22C, the clamp 2293 includes a shaft 2210 connected at each end by an arm (e.g., the first arm 2294 and the second arm not shown in this figure). The clamp 2293 surrounds the mucosal fold 2259 and both compresses the mucosa and retract the edge of the soft tissue fold.

Figure 22D:
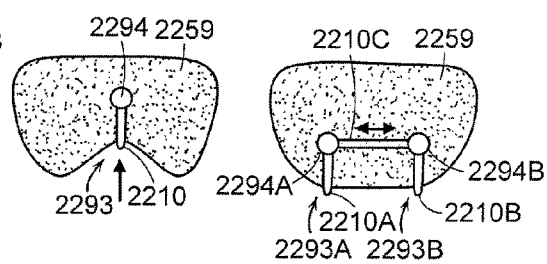
Figure 22E:
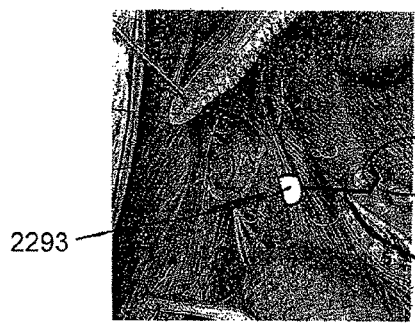
Figure 22F:
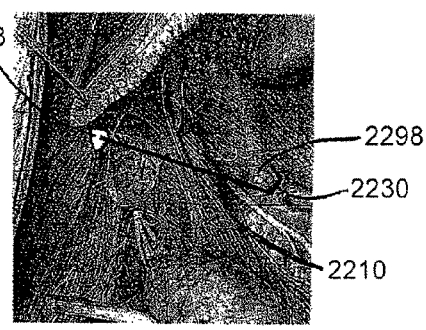
Figure 22G:
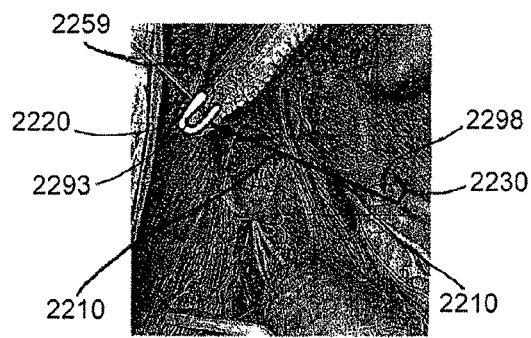

In some embodiments, multiple clamps are employed. Referring now to FIG. 22D, two clamps 2293A and 2293B are connected by a shaft 2210C that exerts force in an expanding direction between the clamps 2293A, 2293B. For example, the force provided by the shaft 2210C can protract or lengthen the soft tissue. In some embodiments, two clamps are employed to protract or lengthen tissue without use of a shaft therebetween.

Figure 22H:
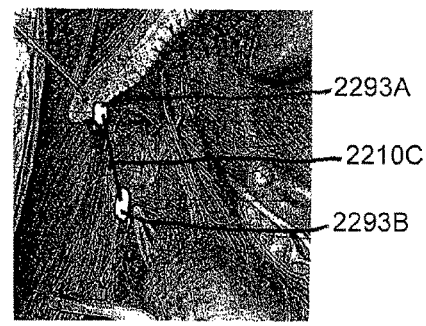

In some embodiments, referring to FIGS. 22D and 22H, a method for treatment of a breathing disorder includes positioning a clamp 2293A sized for placement in a patient's upper airway on a mucosal fold 2259 located in a patient's upper airway and compressing the mucosal fold 2259 with the clamp 2293A at a pressure that substantially maintains the clamp 2293A in its position on the mucosal fold 2259. Positioning a second clamp 2293B sized for placement in the patient's upper airway on another portion of the mucosal fold 2259 and compressing the other portion of the mucosal fold 2259 with the second clamp 2293B at a pressure that substantially maintains the second clamp 2293B in its position on the other portion of the mucosal fold 2259. The clamp 2293A indents at least a portion of the mucosal fold 2259 and the second clamp 2293B indents at least a portion of the other portion of the mucosal fold 2259 and the clamp 2293A and the second clamp 2293B exert a force (e.g., a protracting force) between the mucosal fold 2259 and the other portion of the mucosal fold 2259 to prevent obstruction of the patient's airway. In one embodiment, a shaft 2210C is disposed between the clamp 2293A and the second clamp 2293B, the shaft 2210C exerts at least one of a protracting or a retracting force on the mucosal fold 2259.

The non-invasive retractor clamp(s) 2193, 2293 can be used in all sites within the upper airway where mucosal folds 2159, 2259 are present or where mucosal folds 2159, 2259 can be formed by grasping tissue. These upper airway sites include without limitation, the PGF, the frenulum, the lateral tongue surface, tonsillar folds (FIGS. 22E-22F), the soft palate (FIG. 22G), the pharyngeal walls, the floor of the mouth, and the aryepiglottic fold. In some embodiment, indentation of the mucosal fold maintains all or a portion of the patient's airway in the open position. Some of these sites within the patient's upper airway have extensive sensory innervation, however, so long as the contact between the clamp 2193, 2293 and mucosa is stable and immobile the sensation disappears within minutes after placing the clamp 2193, 2293 about the mucosal fold 2159, 2259. This loss of sensation is called habituation and is well known to sensory physiologists. The stability of contact between the retractor clamp and the region of mucosa can be increased by the use of adhesives known in the art. Adhesives effective on mucosa can include, but are not limited to, fibrin, hydrogels, and cyanoacrylic glues. It is also important that the site for the clamp 2193, 2293 as well as the shaft 2110, 2210 and the anchor 2130, 2230 be placed such that the least amount of dynamic contact occurs between these various components and the mucosa. In addition, when a clamp 2193, 2293 is used on an ongoing basis the compression exerted by the clamp 2193, 2293 (e.g., the compression between the arms of the clamp 2193, 2293) should not exceed the pressure at which capillary blood circulation stops, called the perfusion pressure, which is about 25 mm Hg or 34 cm $H_2O$.

Figures 23A, 23B, 23C:
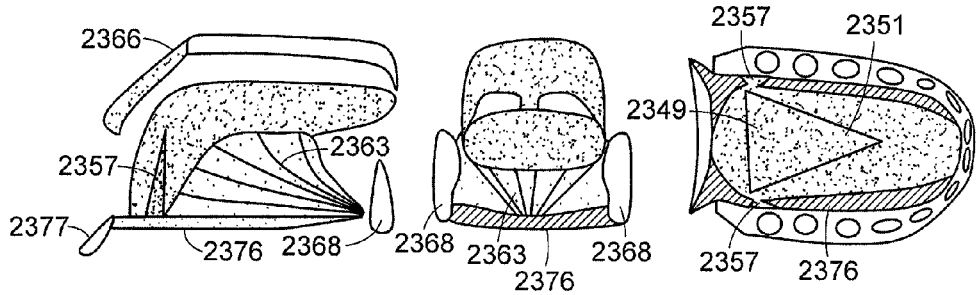
FIGS. 23A-23N illustrate Non-invasive protraction and vacuum devices.

Referring now to FIGS. 23A-23L, other non-invasive methods and devices for soft tissue and/or mucosa protraction and/or retraction use vacuum and/or bolsters to displace, protract, and/or to retract soft tissue. FIG. 23A is a side view showing a patient's floor of mouth 2376 that extends from the mandible 2368 to the hyoid bone 2377. FIG. 23B is a front view showing that the floor of mouth 2376 connects to the bottom of each side of the mandible 2368. FIG. 23C is a top view showing the tongue 2351 and the triangular root 2349 of the tongue below the tongue 2351. The anterior extension of the root 2349 is the genioglossus muscle 2363 (seen in FIGS. 23A and 23B) that inserts into the mandible 2368.

Another embodiment of this invention is to increase the pharyngeal airspace by depressing the floor of the mouth. The floor of the mouth 2376 is composed of muscles and other soft tissue that attaches to the hyoid bone 2377 posteriorly and attaches to the mandible 2368 anteriorly and laterally. The tongue 2351 sits on the floor of the mouth 2376 and follows its movements. For example when the jaw is moved forward or downward the tongue 2351 moves along with it. Similarly when the hyoid bone 2377 moves forward it displaces the back of the tongue in the same direction. Some surgical procedures try to take advantage of this relationship by wiring the hyoid bone 2377 in a more forward position by wiring it to the front of the mandible 2368. Unfortunately, the hyoid bone 2377 has many other attachments that resist being repositioned.

In contrast to prior approaches that focus on moving the bony attachments of the floor of the mouth 2376, in one embodiment, the soft tissue of the floor of the mouth 2376 is moved/repositioned. Specifically, in one embodiment, the bottom of the tongue (i.e., the root of the tongue 2349) that rests on the floor of the mouth 2376 is triangular shaped and smaller then the overall area of the floor of the mouth 2376 (FIG. 23I). Therefore the floor of the mouth 2376 can be reached between the tongue root 2349 and the mandible 2368. When the area between the tongue root 2349 and the mandible 2368 is depressed the root of the tongue 2349 is depressed as well. Although the entire exposed floor of the mouth 2376 can be depressed, this is inefficient, as the most important area to move is the tongue base.

Figures 23D, 23E, 23F:
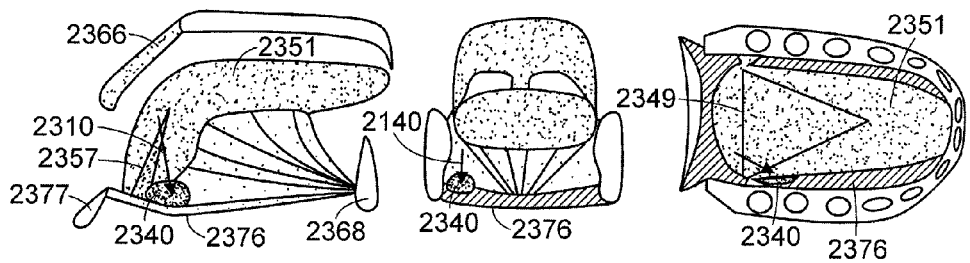
Figures 23G, 23H, 23I:
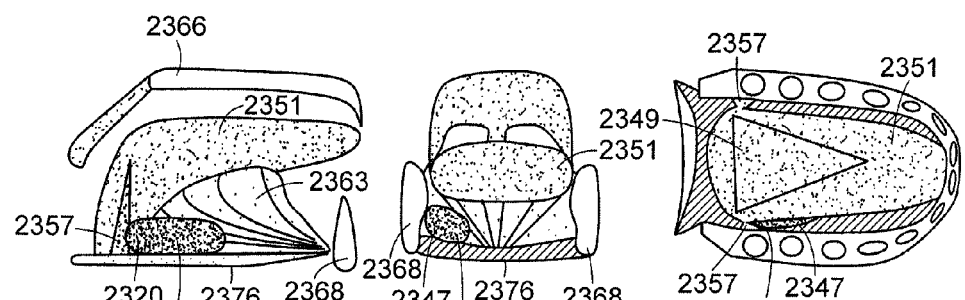

Referring now to FIG. 23D a bolster 2340 is pushed downward and slightly anterior by a shaft 2310. The shaft 2310 and the bolster 2340 exert a protracting force on the floor of mouth 2376. The protracting force indents the floor of mouth 2376, which alters the position of the tongue 2351 and the PGF 2357. Referring now to FIG. 23E, the floor of mouth 2376 is depressed by the bolster 2340, which creates room that depresses the tongue 2351 by the same amount that the floor of the mouth 2376 is depressed, which results in a decreased height of tongue 2351 surface at, for example, the tongue curve. Referring now FIG. 23F, the bolster 2340 is seen from above. Note the anterior displacement of the base of the tongue 2351 that results from use of the bolster 2340.

In one embodiment, the area of the floor of the mouth 2376 around the tongue base is depressed thereby moving the tongue base down and as a result of the downward movement of the tongue base the pharyngeal airspace is increased. For practical purposes the PGF 2357 places a limit on how far back the floor of the mouth 2376 can be reached. In one embodiment a tissue retractor with a silicon bolster 2340 measuring 0.5 cm×0.5 cm×1 cm is situated longitudinally alongside the undersurface of the tongue 2351 with one end abutting the PGF 2357. In one embodiment, downward pressure exerted on the bolster 2340 is achieved by a dental appliance attached to the molar teeth or a palatal prosthesis that is connected to the bolster 2340 by, for example, the shaft 2310. The downward pressure exerted on the bolster 2340 depresses he floor of the mouth 2376. The bolster 2340 exerts a protracting force on the floor of the mouth 2376. Not all the downward movement of a local area of floor of mouth 2376 depression is transferred to the tongue 2351. However, an increase in the pharyngeal airspace that avoids obstruction of the patient's airway is beneficial.

In addition to depression of the floor of the mouth 2376, the displacement force can be exerted forward (anterior), inward (medial) or outward (lateral). Forward displacement is beneficial, because the pharyngeal airspace is expanded to the extent that the tongue base also moves forward. Inward movement is beneficial if both sides exert a grasping force on the tongue 2351 and thereby resist backward tongue collapse. Outward movement is also beneficial to the extent that the outward movement stretches and tenses tongue tissue thereby also preventing backward tongue collapse.

Non-invasive coupling to mucosa in the oral cavity or pharynx is difficult. Reversible non-invasive coupling may be accomplished by using vacuum to suck a volume of mucosa into the vacuum opening. FIG. 23G shows a vacuum device 2347 retractor member 2320 applied to the lateral tongue 2351. The vacuum device 2347 is positioned below the tongue 2351 adjacent the floor of mouth 2376 and the PGF 2357. FIG. 23H shows a vacuum device 2347 employed as a retractor member 2320 that displaces tongue 2351 tissue. Use of the vacuum device 2347 results in tongue 2351 tissue displacement that is reflected by the decreased height of the tongue 2351 surface. FIG. 23I shows a vacuum device 2347 employed as a retractor member 2320 that displaces tongue 2351 tissue and results in anterior displacement of the base of the tongue 2351 that avoids obstruction of the airway due to collapse of the tongue 2351 toward the soft palate 2366 (see FIG. 23G).

Referring now to FIGS. 23G-23I, vacuum can be applied through suction or vacuum devices 2347 placed over segments of the tongue 2351 to cause displacement of tongue 2351 tissue into the suction. Because the volume of a patient's tongue 2351 is constant, the use of suction on the tongue 2351 tissue displaces a portion of tongue 2351 tissue and the displaced tongue 2351 tissue is moved from other parts of the tongue 2351. In one embodiment, suction is employed on a portion of a patient's tongue 2351 tissue and displaces tongue 2351 tissue from the tongue base. Vacuum can be used to displace soft tissue volume, for example, vacuum can be used on the tongue 2351 by a relatively large device that sucks tissue volume into the vacuum device 2347 and thereby changes the shape of the tongue 2351 such that volume is removed from the tongue base. Referring now to FIGS. 23G-23I, in one embodiment a retraction member 2320 is a vacuum device 2347 that is applied to the lateral tongue 2351. The vacuum device 2347 is positioned below the tongue 2351 adjacent the floor of mouth 2376 and the PGF 2357. The vacuum device 2347 vacuums and displaces a portion of the tongue 2351 tissue. The displacement of the tongue 2351 tissue is reflected by the decreased height of the tongue 2351 surface (see FIG. 23E). The vacuum device 2347 tongue 2351 tissue displacement results in anterior displacement of the base of the tongue 2351 thereby to avoid obstruction of the airway due to collapse of the tongue toward the soft palate 2366 (see FIG. 23G).

Vacuum can be employed through suction devices that can be used to suction a retractor member onto a mucosal surface thereby to non-invasively attach the retractor member within the patient's oral cavity or pharynx. In one method, vacuum device 2347 is used to couple a retractor member to mucosa in the patient's oral cavity or pharynx. In one embodiment, the vacuum device 2347 is a retractor member 2320 that is applied to the PGF, for example, to the anterior surface of the PGF. Other suitable sites for placement of a vacuum device 2347 retractor member 2320 are the lateral and/or inferior tongue surface. Vacuum retraction may be applied to any suitable tissue and/or mucosa surface at a location in the oral cavity or pharynx where tissue retraction is beneficial to prevent patient airway obstruction.

Figure 23J:
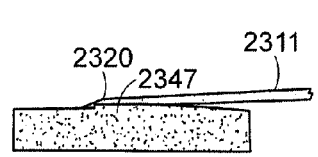
Figure 23K:
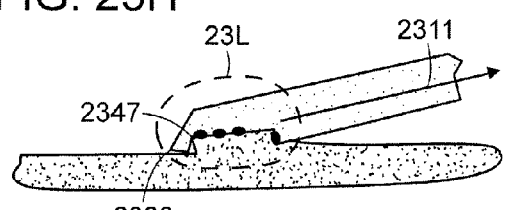
Figure 23L:
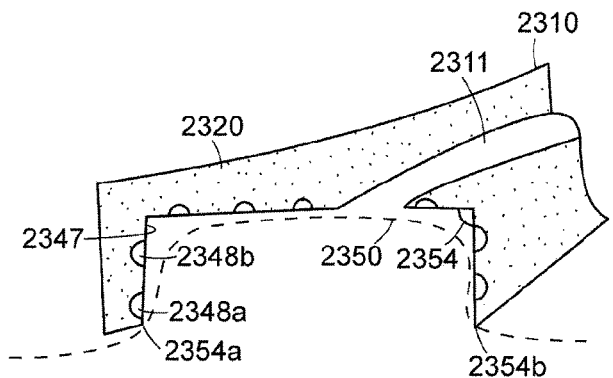

FIG. 23J shows a view of another vacuum device 2347. FIG. 23K shows a close up view of the vacuum device 2347 of FIG. 23J employed as a tissue retractor. FIG. 23L shows a close up view of the vacuum device 2347 of FIG. 23K employed as a tissue retractor. Once this tissue is pulled into the vacuum device 2347 its interface with the walls of the vacuum device 2347 directly locks the tissue 2350 in place within the interior walls. In other words, if the retractor member 2320 is pulled in a lateral direction, the tissue 2350 is pulled also. The vacuum mechanism can be used in place of or in addition to embedded magnets, clips, or other tissue retraction devices. The vacuum device 2347 retractor member 2320 can include a suction cup of the type well known in the art and the vacuum is formed by pressing the suction cup against the patient's mucosa.

Figure 23M:
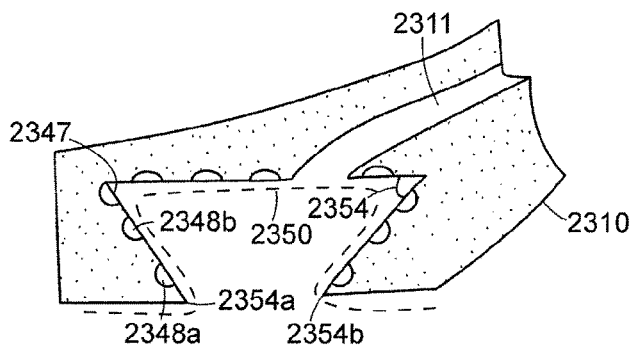
Figure 23N:
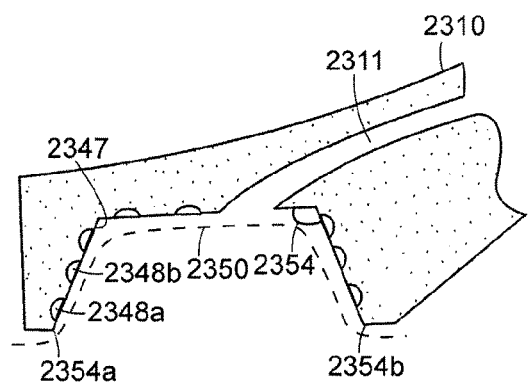

Referring now to FIGS. 23L-23N, in one embodiment, the interface between the suction device and the mucosa has well defined edges with interior walls of the vacuum device 2347 having an angle 2354 of between about 120° or less. In one embodiment, the angle 2354 is about 90°. In another embodiment, the angle 2354 is about 45°.

In one embodiment, referring now to FIGS. 23J and 23K, the vacuum device 2347 is connected via a tube 2311 to a vacuum source, for example. The tube 2311 allows vacuum to be delivered to the tissue 2450. The vacuum device 2347 can be many sizes and shapes, a simple embodiment is a round opening 1 cm in diameter with inner walls 5 mm in depth. In one embodiment, the vacuum travels from a vacuum source via a tube 2311 to the vacuum device 2347, which is positioned in the patient's mouth. In another embodiment the vacuum device 2347 is attached to a small air pump located and/or positioned in the patient's mouth.

Small electric pumps within the mouth can also be a source of vacuum. The air pump may be passive, composed, for example, of a small bladder with a one way valve such that movements of the tongue or jaw that compress the bladder force air out of the bladder through the one way valve. The elastic drive of the bladder to return to its larger volume shape forms the vacuum that attaches to tissue and/or that displaces tissue volume. The vacuum can be from a source inside the mouth and hooked to the vacuum device 2347 at some convenient spot via a tube. The amount of vacuum is sufficient to draw tissue into the coupler but not cause damage. Preferably this ranges from 0.1 to 100 cm of water pressure, in some embodiments, from 1 to 10 cm of water pressure.

The vacuum device 2347 is applied to a site to be moved and then vacuum is applied by the vacuum device 2347. Turning off the vacuum or breaking the seal allows the vacuum device 2347 to disengage. In one embodiment, the maintenance of vacuum without leakage is aided by placing biocompatible viscous material in the area of soft tissue that contacts the inner walls of the vacuum device 2347. An example of such biocompatable viscous material is the patient's own mucous.

In some embodiments, the vacuum device 2347 is attached to a modified anchor. In one embodiment, after a vacuum device 2347 couples to the mucosa it is displaced forward by a shaft. The vacuum device 2347 can have a single suction interface or, referring to FIG. 23L, multiple smaller suction interfaces 2348a, 2348b etc. (e.g., mini suction cups). Viscous mucoid material or adhesive could be applied to the mucosa to aid in maintaining a seal between the mucosa and the vacuum device 2347. Referring now to FIGS. 23J-23N, in one embodiment, a vacuum device 2347 includes one or more suction cup that suctions small amounts of tissue into the suction cup opening. The presence of the suction cup provides resistance to shear forces acting at the suction site.

FIG. 23L shows a vacuum device 2347 having an angle 2354 of about 90°. It can be seen that the soft tissue 2350 pulled into the vacuum device 2347 conforms to the walls of the vacuum device 2347 such that the soft tissue 2350 resists lateral movement. FIG. 23M shows another vacuum device 2347 having an angle 2354 of about 45°. The 45° angle is a size small enough to trap the soft tissue 2350 within the vacuum device 2347. Further, the edges 2354a, 2354b trap the soft tissue 2350 such that the soft tissue 2350 resists movement when the angles 2354 measure about 45°. In one embodiment, the vacuum device 2347 is attached to a lumen and suction is pulled through the vacuum device 2347 through the lumen of the tube 2311. In some embodiments, the soft tissue 2350 is pulled into and trapped inside the lumen of the tube 2311. Referring still to FIG. 23M, the edges 2354a, 2354b form a rim around a portion of the vacuum device 2347 that prevents movement of the soft tissue 2350. In this way, the shape of the vacuum device 2347 shown in FIG. 23M resists the soft tissue 2350 from dislodging from the vacuum device 2347.

FIG. 23N shows another vacuum device 2347 having an angle 2354 of about 135° as the angle 2354 increases, somewhere around 135°, the walls and/or the edges 2354a, 2354b cannot prevent the soft tissue 2350 from sliding out of the vacuum device 2347.

Referring now to FIGS. 23L-23N the vacuum device 2347 can grab the soft tissue 2350 and in some embodiments, can prevent motion, e.g., lateral motion, of the soft tissue 2350 by trapping the soft tissue 2350 within the vacuum device 2347. In some embodiments, the vacuum device 2347 acts an an anchor to which members such as, for example, a shaft and/or a retractor member can be attached. For example, in one embodiment, the vacuum device 2347 is coupled to soft tissue 2350 on the collgeneous top surface of the tongue where the tongue is stiff and is not easily movable.

In other embodiments, the vacuum device 2347 grabs soft tissue 2350 such that the soft tissue 2350 together with the vacuum device 2347 can be moved in a direction that avoids blocking airflow. In this way, the vacuum device 2347 may retract soft tissue 2350. For example, the vacuum device 2347 grabs soft tissue 2350 on the tip of the patient's tongue such that the tongue may be retracted by exerting a pulling force on the vacuum device 2347 and moving an attached shaft 2310 in a desired direction of retraction.

Some tissue retractors initiate desirable remodeling of the patient's tissue. For example, in an embodiment where the retractor member has a head that measures between about 2 and about 3 cm in diameter the retractor member head is implanted in tongue tissue. Over a few months the tongue tissue remodels/reshapes to become thinner in the region exposed to the retractor head. For example, the tongue adapts quickly to pressure placed on it. After the tissue retractor has been placed for from about 1 to about 2 months the tissue retractor may need to be adjusted to compensate to the thinning of the tongue tissue. In some embodiment, all or a portion of the tissue retractor is designed in a manner that encourages tissue remodeling. Tissue remodeling can be permanent reshaping of tissue for beneficial effect. Alternatively, tissue remodeling can be semi-permanent reshaping of tissue for beneficial effect.

It is to be understood that the described embodiments are merely illustrative and that variations of the above-described embodiments can be devised by one skilled in the art without departing from the scope of the invention. It is therefore intended that all such variations be included within the scope of the following claims and their equivalents.

What is claimed is:

1. A method for treatment of a breathing disorder caused by a deformation of a tongue curve, the method comprising:
    inserting a shaft of a tissue retractor through a mucosal covering of and into the tongue curve along a midline of a patient's tongue;
    positioning a retractor member of the tissue retractor on the mucosal covering of the tongue curve along the midline of the patient's tongue, the retractor member located at or near a first end of the shaft; and
    positioning an anchor member, connected to a second end of the shaft, on a mucosal covering that is the frenulum of the patient's tongue, such that the anchor member is positioned along the midline of the patient's tongue, the shaft between the retractor member and the anchor member such that the retractor member and the anchor member are on opposite sides of the patient's tongue.

2. The method of claim 1, wherein the shaft, the retractor member, and the anchor member interact to establish a force along the midline of the patient's tongue to displace the patient's tongue and prevent the sleep breathing disorder caused by the deformation of the tongue curve.

3. The method of claim 2, wherein the force along the midline of the patient's tongue exerted to prevent the deformation of the tongue curve is between 10 grams to 100 grams.

4. The method of claim 1, wherein an elasticity of the shaft generates a force to prevent the sleep breathing disorder caused by the deformation of the tongue curve.

5. The method of claim 4, wherein the force along the midline of the patient's tongue exerted to prevent the deformation of the tongue curve is between 10 grams to 100 grams.

6. The method of claim 1, wherein the shaft or a portion of the shaft is distensible.

7. The method of claim 6, wherein the amount of distensibility is between 0.01 cm and 10 cm.

8. The method of claim 1, wherein the retractor member and the shaft are integrally formed.

9. The method of claim 1, wherein the shaft comprises one of a compressed elastic, a compressed spring element or a nitinol wire.

10. The method of claim 1, wherein the shaft has a fixed length.

11. The method of claim 1, wherein the shaft is flexible.

12. The method of claim 1, wherein the shaft is rigid.

13. A method for treatment of a breathing disorder caused by a deformation of a tongue base, the method comprising:
   inserting a shaft of a tissue retractor through a mucosal covering of and into the tongue base along a midline of a patient's tongue;
   positioning a retractor member of the tissue retractor on the mucosal covering of the tongue base along the midline of the patient's tongue, the retractor member located at or near a first end of the shaft; and
   positioning an anchor member, connected to a second end of the shaft, on a mucosal covering that is the frenulum of the patient's tongue, such that the anchor member is positioned along the midline of the patient's tongue, the shaft between the retractor member and the anchor member such that the retractor member and the anchor member are on opposite sides of the patient's tongue.

* * * * *